US011235001B2

(12) United States Patent
Sugiyama et al.

(10) Patent No.: US 11,235,001 B2
(45) Date of Patent: Feb. 1, 2022

(54) RUNX INHIBITOR

(71) Applicant: KYOTO UNIVERSITY, Kyoto (JP)

(72) Inventors: Hiroshi Sugiyama, Kyoto (JP); Yasuhiko Kamikubo, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 330 days.

(21) Appl. No.: 16/321,129

(22) PCT Filed: Jul. 21, 2017

(86) PCT No.: PCT/JP2017/026578
§ 371 (c)(1),
(2) Date: Apr. 18, 2019

(87) PCT Pub. No.: WO2018/021200
PCT Pub. Date: Feb. 1, 2018

(65) Prior Publication Data
US 2019/0247425 A1 Aug. 15, 2019

(30) Foreign Application Priority Data

Jul. 29, 2016 (JP) .............................. JP2016-150560
Dec. 1, 2016 (JP) .............................. JP2016-234399
Mar. 31, 2017 (JP) .............................. JP2017-072380

(51) Int. Cl.
A61K 31/787 (2006.01)
A61P 35/00 (2006.01)
A61K 45/00 (2006.01)
A61K 31/5377 (2006.01)
C07D 239/94 (2006.01)
A61K 31/7008 (2006.01)
C12N 15/113 (2010.01)
A61K 31/196 (2006.01)
A61P 35/02 (2006.01)
A61K 31/496 (2006.01)
C07D 401/04 (2006.01)
C07D 403/06 (2006.01)
A61P 43/00 (2006.01)
A61K 31/506 (2006.01)
A61P 37/08 (2006.01)

(52) U.S. Cl.
CPC .......... A61K 31/787 (2013.01); A61K 31/196 (2013.01); A61K 31/496 (2013.01); A61K 31/506 (2013.01); A61K 31/5377 (2013.01); A61K 31/7008 (2013.01); A61K 45/00 (2013.01); A61P 35/00 (2018.01); A61P 35/02 (2018.01); A61P 37/08 (2018.01); A61P 43/00 (2018.01); C07D 239/94 (2013.01); C07D 401/04 (2013.01); C07D 403/06 (2013.01); C12N 15/113 (2013.01)

(58) Field of Classification Search
CPC .................................................. A61K 31/787
See application file for complete search history.

(56) References Cited

U.S. PATENT DOCUMENTS

| 6,472,537 B1 | 10/2002 | Baird et al. |
| 6,559,125 B1 | 5/2003 | Dervan et al. |
| 7,368,255 B2 | 5/2008 | Bae et al. |
| 2004/0146986 A1 | 7/2004 | Bae et al. |
| 2008/0261883 A1 | 10/2008 | Bae et al. |
| 2016/0208246 A1 | 7/2016 | Groner et al. |

FOREIGN PATENT DOCUMENTS

| JP | 2004-529619 | 9/2004 | |
| WO | WO-9837067 A1 * | 8/1998 | ......... C07K 5/06182 |
| WO | 2014/113406 | 7/2014 | |
| WO | 2016/025744 | 2/2016 | |

OTHER PUBLICATIONS

Jacobs et al. PLoS One, 2013, 8 e69083 (Year: 2013).*
Swalley et al. J. Am. Chem. Soc. 1997, 119, 6953-6961 (Year: 1997).*
Morita et al. J. Clin. Invest. 2017, 127, 2815-2828 (Year: 2017).*
Yu et al. Eur. J. Med. Chem. 2017, 138, 320-327 (Year: 2017).*
CAS Registry No. 191916-03-7, which entered STN on Jul. 31, 1997 (Year: 1997).*
Extended European Search Report dated Apr. 21, 2020 in corresponding European Patent Application No. 17834207.7.
Ohba et al., "Patched1 Haploinsufficiency Increases Adult Bone Mass and Modulated Gli3 Repressor Activity", Developmental Cell, 2008, vol. 14, pp. 689-699.
Han et al., "A Synthetic DNA-Binding Domain Guides Distinct Chromatin-Modifying Small Molecules to Activate an Identical Gene Network", ANGEWANDIE CHEMIE, International Edition, 2015, vol. 54, No. 30, pp. 8700-8703.
Walker et al., "Estimation of the DNA sequence discriminatory ability of hairpin-linked lexitropsins", Proceedings of the National Academy of Sciences, USA, 1997, vol. 94, No. 11, pp. 5634-5639.
Sugimoto et al., "Silencing of RUNX2 enhances gemcitabine sensitivity of p53-deficient human pancreatic cancer AsPC-1 cells through stimulation of TAp63-mediated cell death", Cell Death Discovery, 2015, vol. 1, No. 1, pp. 1-10.
Kamikubo, Yasuhiko, "Genetic compensation of RUNX family transcription factors in leukemia", Cancer Science, 2018, vol. 109, No. 8, pp. 2358-2363.
Maeda et al., "Molecular Characteristics of DNA-Alkylating PI Polyamides Targeting RUNX Transcription Factors", Journal of the American Chemical Society, 2019, vol. 141, No. 10, pp. 4257-4263.

(Continued)

Primary Examiner — Matthew P Coughlin
(74) Attorney, Agent, or Firm — Wenderoth, Lind & Ponack, L.L.P.

(57) ABSTRACT

Provided are a RUNX inhibitor which binds to a RUNX-binding sequence on DNA and thus inhibits the binding of a RUNX family member to the sequence; an antitumor agent comprising the RUNX inhibitor; and an antiallergic agent comprising the RUNX inhibitor.

13 Claims, 42 Drawing Sheets
Specification includes a Sequence Listing.

(56) References Cited

OTHER PUBLICATIONS

Kamikubo, Yasuhiko, "CROX (Cluster Regulation of RUNX) as a Potential Novel Therapeutic Approach", Molecules and Cells, 2020, vol. 43, No. 2, pp. 198-202.

International Search Report dated Sep. 5, 2017 in International Application No. PCT/JP2017/026578.

International Preliminary Report on Patentability dated Feb. 7, 2019 in International Application No. PCT/JP2017/026578.

Cunningham, L et al., "Identification of benzodiazepine Ro5-3335 as an inhibitor of CBF leukemia through quantitative high throughput screen against RUNX1-CBFβ interaction", PNAS Sep. 4, 2012 109 (36) p. 14592-14597.

Pandian, G.N. et al., "Distinct DNA-based epigenetic switches trigger transcriptional activation of silent genes in human dermal fibroblasts", Sci Rep. 2014; 4: 3843.

Saha, A. et al., "Synthesis and biological evaluation of a targeted DNA-binding tran-scriptional activator with HDAC8 inhibitory activity", Bioorganic & Medicinal Chemistry 21 (2013), p. 4201-4209.

Bando, T. et al., "Synthesis and Biological Properties of Sequence-Specific DNA-Alkylating Pyrrole-Imidazole Polyamides", Acc. Chem. Res. 2006, 39, p. 935-944.

Minoshima, M. et al., "Molecular design of sequence specific DNA alkylating agents", Nucleic Acids Symp Ser (Oxf). 2009; (53): p. 69-70.

Dickinson, A. et al., "Arresting Cancer Proliferation by Small-Molecule Gene Regulation", Chem Biol, vol. 11, p. 1583-1594, 2004.

Jacobs, P.T., et al., "Runx Transcription Factors Repress Human and Murine c-Myc Expression in a DNA-Binding and C-terminally Dependent Manner", PLoS One, 2013, vol. 8, No. 7, e69083, ISSN p. 1932-6203.

Choi, J.Y., et al., "Subnuclear targeting of Runxy/Cbfa/AML factors is essential for tissue-specific differentiation during embryonic development", Proc Natl Acad Sci USA, 2001, vol. 98, No. 15, p. 8650-8655.

Zhang, Y. et al, , "Targeting a DNA Binding Motif of the EVI1 Protein by a Pyrrole-Imidazole Polyamide", Biochemistry, 2011, vol. 50, No. 48, p. 10431-10441.

Morita, K. et al., "Genetic regulation of the RUNX transcription factor family has antitumor effects", J Clin Invest, Jul. 2017, No. 7, p. 2815-2828.

Office Action dated Jul. 27, 2021 in corresponding Chinese Patent Application No. 201780060206.5, with English Translation, 20 pages.

Official Action dated Aug. 31, 2021 in corresponding Japanese Application No. 2018-529858, with Machine English Translation, 10 pages.

\* cited by examiner

[FIG. 1]
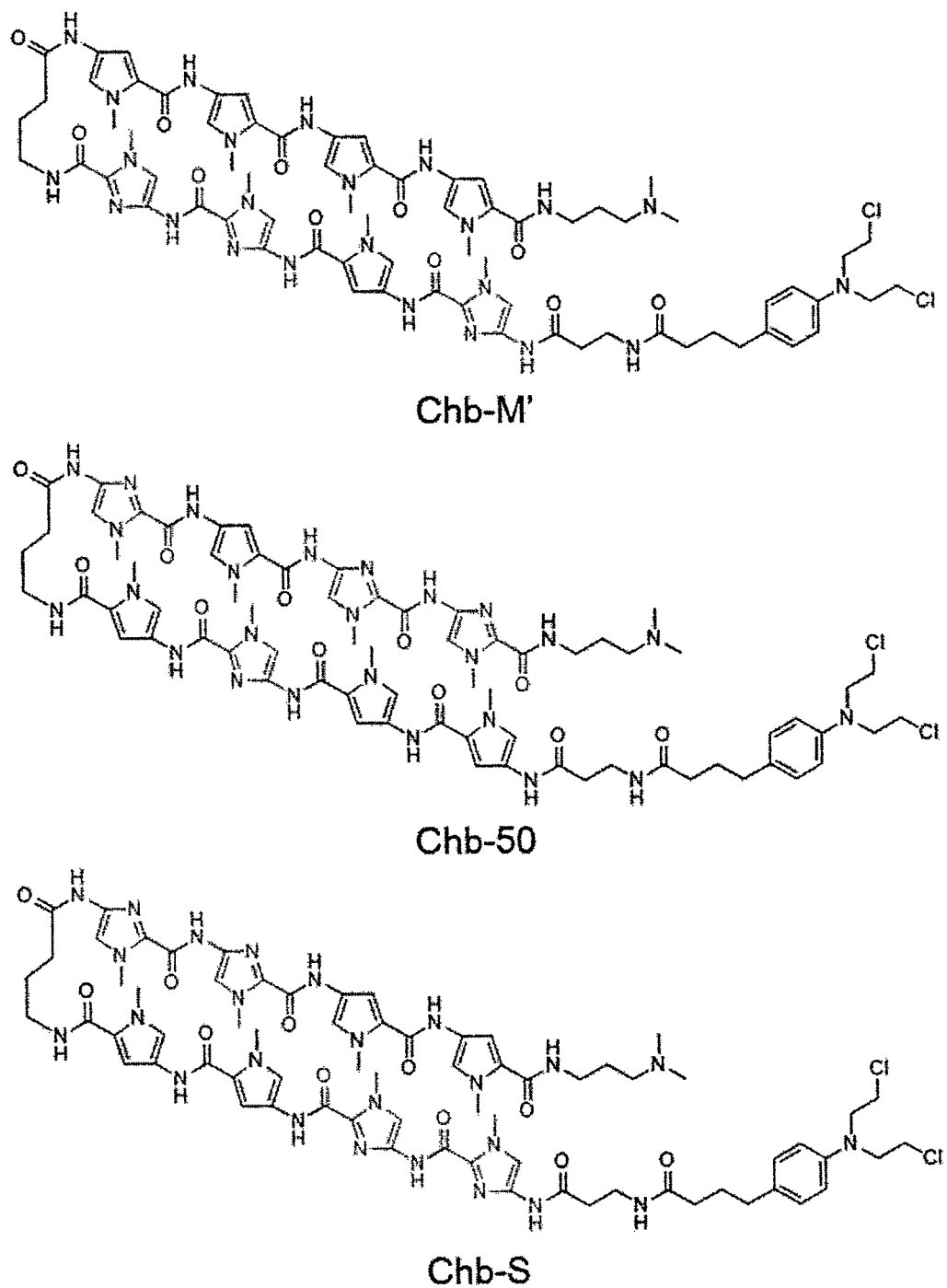
Chb-M'
Chb-50
Chb-S

[FIG. 2]
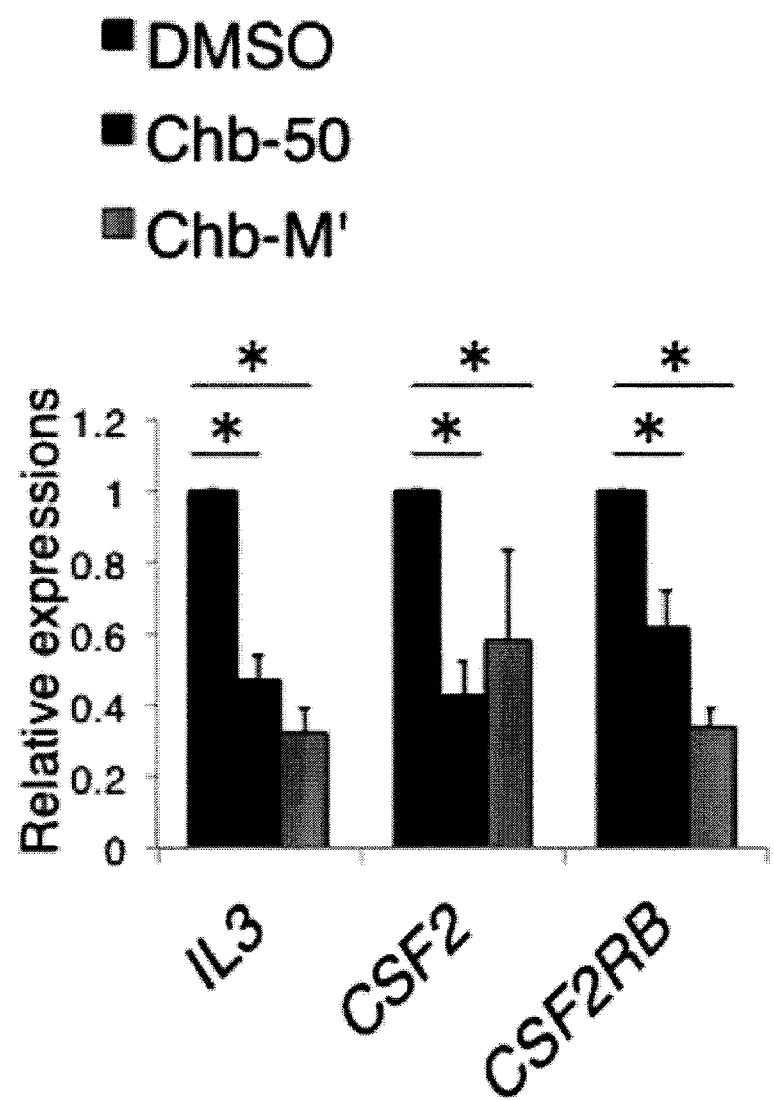

[FIG. 3]
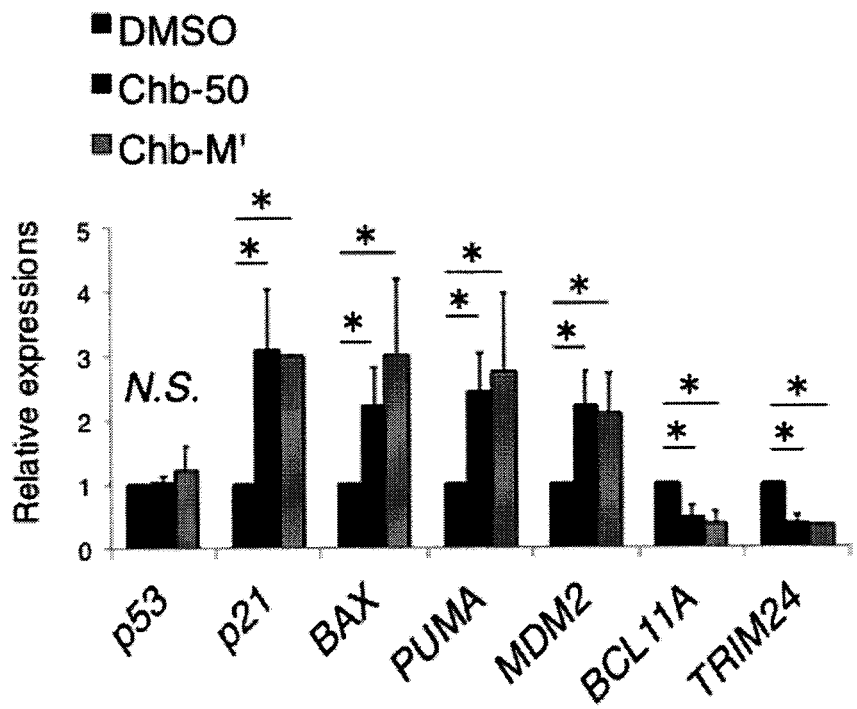
[FIG. 4]
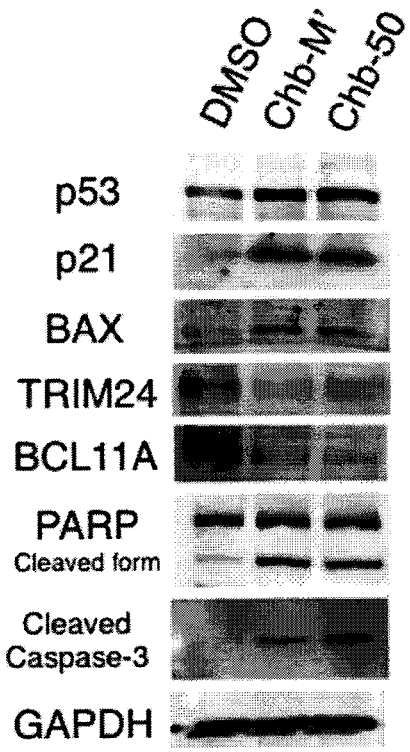

[FIG. 5]
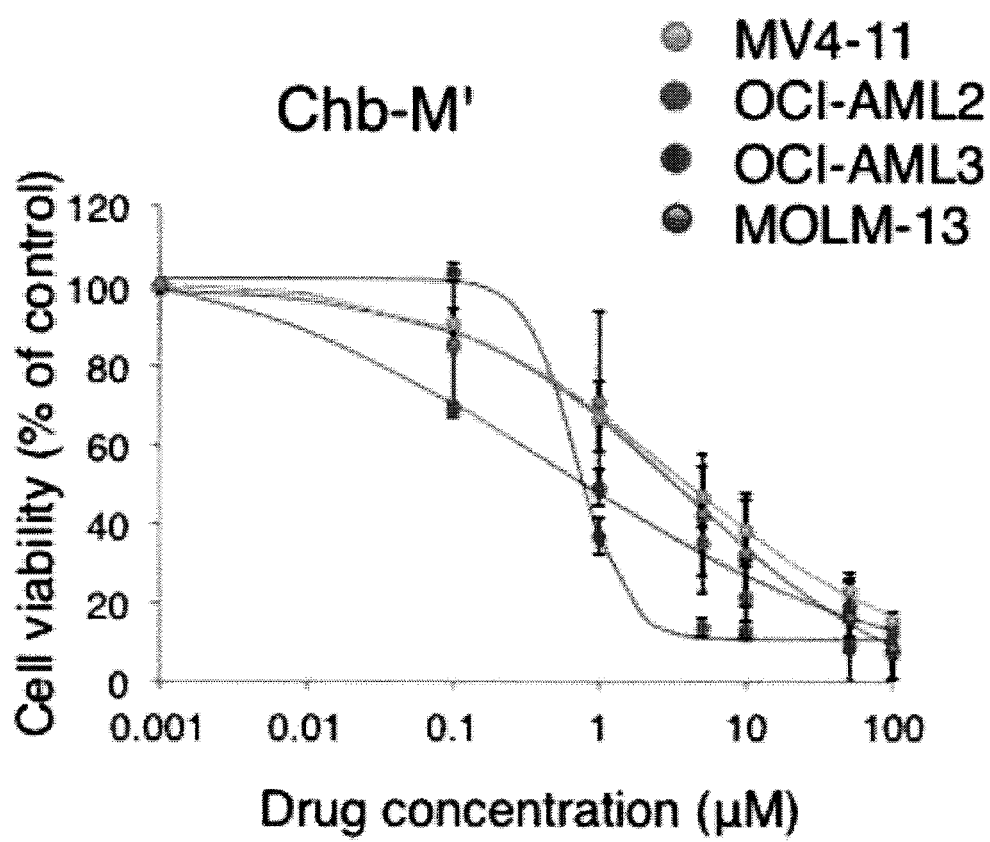

[FIG. 6]
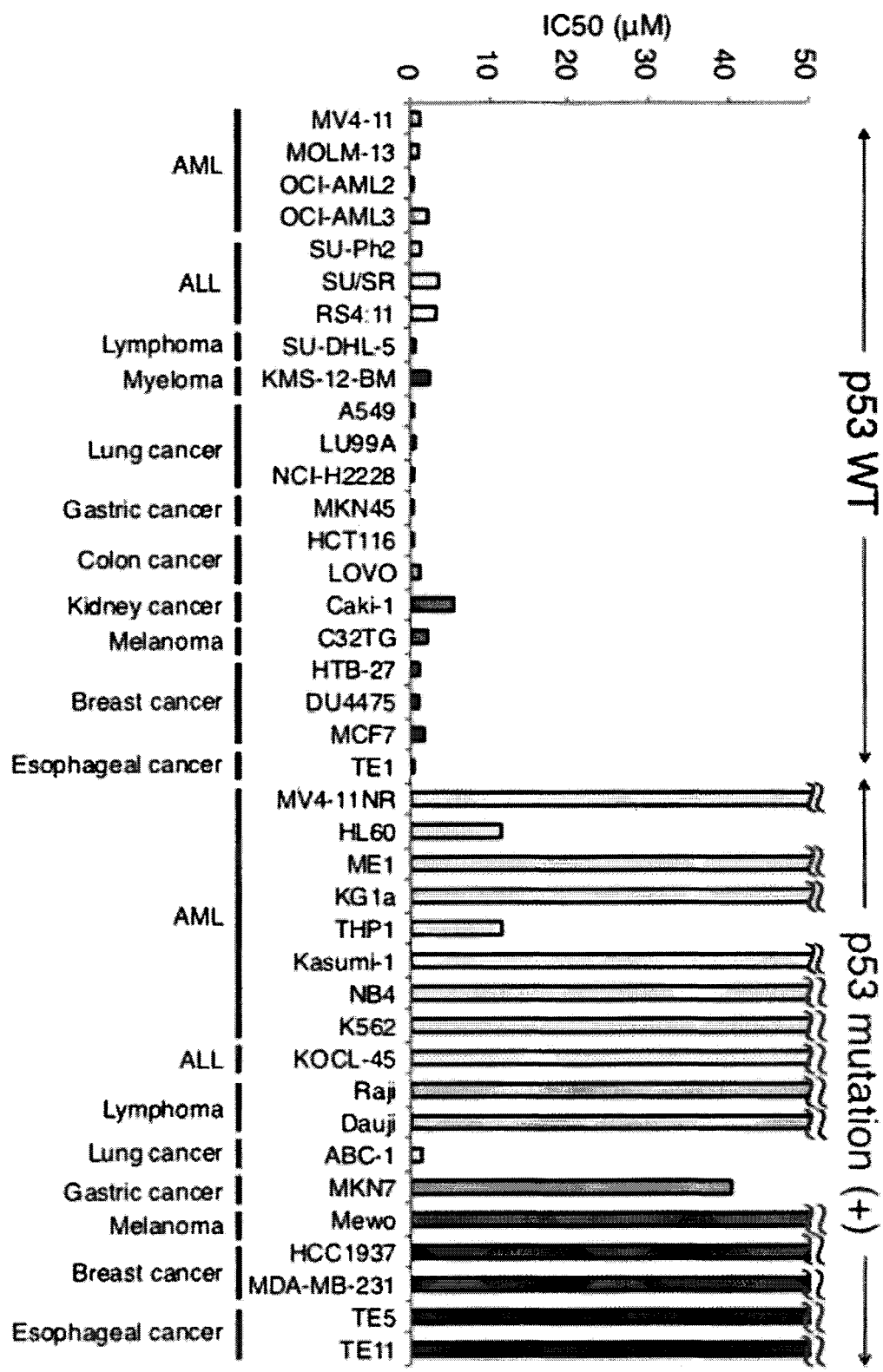

[FIG. 7]
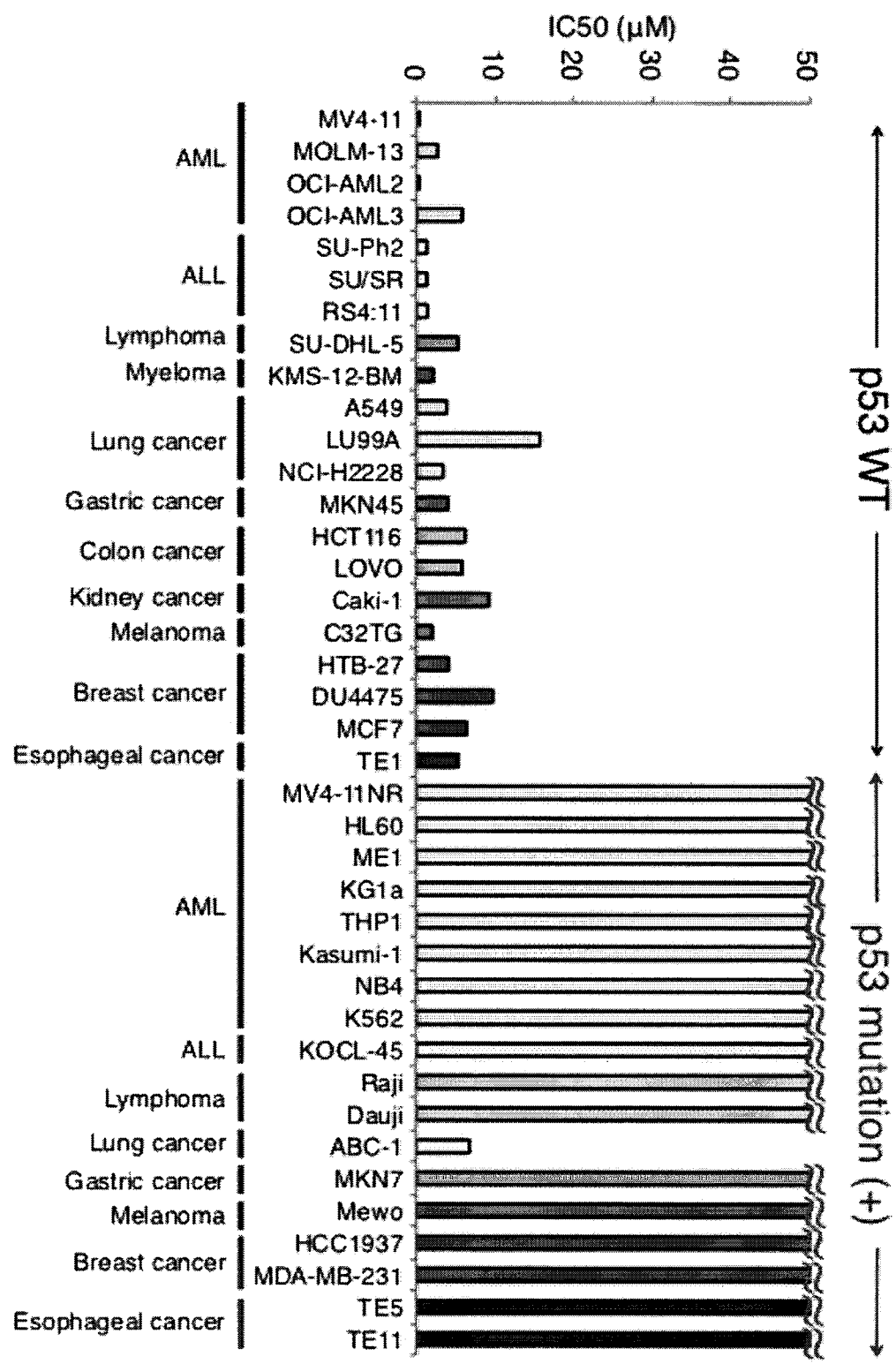

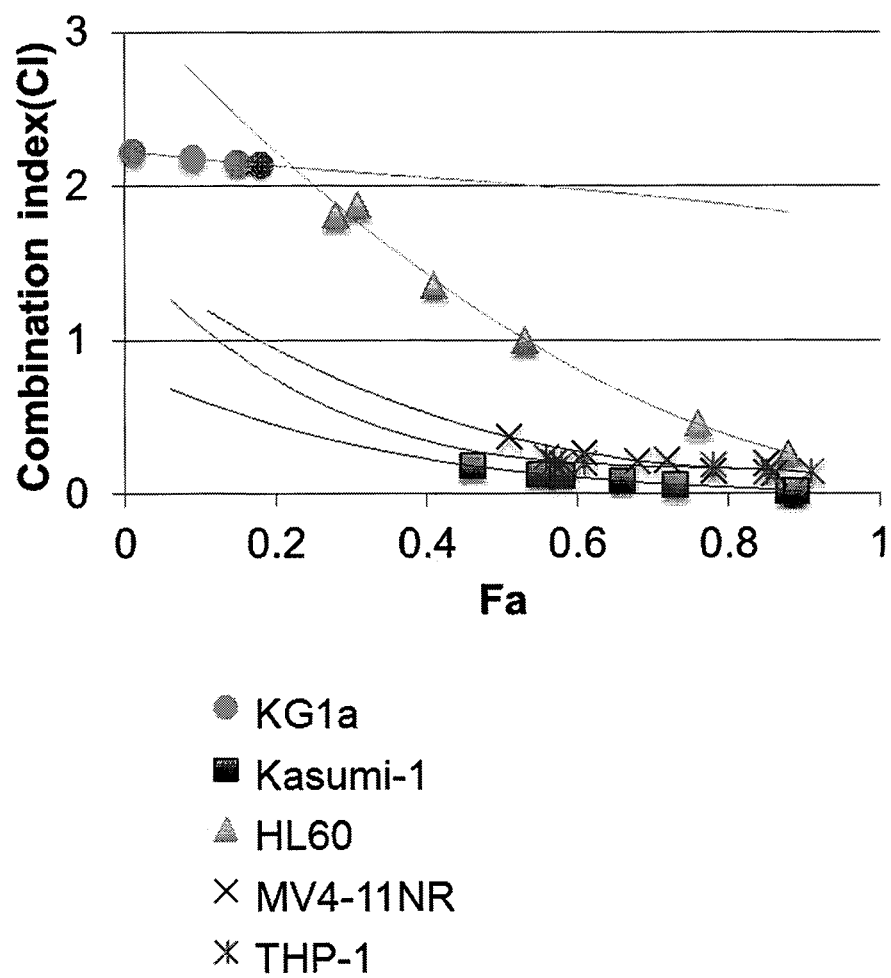
[FIG. 8]

| | | Control | Chb-M' 1 mg/kg | Chb-M' 3.2 mg/kg | Chb-M' 10 mg/kg |
|---|---|---|---|---|---|
| RBC | (10⁶/μL) | 8.272±0.568 | 8.108±0.216 | 8.156±0.363 | 8.104±0.548 |
| Hb | (g/dL) | 13.50±0.69 | 13.34±0.36 | 13.16±0.76 | 13.08±0.54 |
| Ht | (%) | 42.16±2.29 | 41.66±1.28 | 41.72±1.77 | 41.56±1.27 |
| MCV | (fL) | 50.98±1.08 | 51.38±0.79 | 51.20±1.00 | 51.42±1.93 |
| MCH | (pg) | 16.36±0.50 | 16.44±0.43 | 16.16±0.67 | 16.18±0.50 |
| MCHC | (g/dL) | 32.08±0.36 | 32.04±0.90 | 31.54±0.70 | 31.44±0.44 |
| Ret. | (%) | 2.36±0.45 | 2.66±0.24 | 3.38±0.36 | 3.06±0.67 |
| Plat. | (10³/μL) | 1008.0±97.2 | 963.6±66.2 | 850.0±61.1 | 733.0±89.2 |
| WBC | (10³/μL) | 3.066±1.077 | 2.428±0.613 | 3.124±0.651 | 1.892±0.860 |
| Neutro. | (10³/μL) | 0.526±0.236 | 0.380±0.182 | 0.558±0.287 | 0.320±0.131 |
| Lymph. | (10³/μL) | 2.384±0.936 | 1.878±0.536 | 2.385±0.412 | 1.440±0.715 |
| Mono. | (10³/μL) | 0.058±0.022 | 0.044±0.018 | 0.050±0.029 | 0.036±0.023 |
| Eosino. | (10³/μL) | 0.112±0.027 | 0.118±0.053 | 0.144±0.049 | 0.092±0.028 |
| Baso. | (10³/μL) | 0.002±0.004 | 0.000±0.000 | 0.000±0.000 | 0.000±0.000 |
| LUC | (10³/μL) | 0.006±0.005 | 0.004±0.005 | 0.014±0.005 | 0.004±0.005 |
| Neutro. | (%) | 17.84±5.45 | 15.58±5.98 | 17.16±5.35 | 17.46±3.81 |
| Lymph. | (%) | 75.22±8.68 | 77.30±7.26 | 75.76±4.01 | 75.10±4.27 |
| Mono. | (%) | 2.04±0.97 | 1.94±0.69 | 1.76±1.17 | 1.76±0.74 |
| Eosino. | (%) | 4.62±3.37 | 4.96±2.18 | 4.76±1.77 | 5.38±1.85 |
| Baso. | (%) | 0.10±0.00 | 0.10±0.00 | 0.12±0.08 | 0.10±0.12 |
| LUC | (%) | 0.22±0.04 | 0.18±0.08 | 0.42±0.22 | 0.22±0.08 | b

| | | Control | Chb-M' 1 mg/kg | Chb-M' 3.2 mg/kg | Chb-M' 10 mg/kg |
|---|---|---|---|---|---|
| AST | (IU/L) | 45.6±5.9 | 54.4±11.1 | 46.2±4.4 | 48.2±4.0 |
| ALT | (IU/L) | 22.6±4.3 | 35.2±17.8 | 22.4±2.1 | 31.2±10.1 |
| ALP | (IU/L) | 245.4±43.9 | 224.2±53.7 | 222.0±39.3 | 194.6±41.8 |
| CK | (IU/L) | 48.6±11.4 | 53.0±24.2 | 45.4±31.5 | 48.0±14.0 |
| T-Bil | (mg/dL) | 0.072±0.008 | 0.062±0.028 | 0.068±0.008 | 0.064±0.005 |
| TP | (g/dL) | 4.48±0.22 | 4.48±0.13 | 4.62±0.15 | 4.56±0.09 |
| TG | (mg/dL) | 78.0±36.6 | 81.4±31.9 | 79.0±22.7 | 85.0±39.9 |
| T-cho | (mg/dL) | 92.2±8.2 | 84.6±20.2 | 83.8±22.2 | 81.4±13.5 |
| Glucose | (mg/dL) | 231.8±27.8 | 218.2±15.3 | 212.2±15.0 | 216.4±12.5 |
| UN | (mg/dL) | 19.00±3.92 | 19.02±5.39 | 18.16±3.04 | 19.00±1.19 |
| Cre | (mg/dL) | 0.104±0.009 | 0.112±0.020 | 0.108±0.008 | 0.112±0.004 |
| IP | (mg/dL) | 3.294±0.707 | 3.904±0.985 | 3.954±1.224 | 3.032±0.826 |
| Ca | (mg/dL) | 8.60±0.19 | 8.74±0.21 | 8.70±0.31 | 8.46±0.41 |
| Na | (mEq/L) | 150.8±0.8 | 151.8±1.3 | 152.8±1.8 | 152.2±0.8 |
| K | (mEq/L) | 3.58±0.28 | 3.32±0.43 | 3.44±0.23 | 3.34±0.43 |
| Cl | (mEq/L) | 120.4±1.7 | 120.2±1.6 | 121.4±1.7 | 121.0±1.9 |
| Albumin | (g/dL) | 3.12±0.15 | 3.08±0.16 | 3.12±0.08 | 3.16±0.11 |
| Globulin | (g/dL) | 1.36±0.11 | 1.40±0.07 | 1.50±0.12 | 1.40±0.07 | c

| Day | Control | Chb-M' 1 mg/kg | Chb-M' 3.2 mg/kg | Chb-M' 10 mg/kg |
|---|---|---|---|---|
| -1 | 31.56±0.89 | 31.38±1.38 | 31.6±0.68 | 31.52±0.84 |
| 0 | 31.60±1.34 | 31.24±1.61 | 31.62±0.87 | 31.72±1.08 |
| 1 | 31.40±1.48 | 31.00±1.51 | 31.16±1.26 | 31.06±0.93 |
| 2 | 31.34±1.48 | 31.22±1.56 | 31.34±0.84 | 31.58±0.90 |
| 3 | 31.60±1.83 | 31.18±1.56 | 31.94±0.94 | 31.64±0.88 |
| 4 | 31.92±1.89 | 31.06±1.40 | 32.24±1.00 | 31.66±0.65 |
| 5 | 32.10±2.00 | 31.26±1.59 | 31.58±0.97 | 31.62±0.46 |
| 6 | 31.72±2.27 | 31.36±1.56 | 31.34±0.94 | 31.50±0.80 |
| 7 | 31.32±2.07 | 30.94±1.44 | 31.60±0.73 | 31.54±1.00 |
| 8 | 31.24±2.14 | 31.24±1.64 | 31.70±0.86 | 31.32±0.83 |
| 9 | 31.16±1.99 | 31.48±1.14 | 32.08±0.79 | 31.48±0.45 |

[FIG. 10]
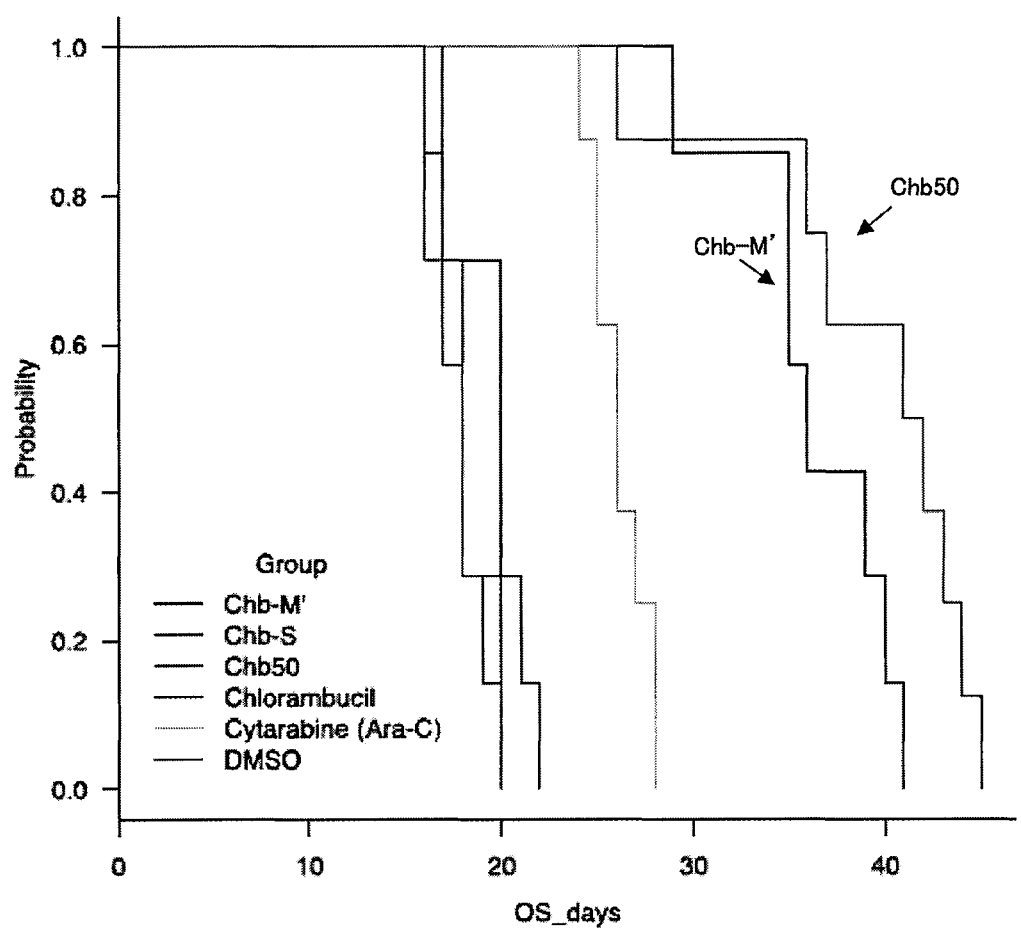

[FIG. 11-1]
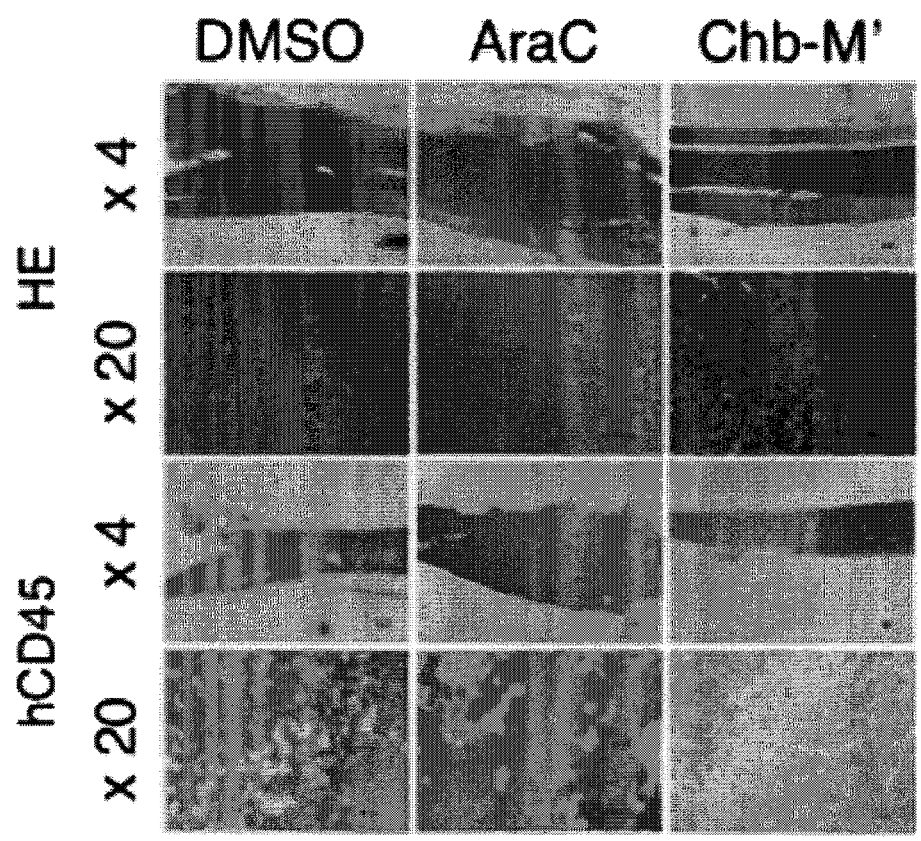

[FIG. 11-2]
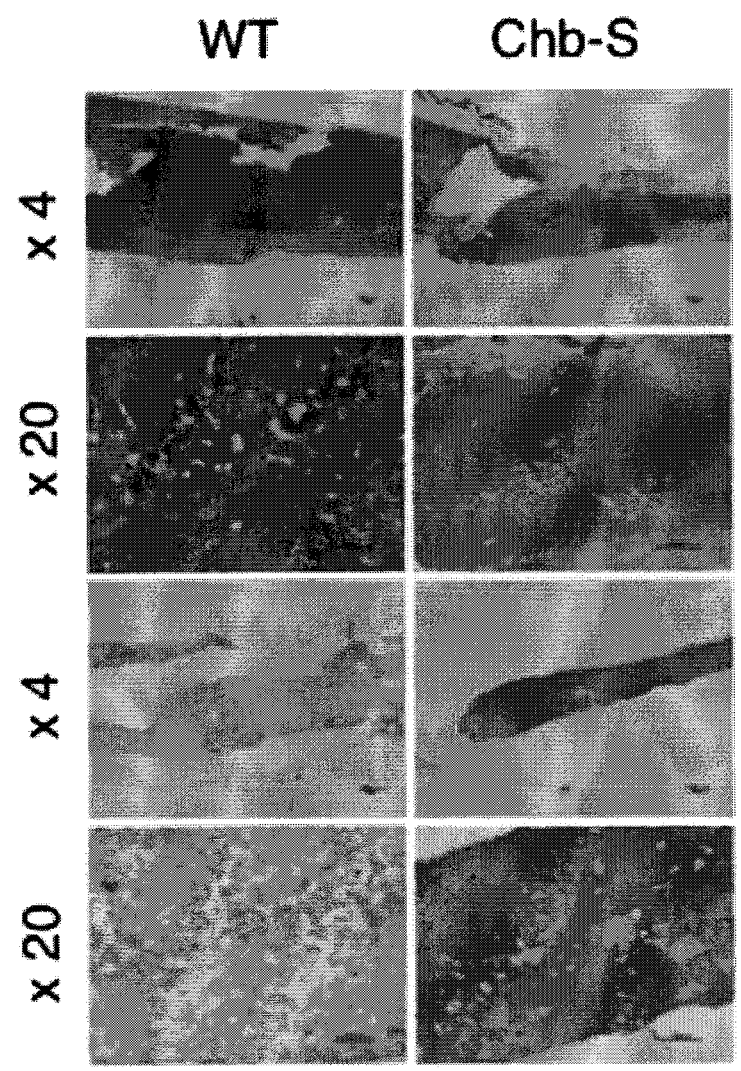

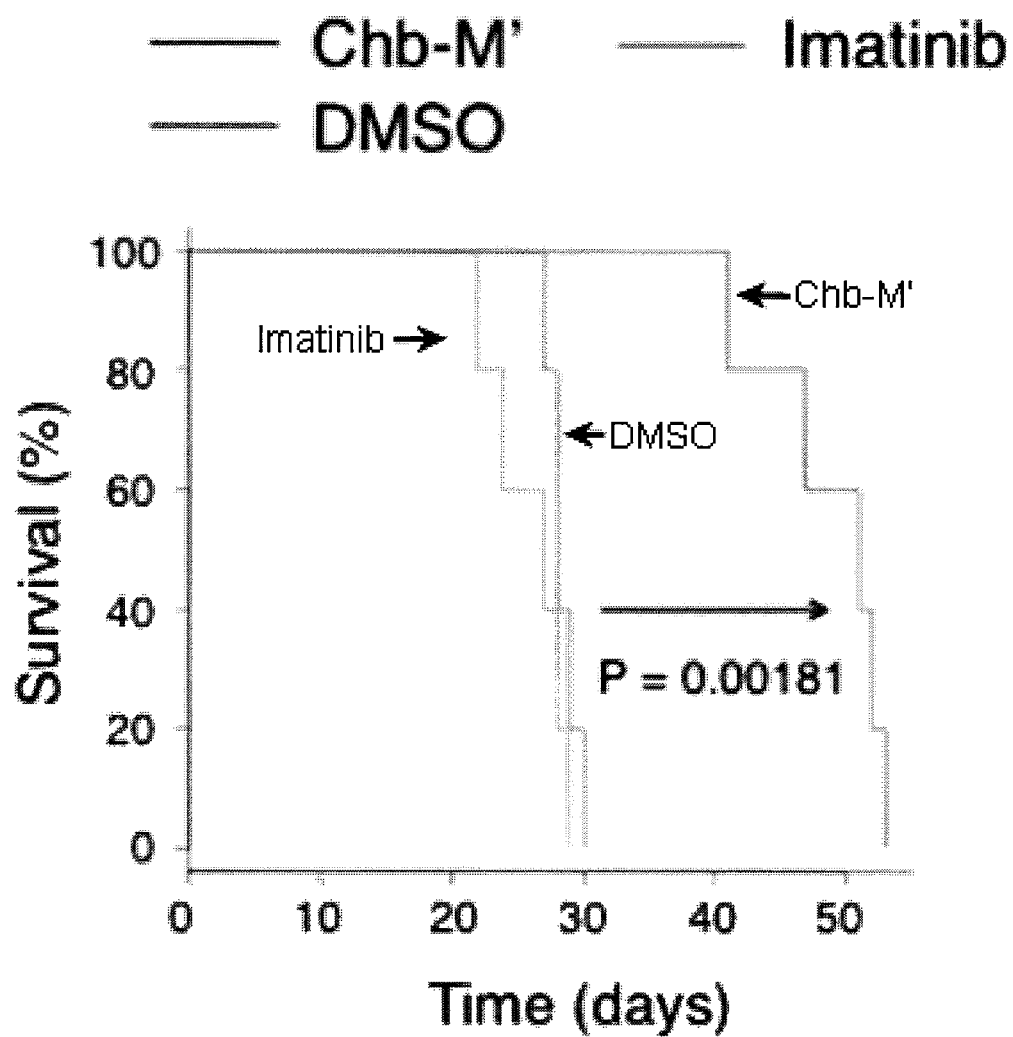
[FIG. 12]

[FIG. 13]
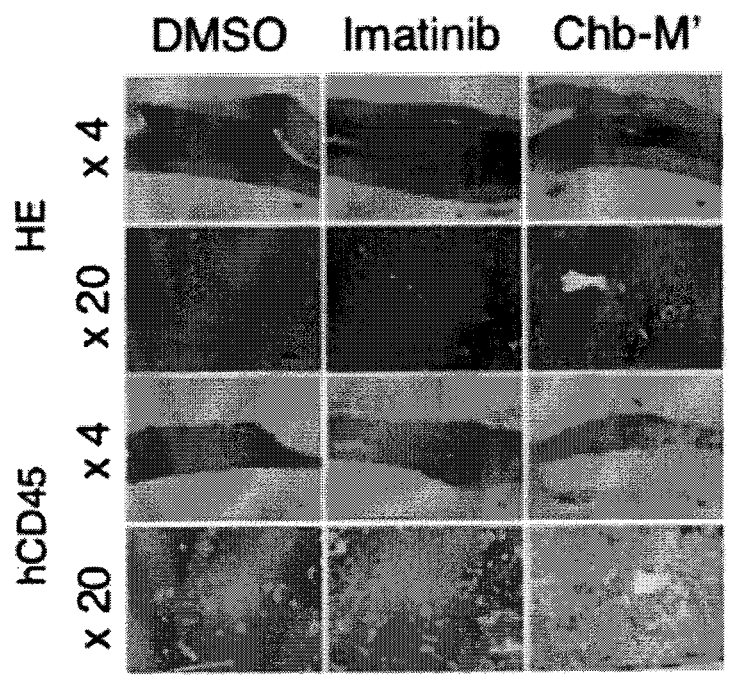
[FIG. 14]
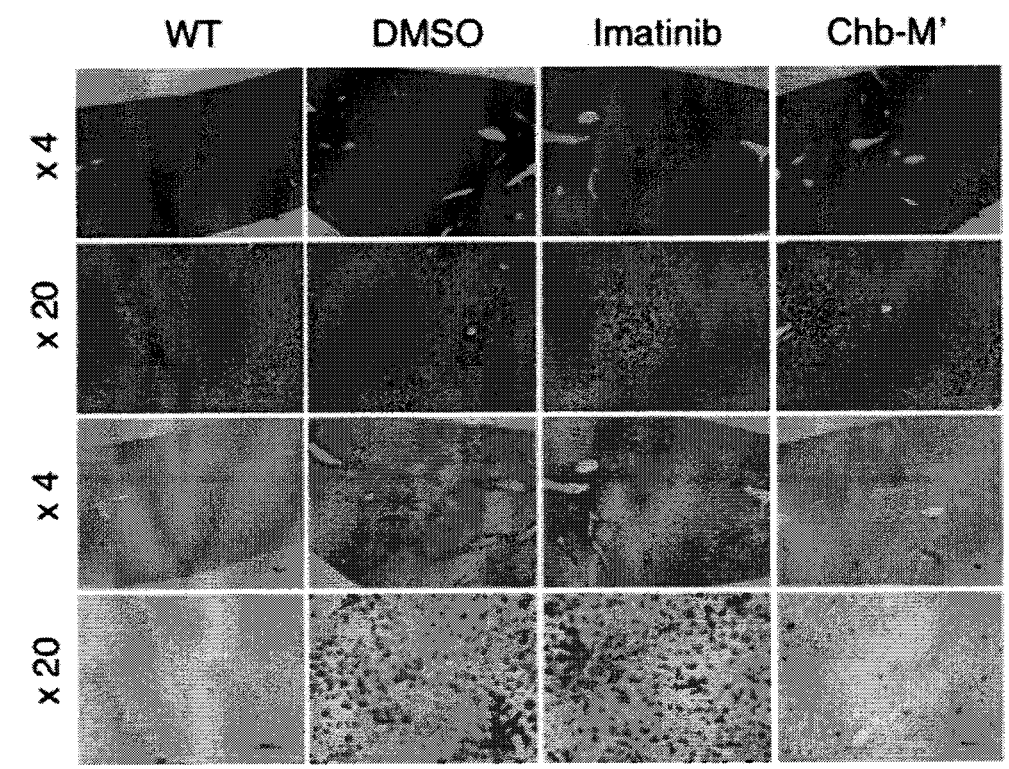

[FIG. 15]
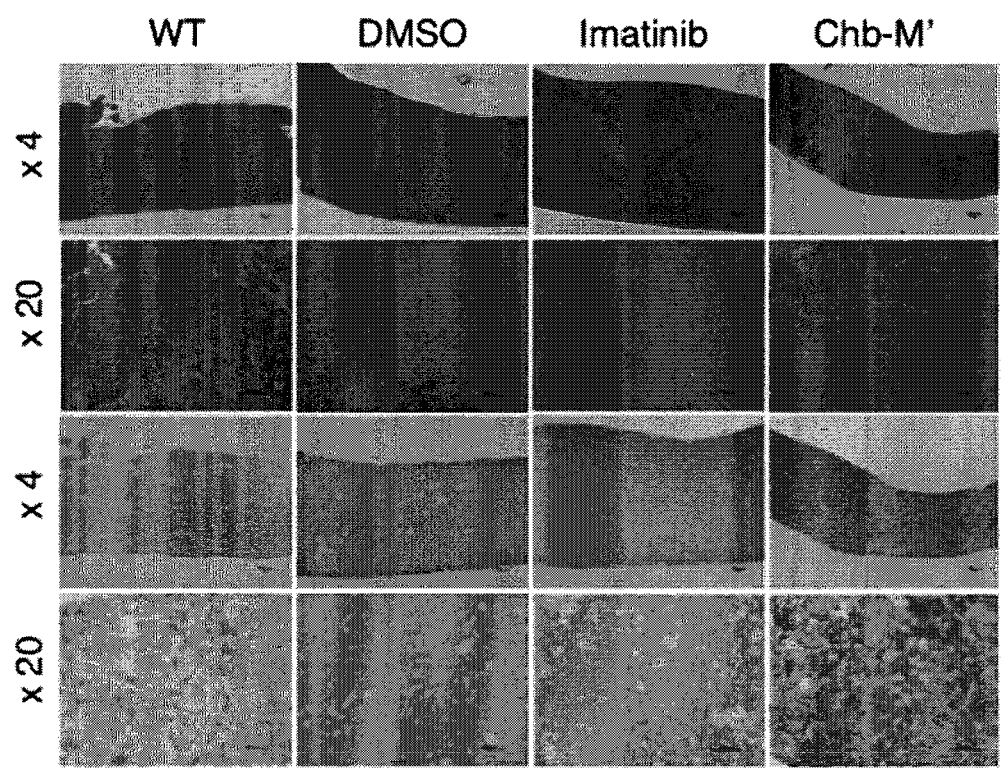

[FIG. 16]
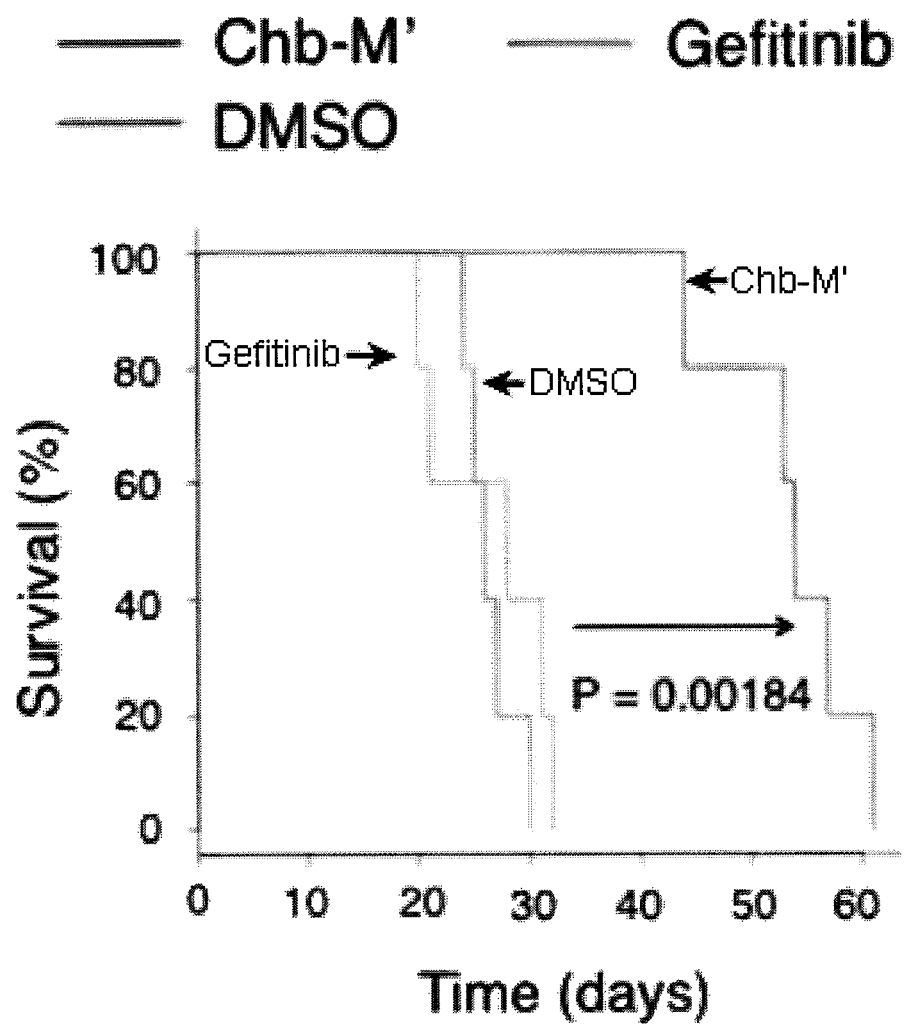

[FIG. 17]
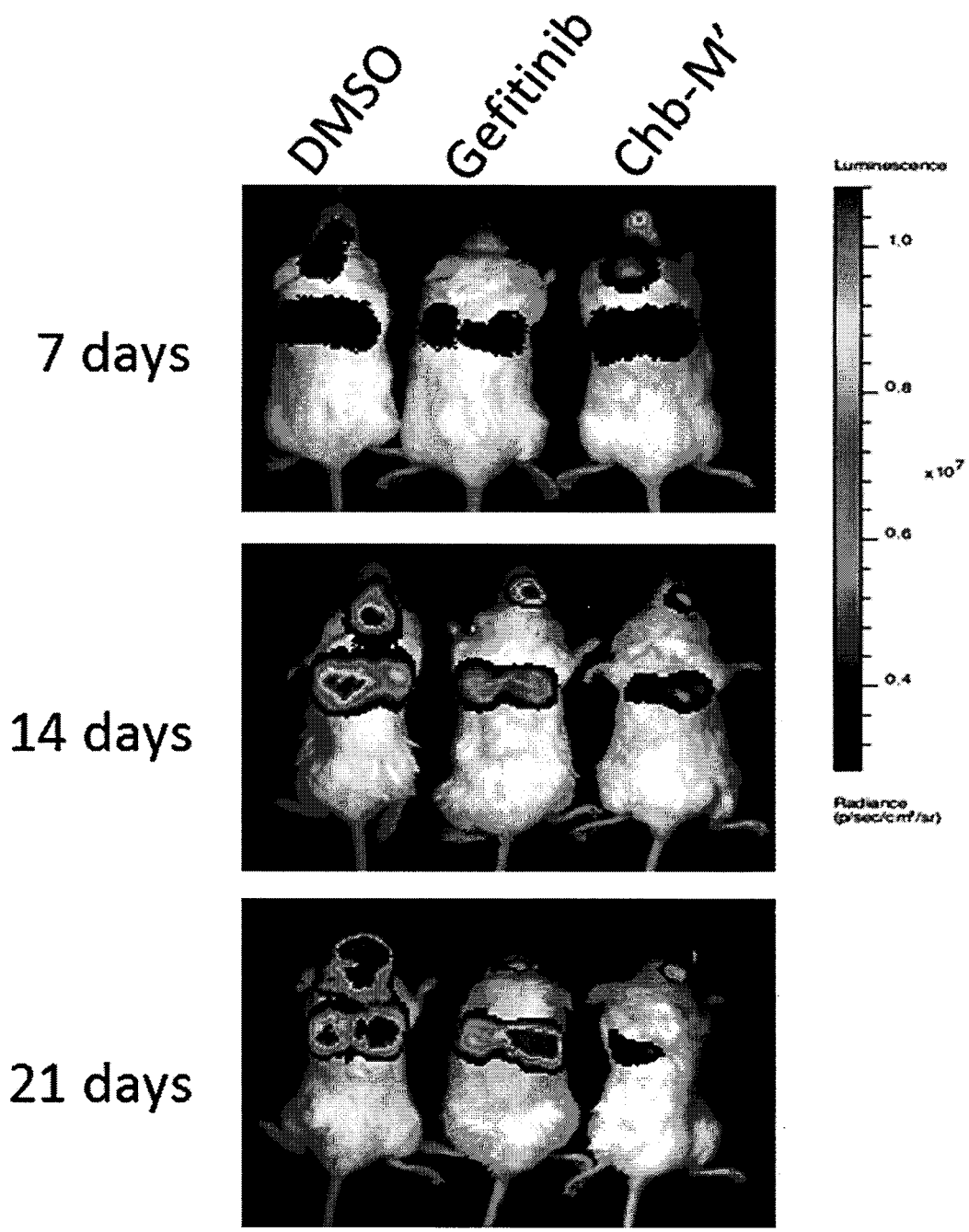

[FIG. 18]
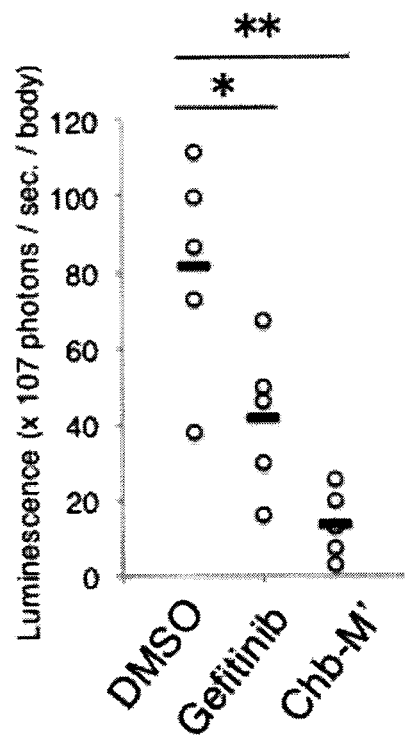
[FIG. 19]
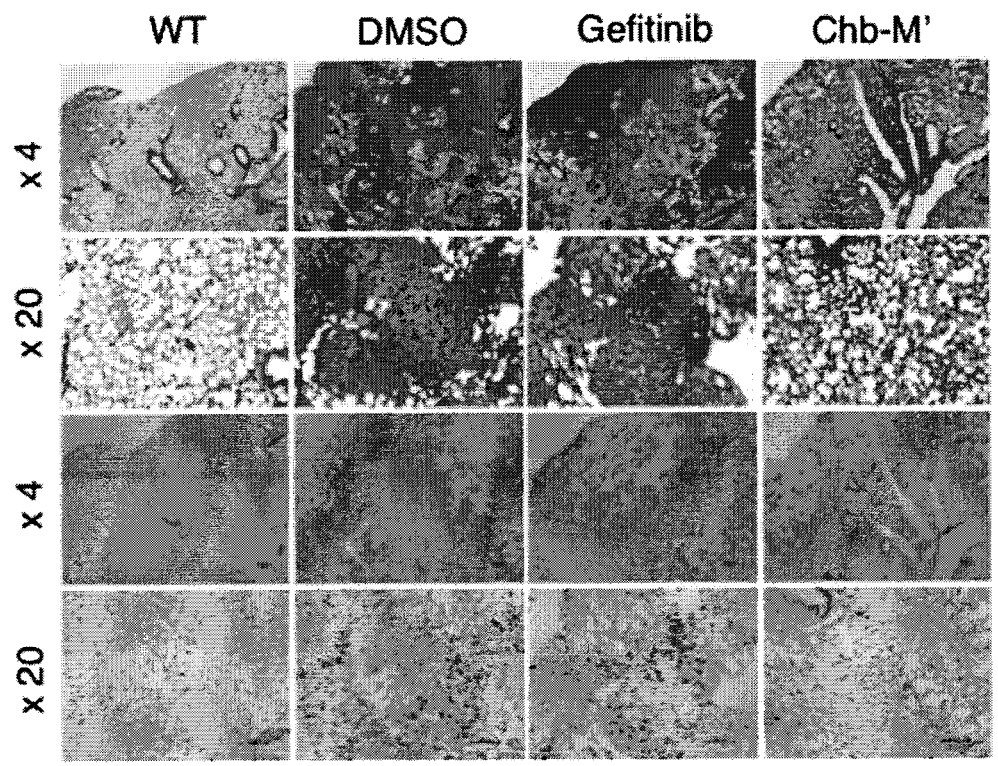

[FIG. 20]
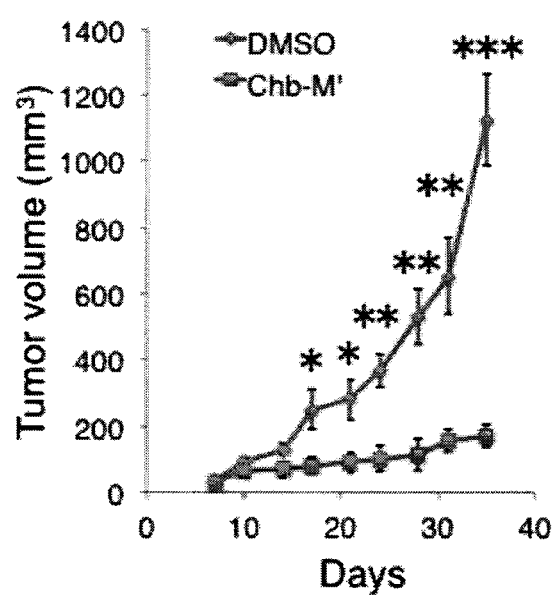

[FIG. 21]
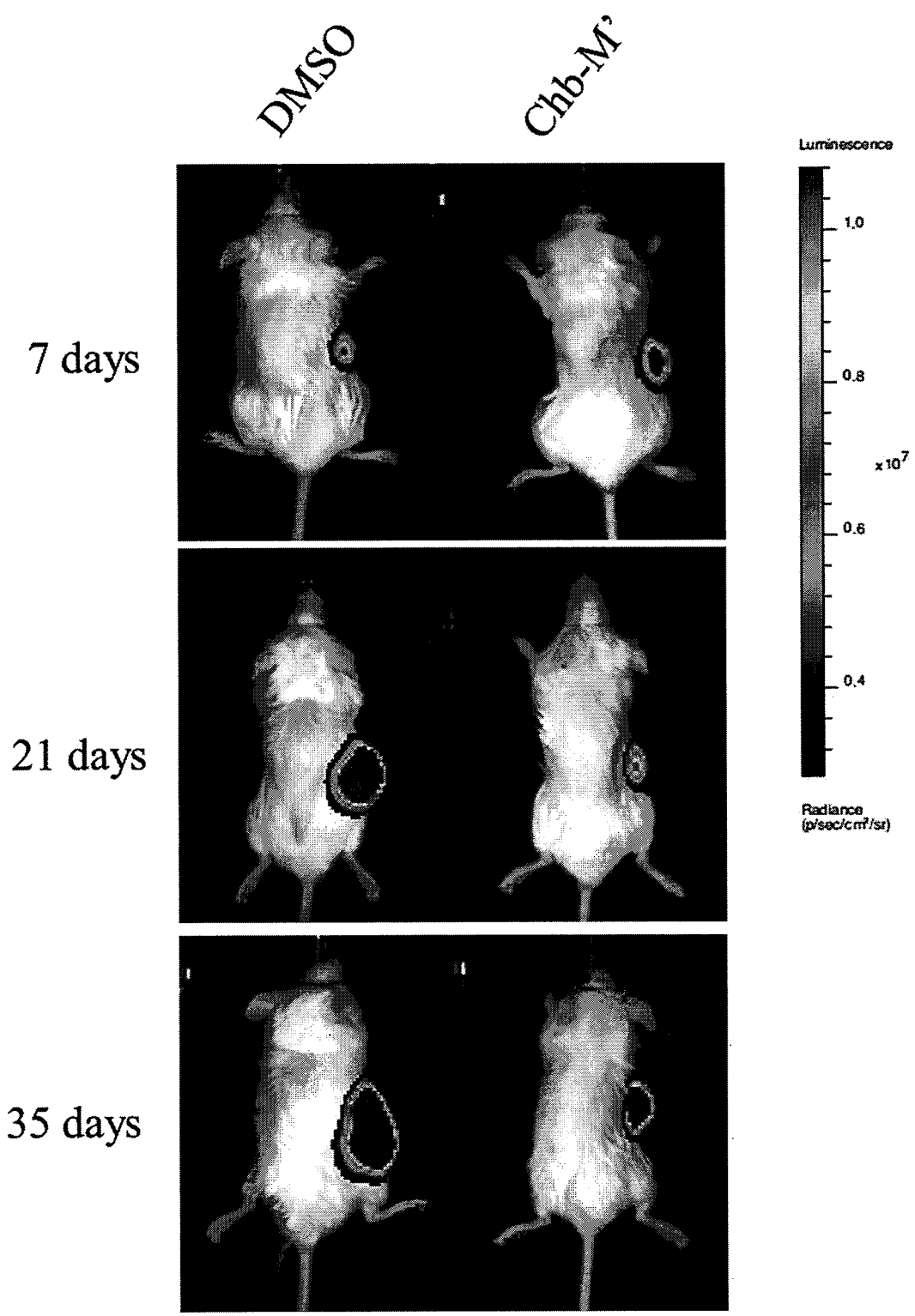

[FIG. 22]
Day 35
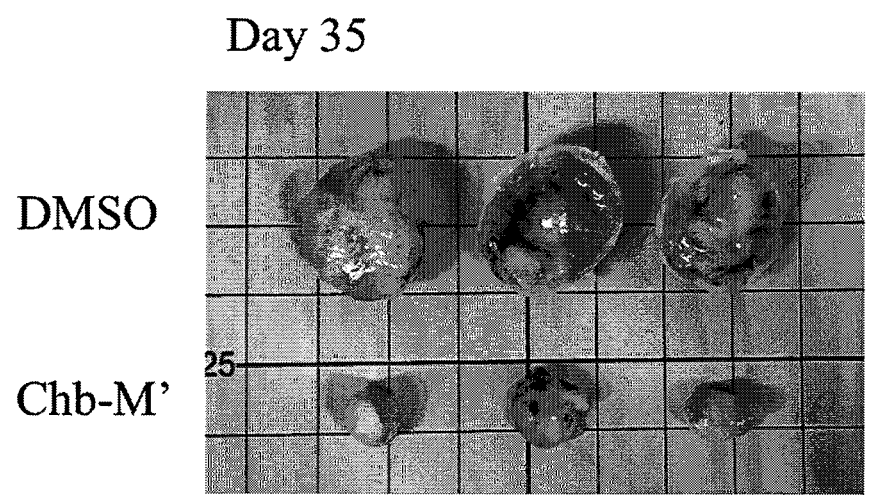
DMSO
Chb-M'
[FIG. 23]
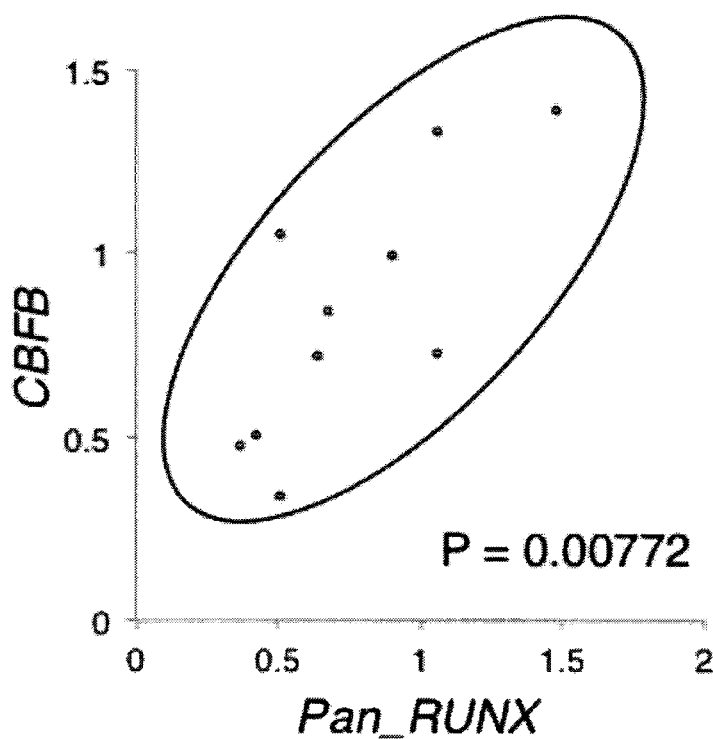

[FIG. 24]
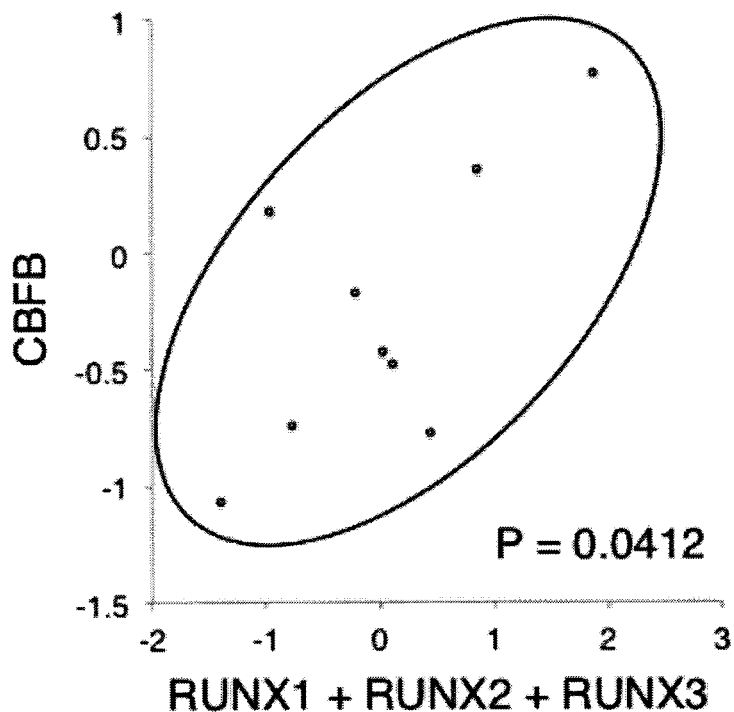
[FIG. 25-1]
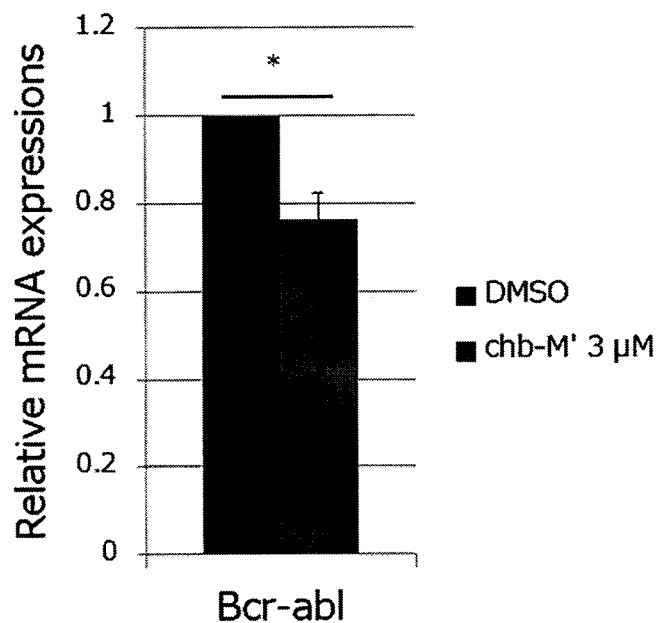

[FIG. 25-2]
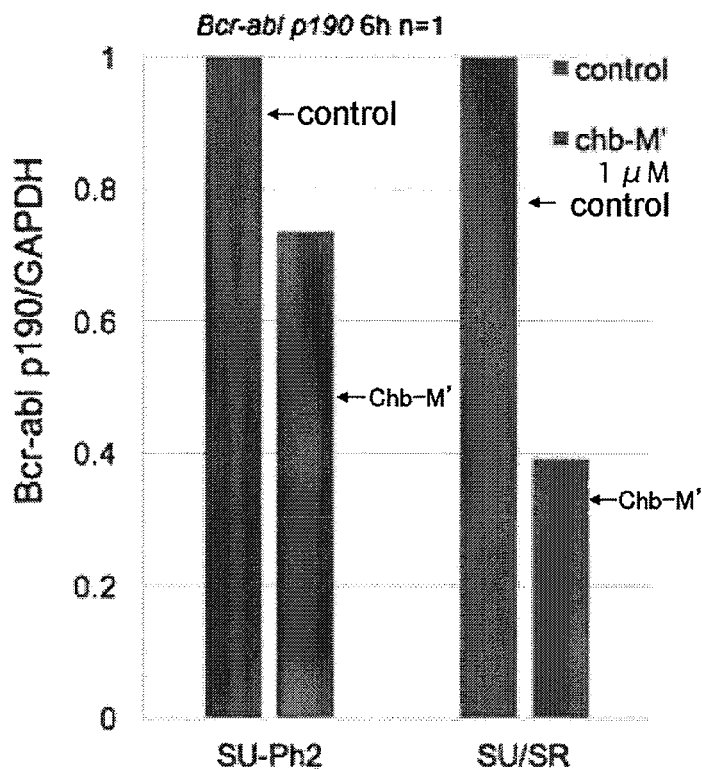
[FIG. 26-1]
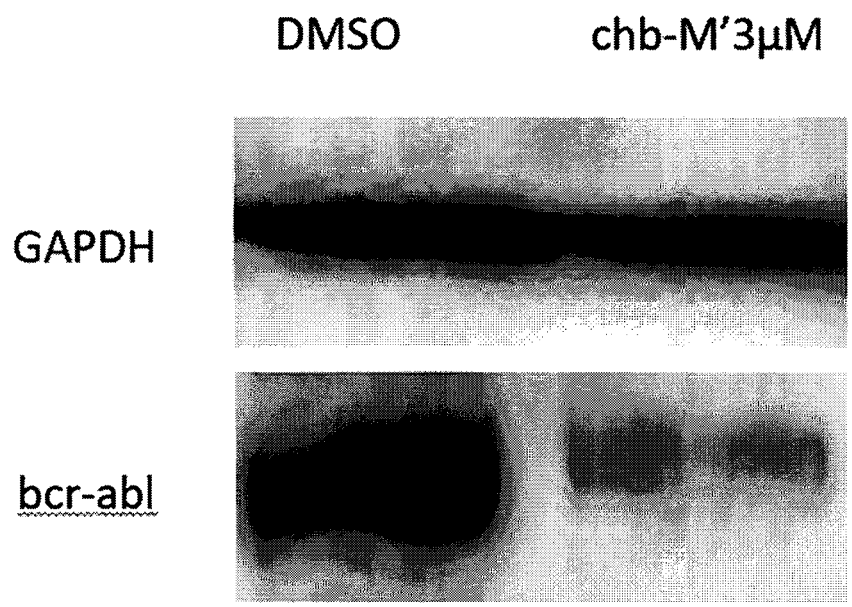

[FIG. 26-2]
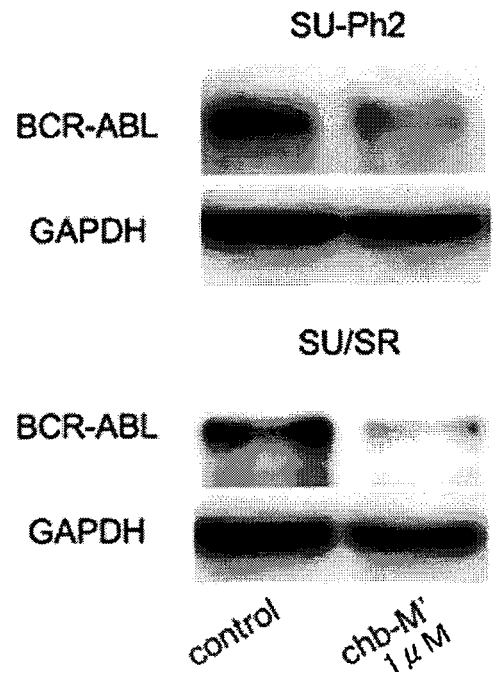
[FIG. 26-3]
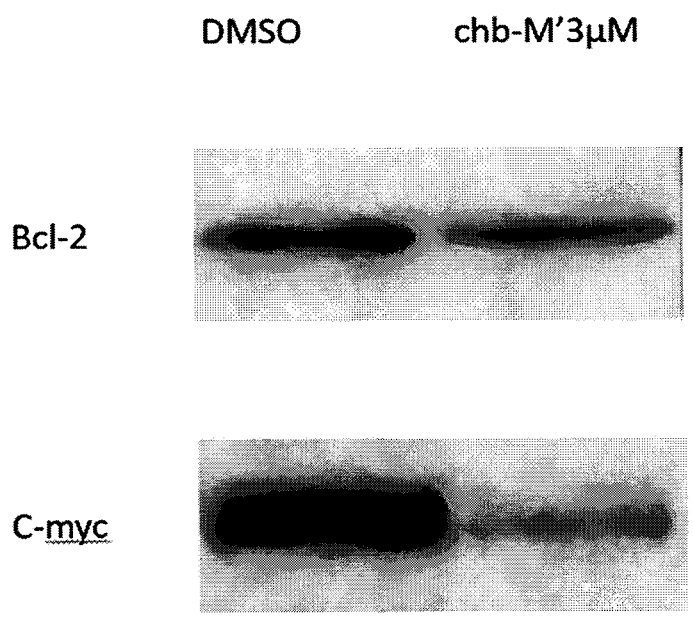

[FIG. 26-4]
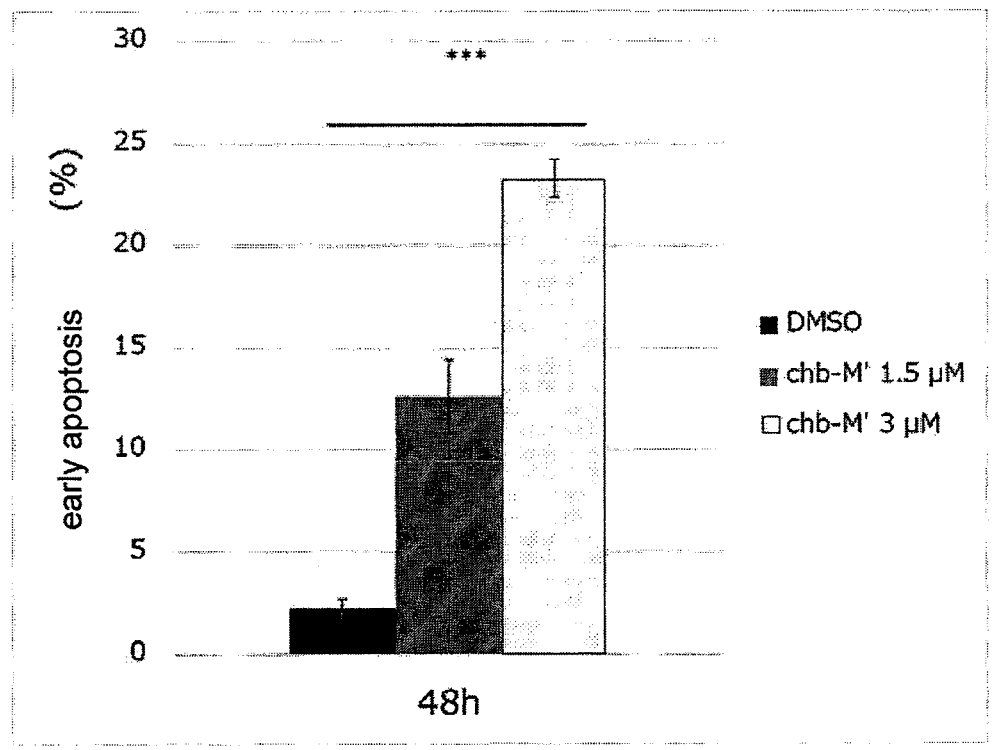
[FIG. 27-1]
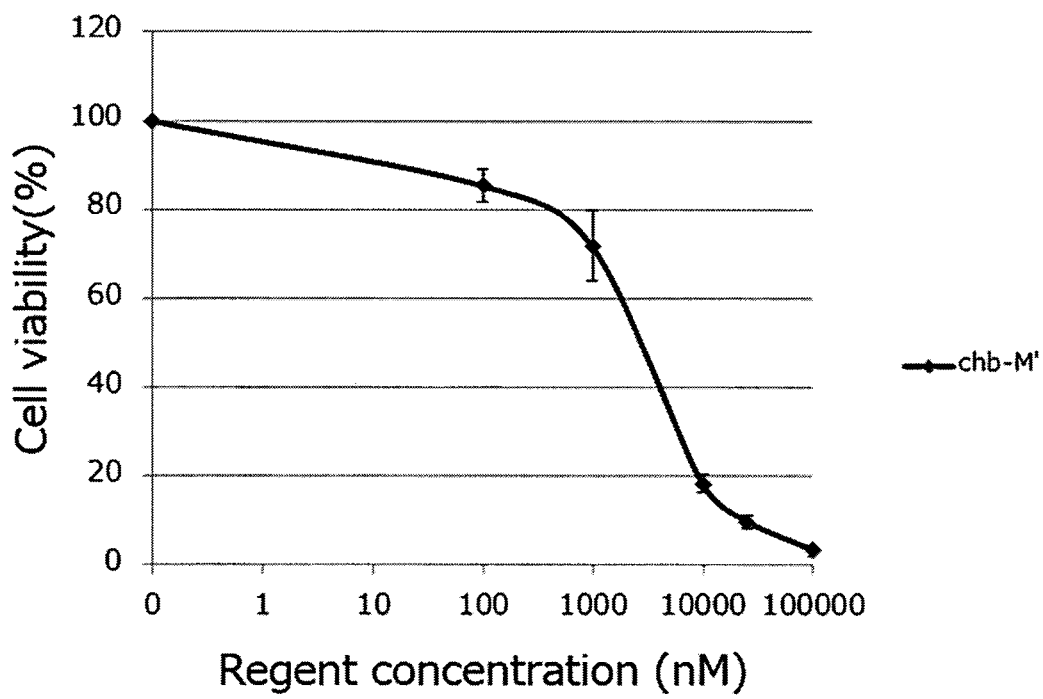

[FIG. 27-2]
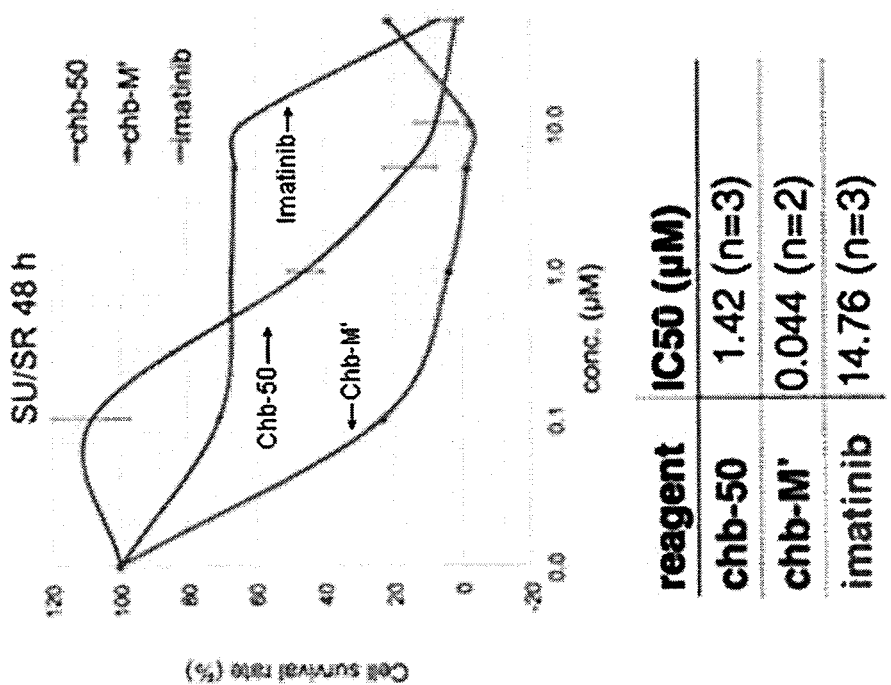
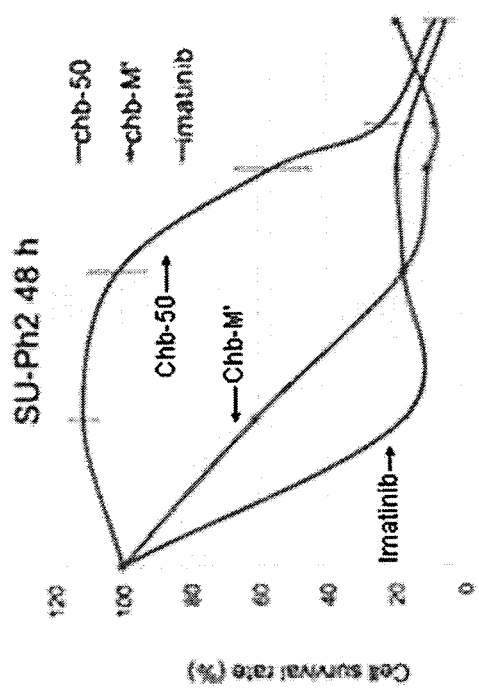
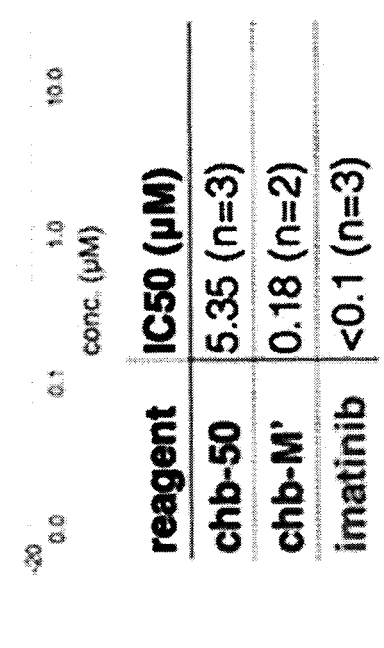

[FIG. 28]
qPCR
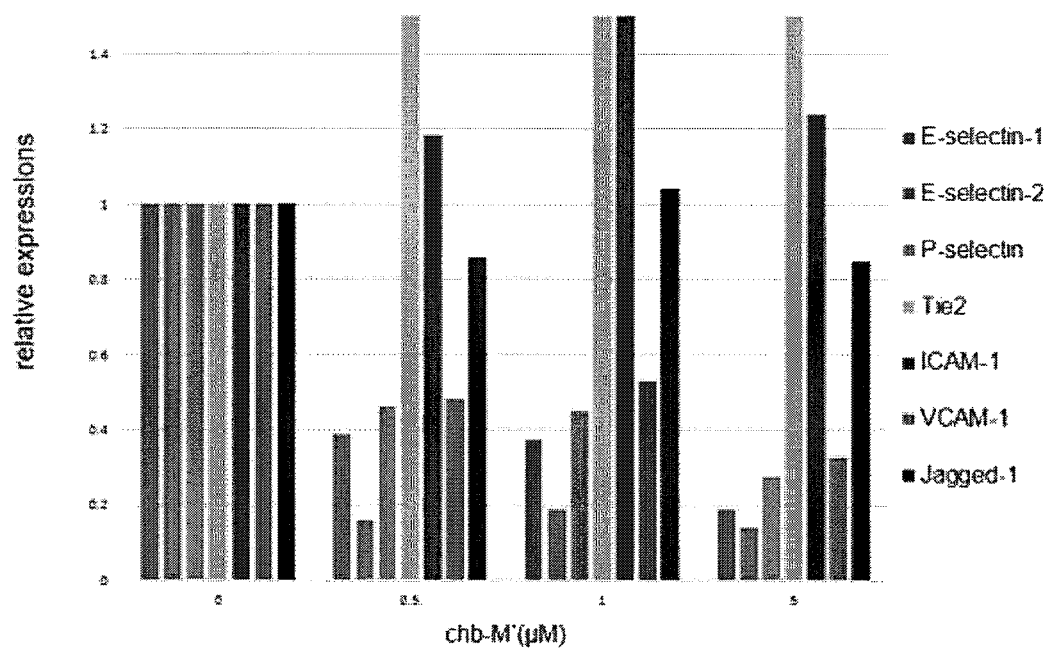

[FIG. 29]
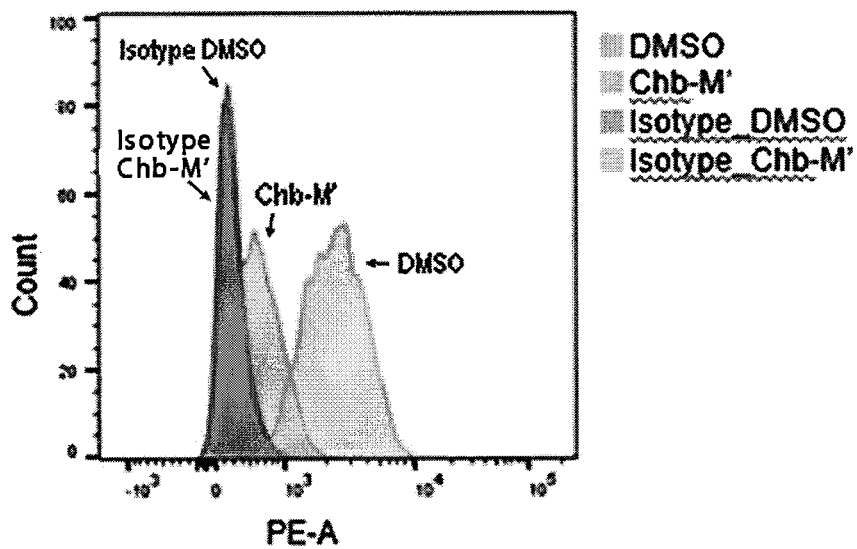
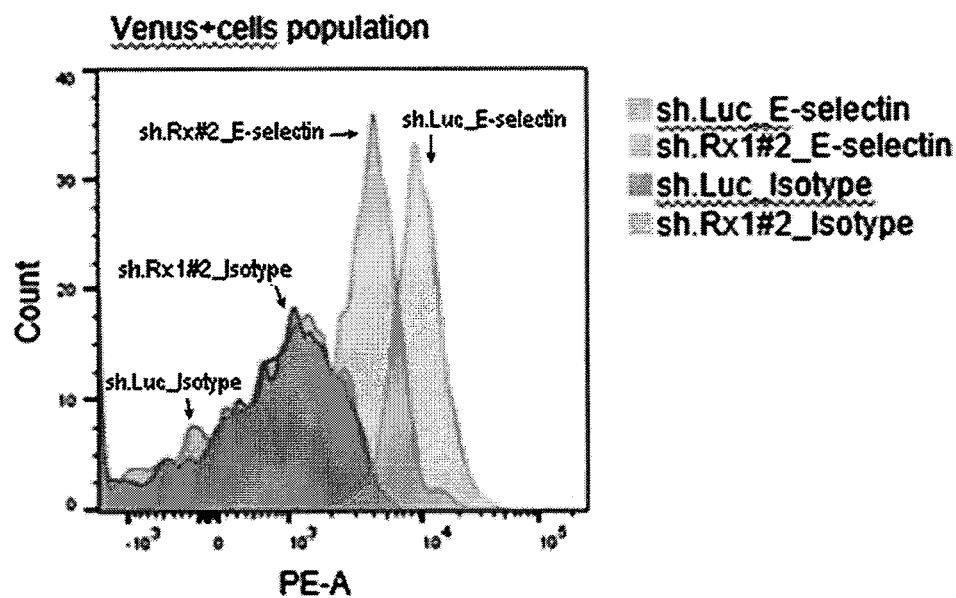

[FIG. 30]
E-selectin expression endothelial cells(Chb-M')
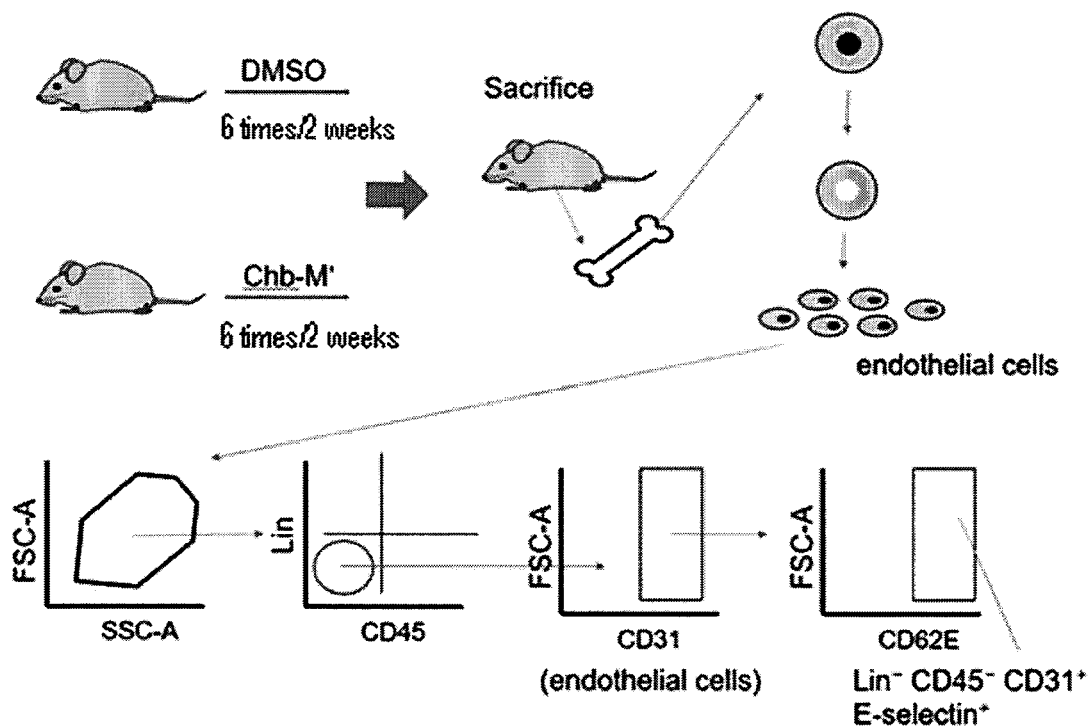

[FIG. 31]
E-selectin expression endothelial cells(Chb-M')
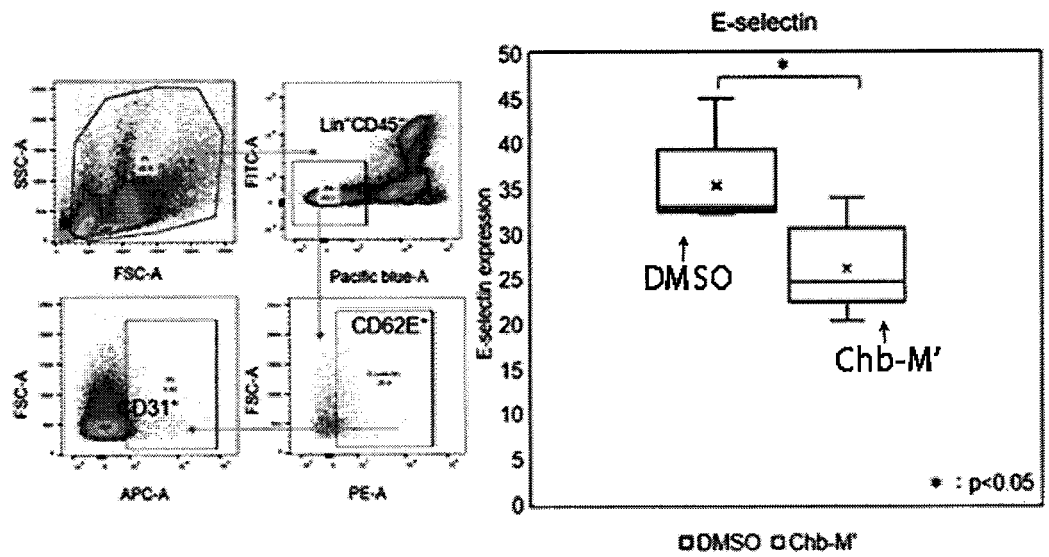
[FIG. 32]
Homing assay
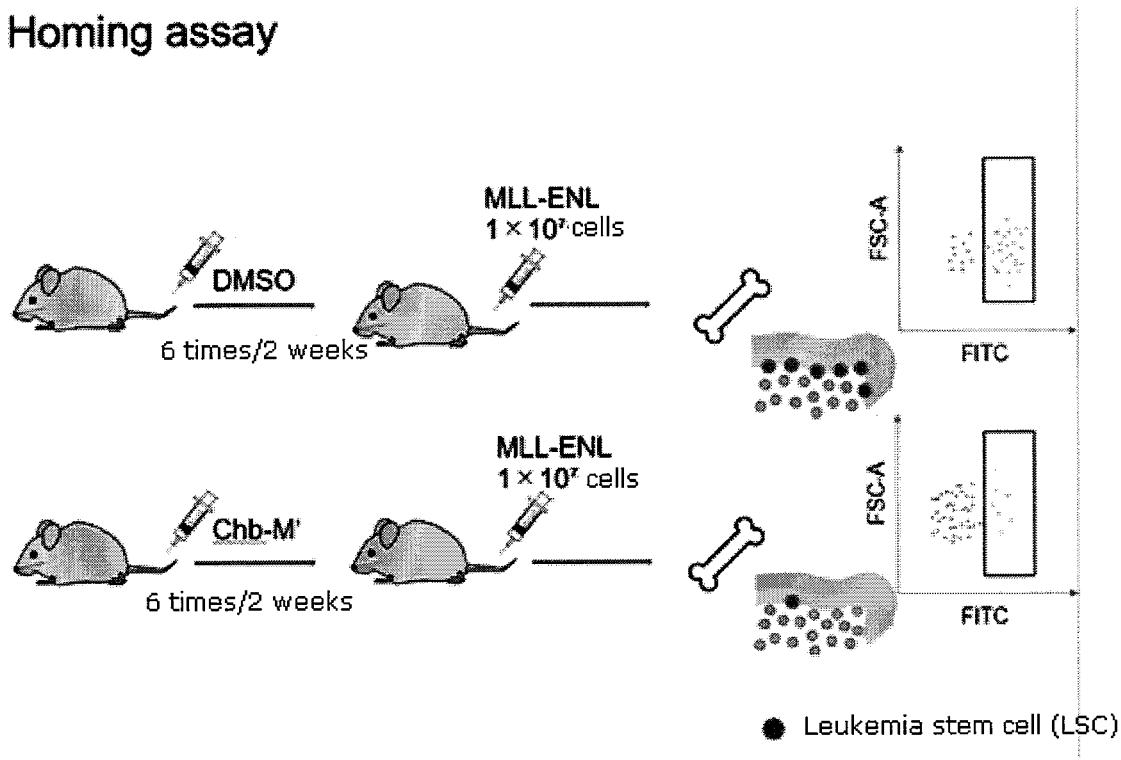

[FIG. 33]
Homing assay
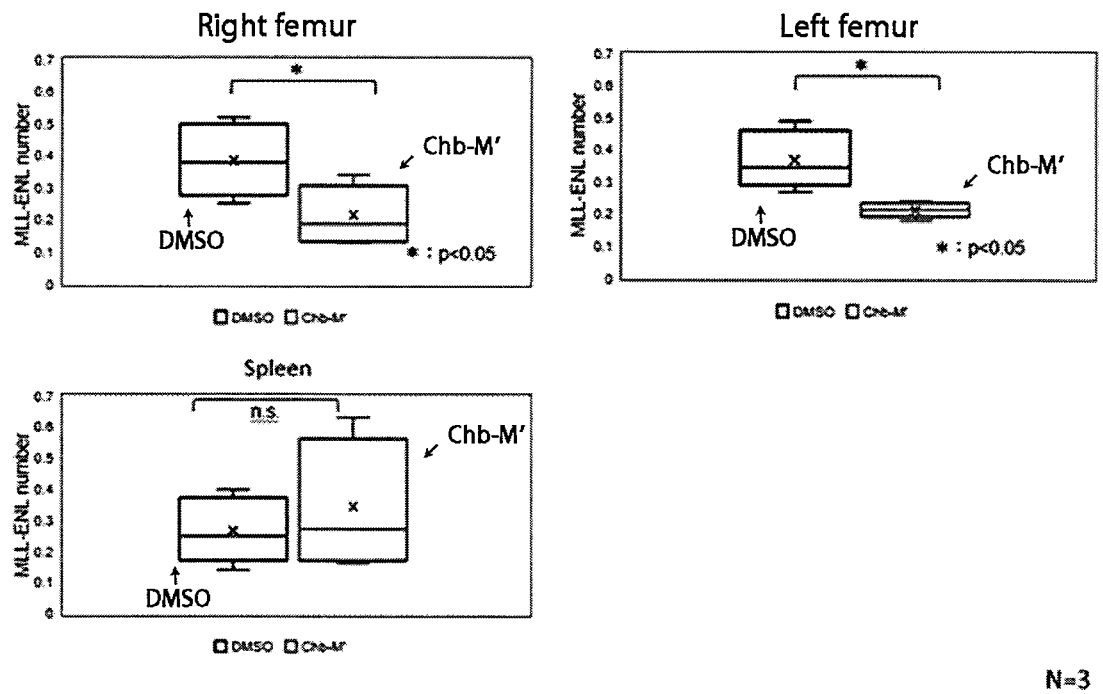
[FIG. 34]
Her2 inhibitor-resistant gastric cancer
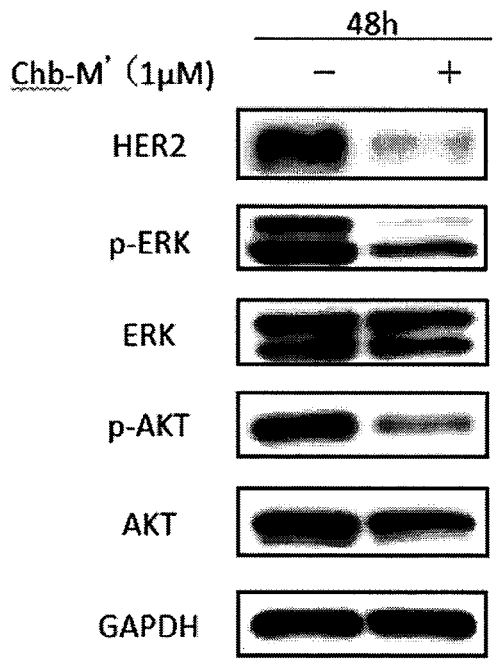

[FIG. 35]
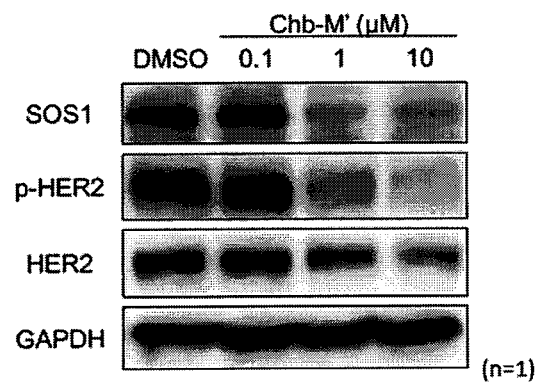
[FIG. 36]
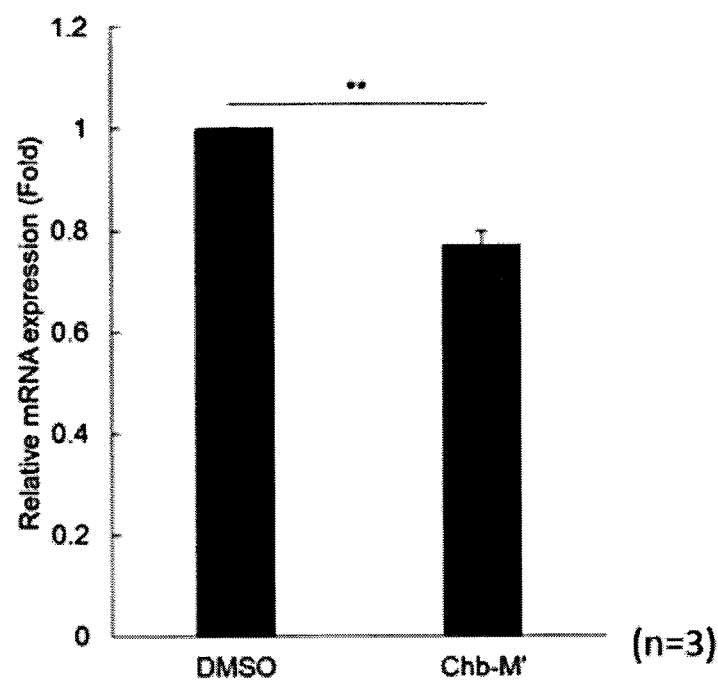

[FIG. 37]
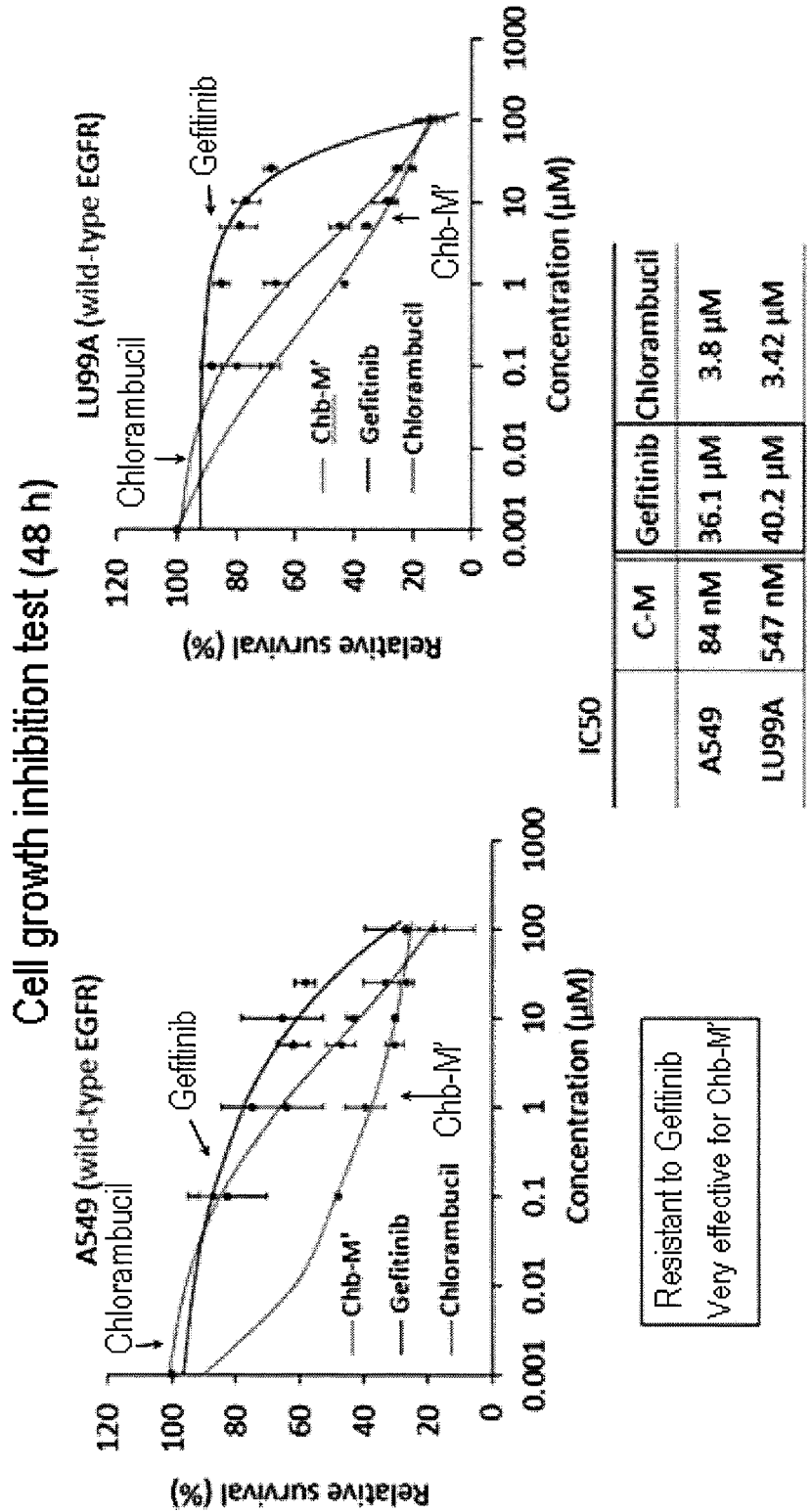

[FIG. 38]
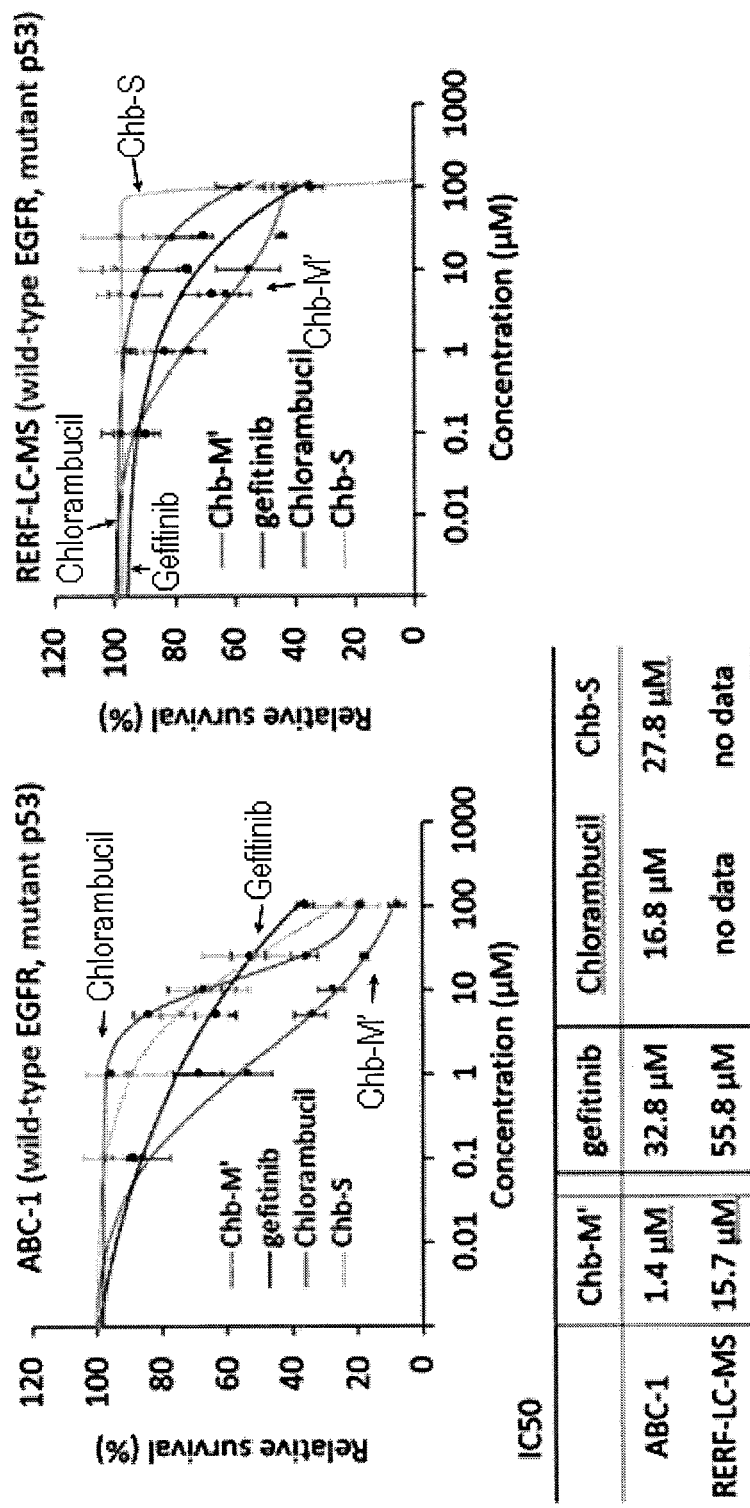

[FIG. 39]
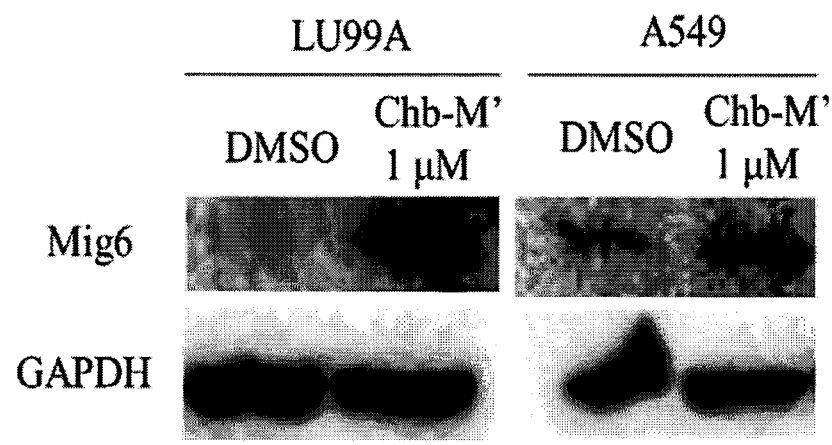
[FIG. 40]
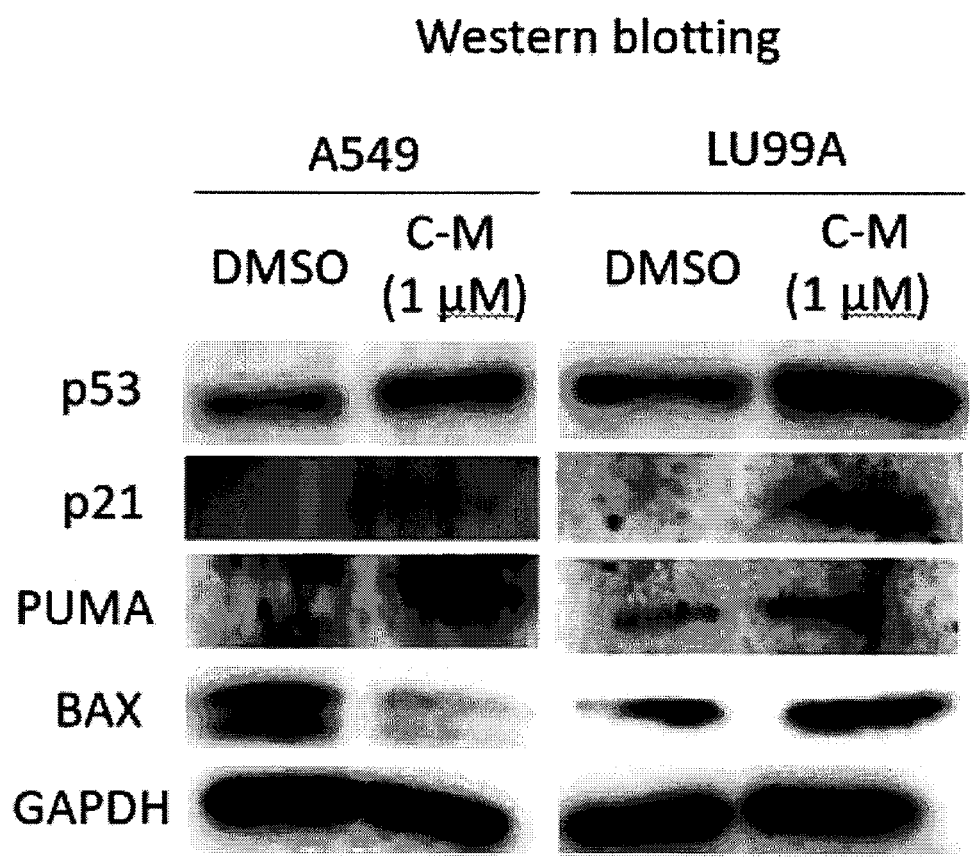

[FIG. 41]
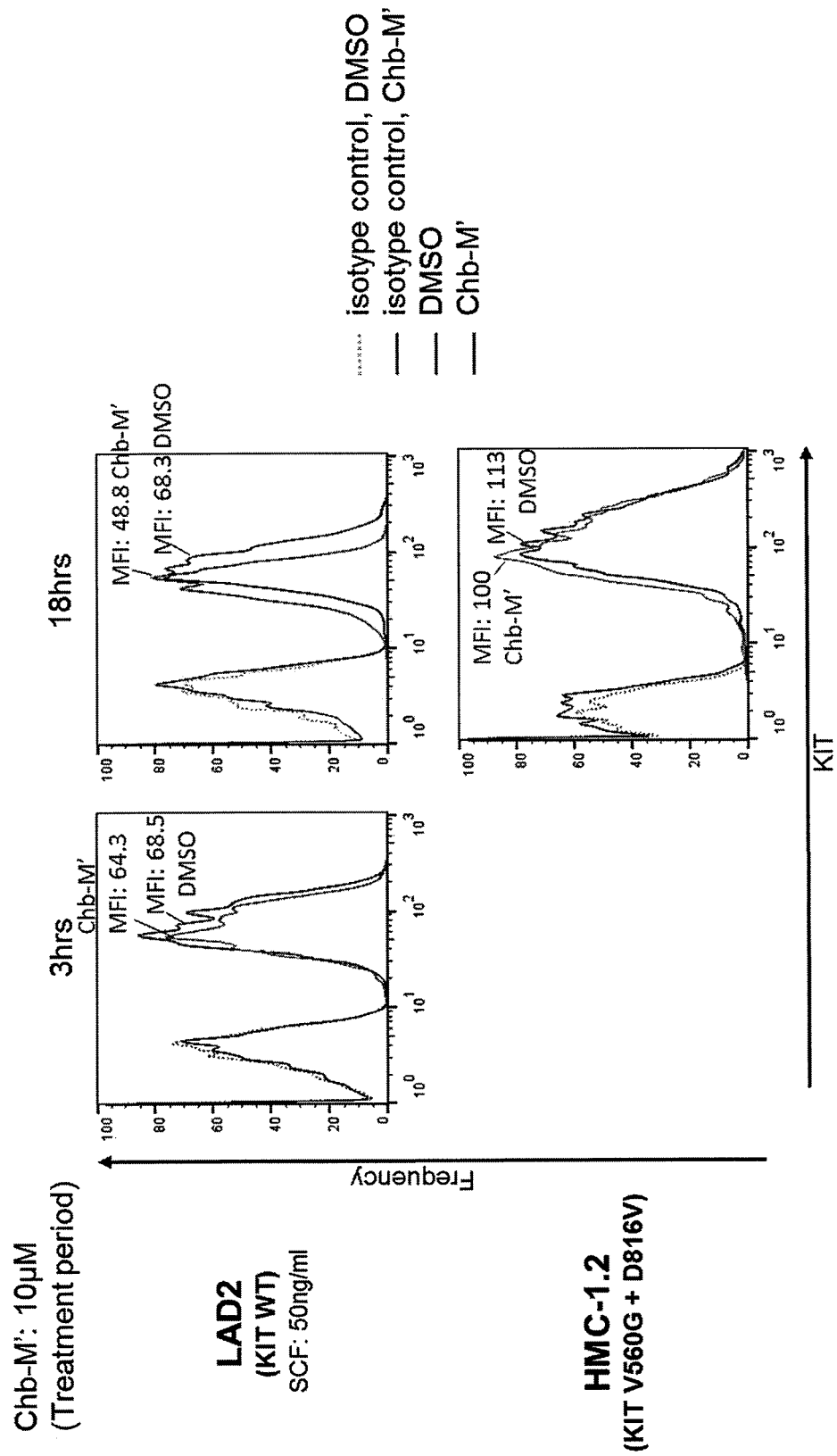

[FIG. 42]
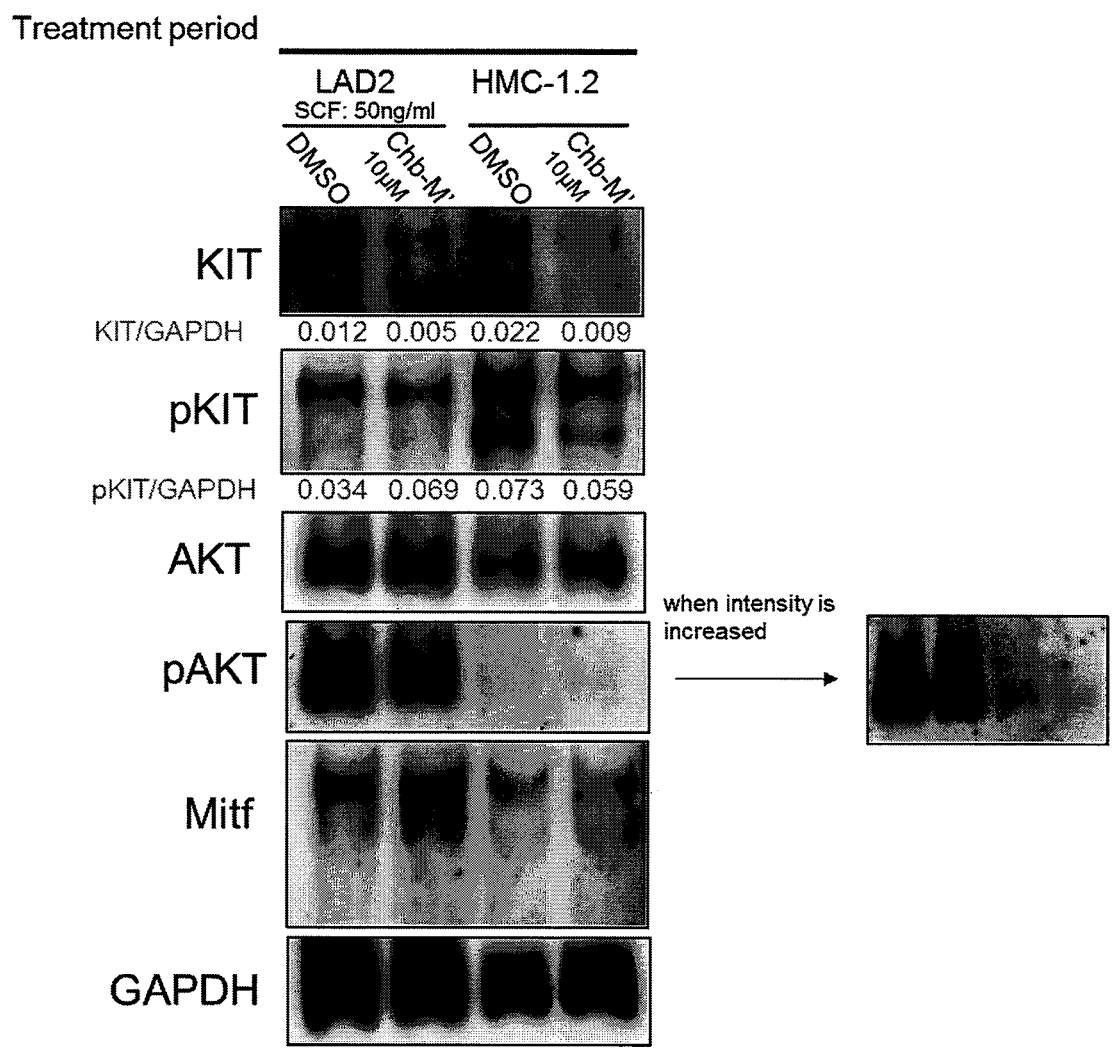

[FIG. 43]
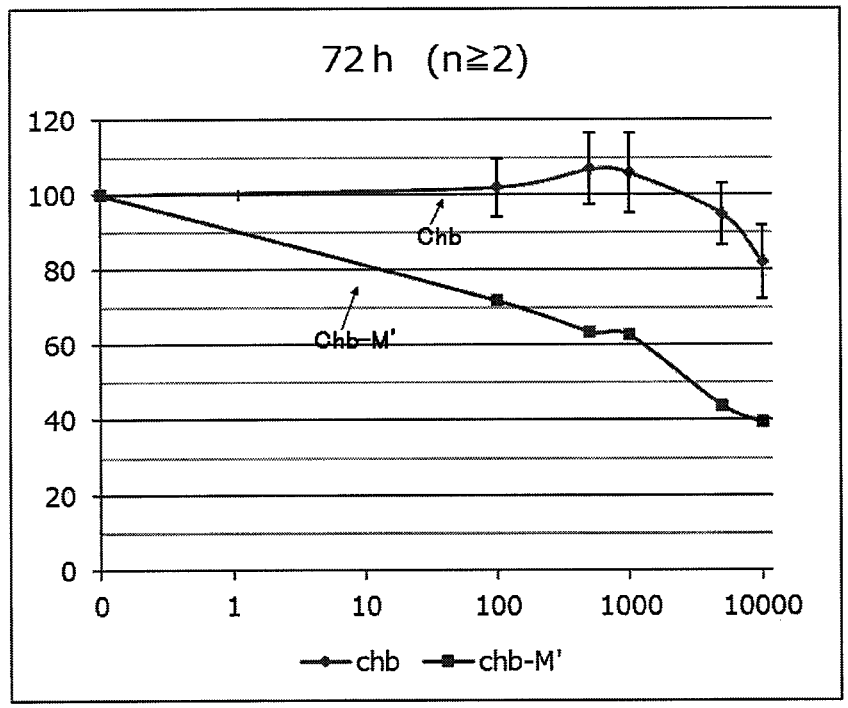
[FIG. 44]
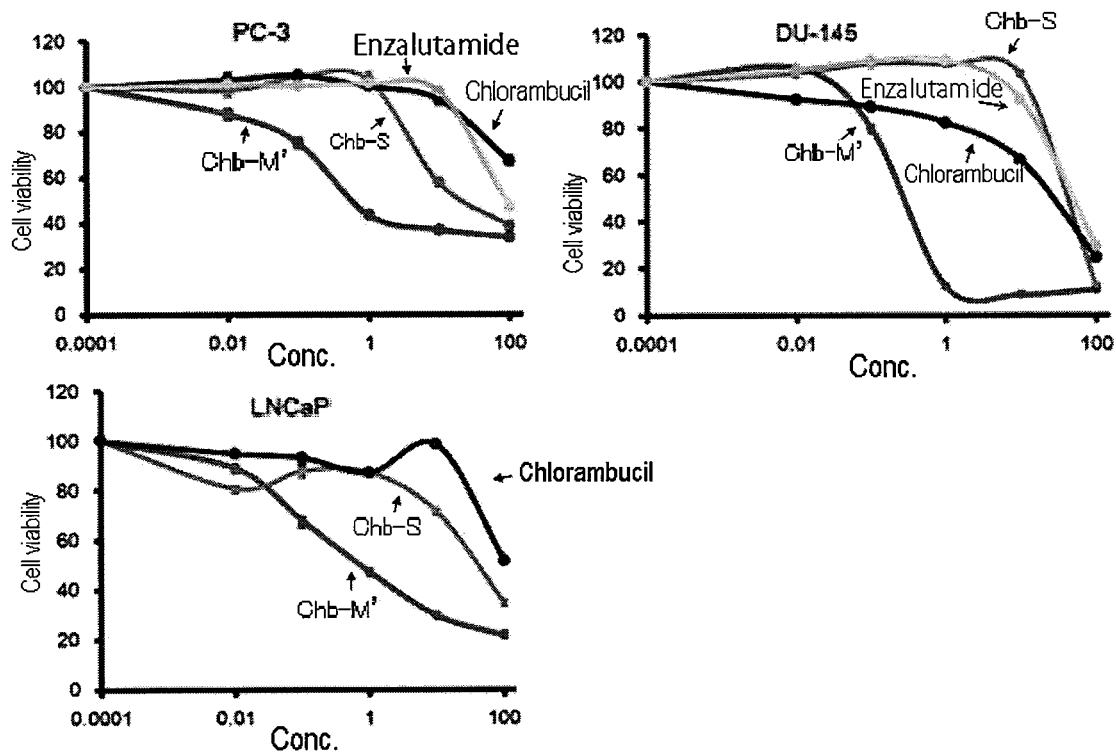

[FIG. 45]
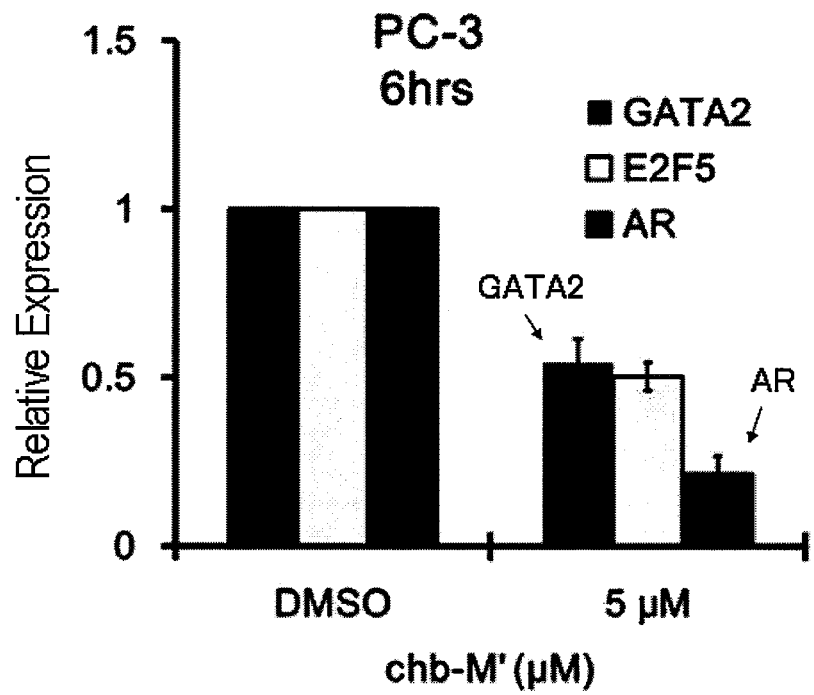
[FIG. 46]
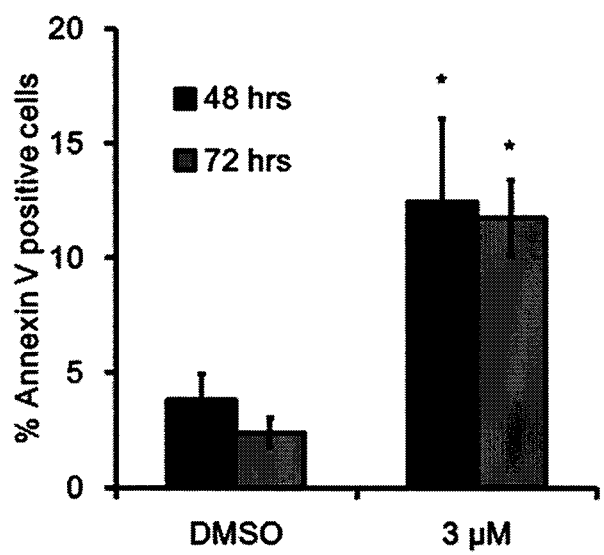

[FIG. 47]
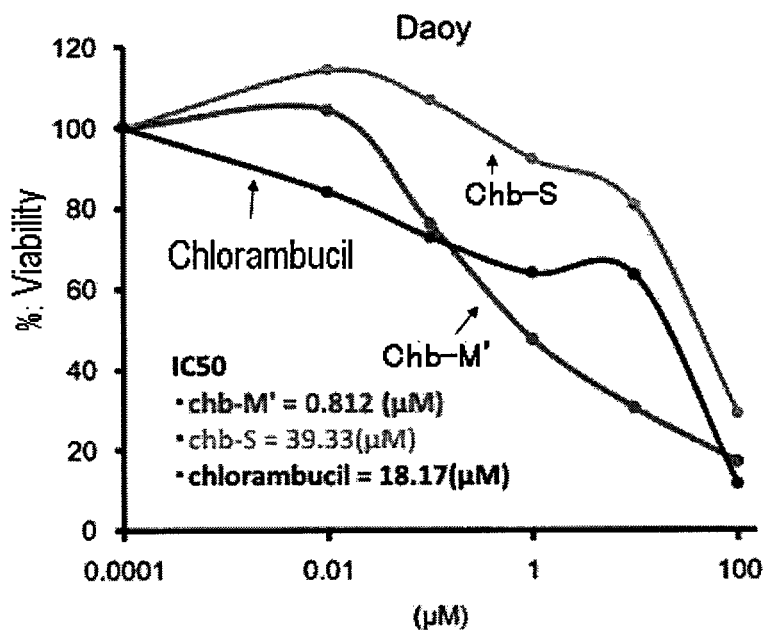
[FIG. 48]
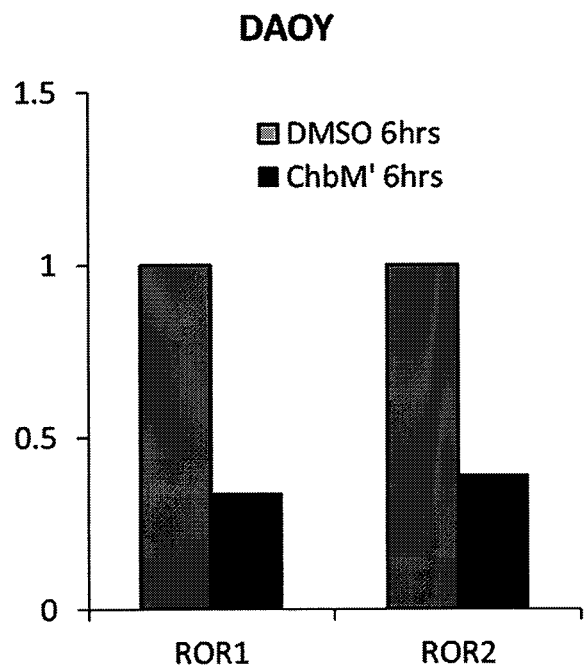

[FIG. 49]
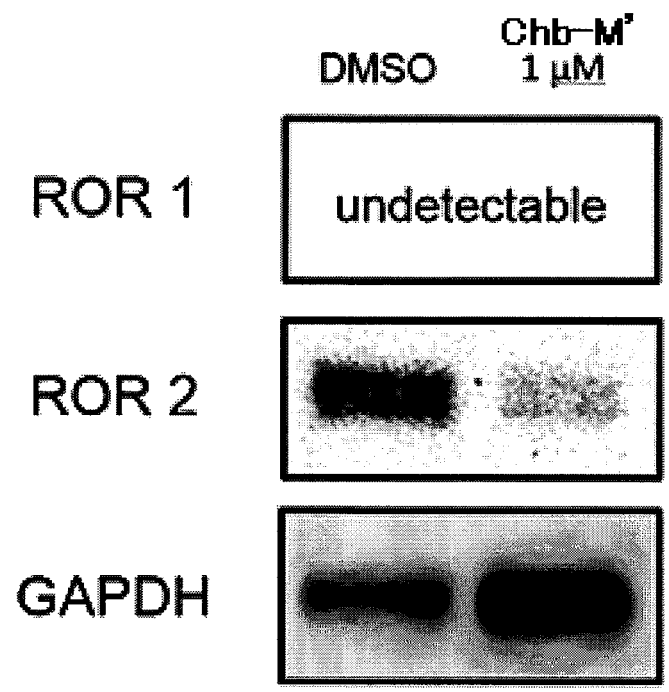

[FIG. 50-1]
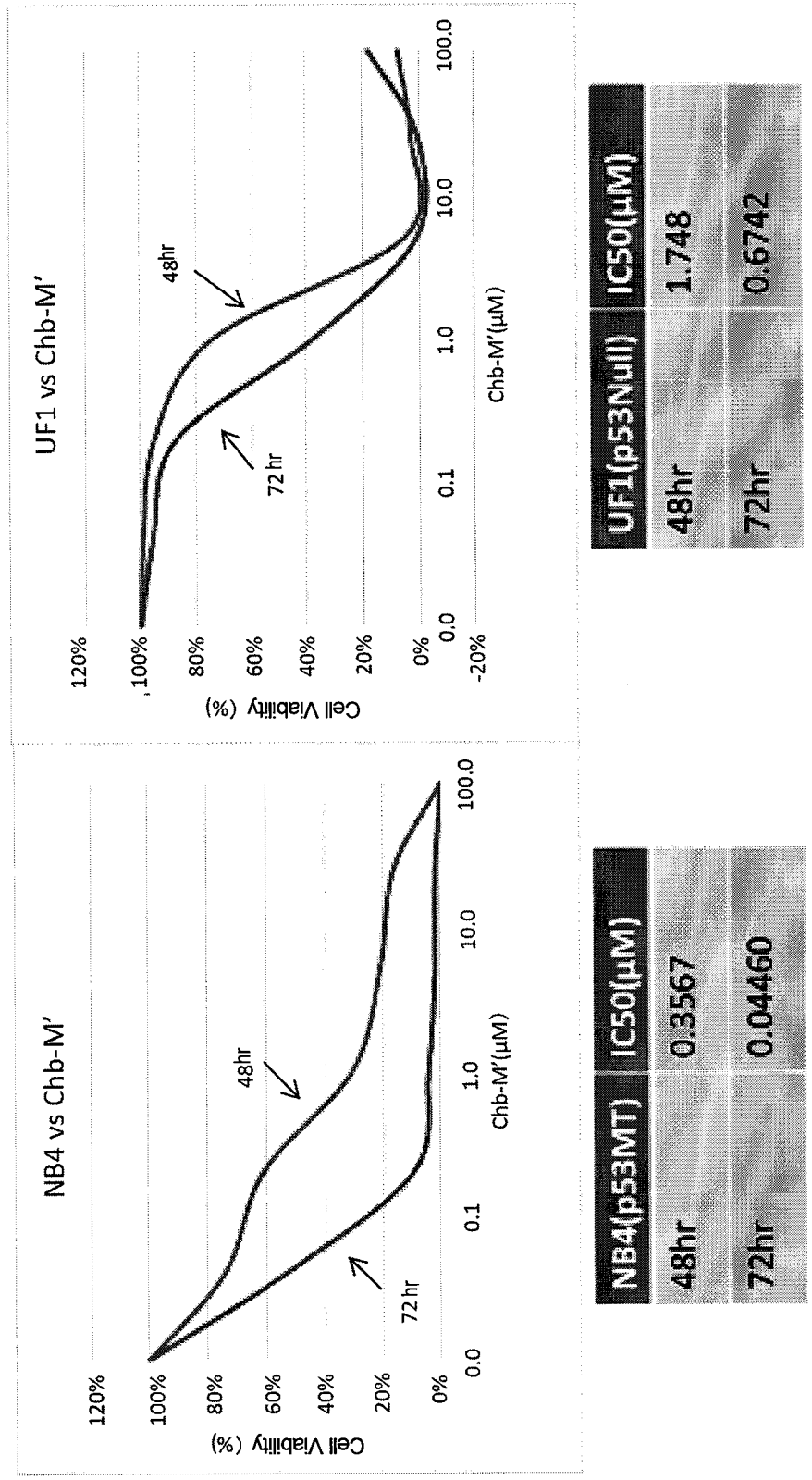

[FIG. 50-2]
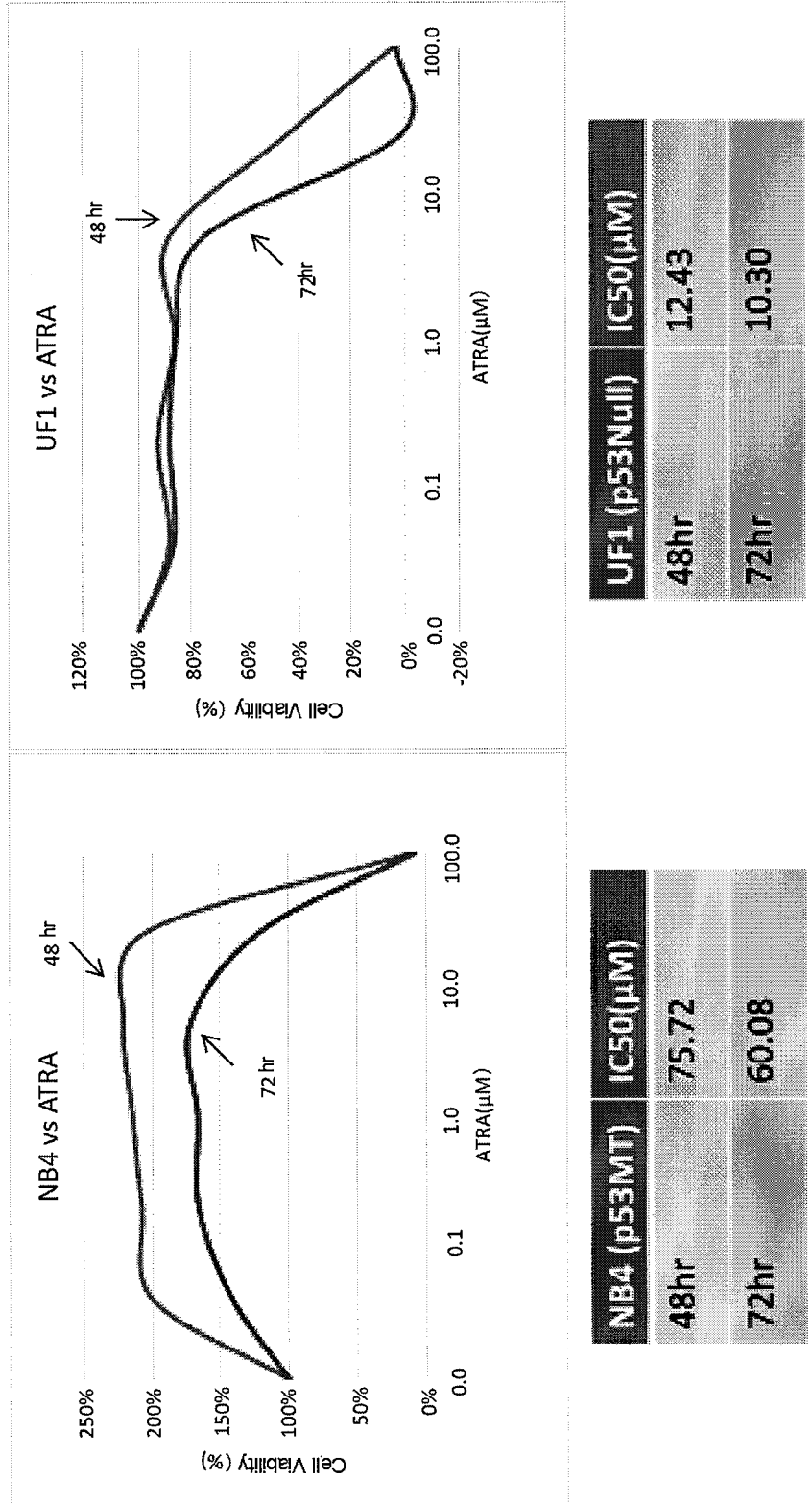

RUNX INHIBITOR

TECHNICAL FIELD

The present invention relates to a RUNX inhibitor and a pharmaceutical composition comprising the RUNX inhibitor.

BACKGROUND ART

A runt-related transcription factor (hereinafter, referred to as "RUNX") family are important transcription factors that regulate the expressions of blood-related genes and hematopoietic stem cell-related genes. The members of RUNX family include RUNX1, RUNX2 and RUNX3. It is known that RUNX1 is involved in definitive hematopoiesis, etc., RUNX 2 is involved in bone development, etc., and RUNX 3 is involved in neurogenesis, thymopoiesis, etc. Each member of the RUNX family forms a heterodimeric complex with a core-binding factor, beta subunit (CBFβ).

Whereas RUNX regulates the expressions of target genes through recognizing and binding the core consensus binding sequence 5'-TGTGGT-3', and much rarely, 5'-TGCGGT-3' of the regulatory regions of the target genes via a runt domain, CBFβ is a non-DNA binding regulatory subunit. CBFβ allosterically enhances the DNA binding capacity of RUNX.

RUNX1, also known as acute myeloid leukemia 1 protein (AML1), has been considered a tumor suppressor in the development of leukemia. On the other hand, a recent report suggests that RUNX1 has pro-oncogenic properties in the development of acute myeloid leukemia (AML); and small-molecule compounds were reported to inhibit the binding of RUNX1 to CBFβ for treatment of leukemia (see Non-Patent Literature 1). However, there has been no attempt to target a RUNX family-binding site on a genomic DNA for treatment of various cancers including leukemia.

Pyrrole-imidazole polyamides (hereinafter, referred to as "PI polyamides") are synthetic oligomers that recognize specific DNA sequences located within the minor groove by virtue of their pyrrole (P) and imidazole (I) pairs interlocked by a hairpin linkage. Pairing "P" opposite "I" in PI polyamides recognizes a C-G base pair; paring P opposite P recognizes an A-T or T-A base pair; and paring "I" opposite "P" recognizes a G-C pair. The PI polyamides can specifically bind to any double-stranded DNA sequence by virtue of the above recognitions. Thus, designing the order of PI pairs enables in vivo delivery of PI polyamides to the targeted site in genome.

Despite their relatively large molecular weights, PI polyamides are membrane permeant, localize to the cell nucleus, and then affect endogenous gene transcription at nanomolar levels. Target gene-binding PI-polyamides have been studied as a gene switch that inhibits the binding of a transcription factor to DNA and regulates expression of the gene. We have recently succeeded in generating potent histone deacetylase (HDAC) inhibitors, suberoylanilide hydroxamic acid-conjugated (SAHA-conjugated) PI polyamides; and demonstrated that the SAHA-conjugated PI polyamides have the ability to specifically stimulate the expressions of target genes through enhanced acetylation of their regulatory regions (see Non-Patent Literatures 2 and 3). We have also successfully conjugated the nitrogen mustard alkylating agent chlorambucil to PI polyamides; and showed that they have a much stronger sequence-specific genomic DNA-binding capacity and reduce the target gene expressions (see Non-Patent Literatures 4 and 5). It was also reported that a chlorambucil-conjugated PI polyamide targeting the histone H4c gene inhibited the proliferation of colon carcinoma cells (see Non-Patent Literature 6).

To date, however, there has been no report that studies alkylating agent-conjugated PI polyamides targeting the RUNX family and the PI polyamide conjugate-based anti-tumor formulations. Therefore, no application thereof was developed for a specific or a wide range of uses in treatment of cancer(s).

CITATION LIST

Non-Patent Literatures

Non-Patent Literature 1: Cunningham, L et al., Proc Natl Acad Sci USA, 2012 Sep. 4; 109(36), 14592-7

Non-Patent Literature 2: Pandian, G. N. et al., Sci Rep 4, 3843, doi:10.1038/srep03843 (2014)

Non-Patent Literature 3: Saha, A. et al., Bioorg Med Chem 21, 4201-4209, doi:10.1016/j.bmc.2013.05.002 (2013)

Non-Patent Literature 4: Bando, T. et al., Acc Chem Res 39, 935-944, doi:10.1021/ar030287f (2006)

Non-Patent Literature 5: Minoshima, M. et al., Nucleic Acids Symp Ser (Oxf), 69-70, doi:10.1093/nass/nrp035 (2009)

Non-Patent Literature 6: Dickinson, A. et al., Chem Biol, Vol. 11, 1583-1594, 2004

SUMMARY OF INVENTION

Problems to be Solved by the Invention

Conventional small-molecule compounds that inhibit a protein-protein binding such as the binding between RUNX1 and CBFβ have weak ability to move into the nuclei, and the effect is weak. Since conventional molecular target drugs provide actions such as inhibition of protein-protein binding and inhibition of kinase activity by being stuck in a pocket of a causative protein, a mutation in the causative protein induces resistance to the molecular target agents. Therefore, novel antitumor agents that overcome such a defect are needed. Thus, an objective of the present invention is to develop an antitumor agent that suppresses the expression of a causative protein of tumor at a transcriptional level.

Solutions to the Problems

Under the above-described circumstances, the present inventors researched RUNX family inhibitors while expecting that the onset of cancer, in particular leukemia may be affected by inhibiting the activity of RUNX family. As a result, the present inventors found that RUNX inhibitors targeting RUNX binding sites on a genomic DNA are effective against various cancers including leukemia. The present inventors successfully synthesized PI polyamides that target RUNX consensus binding sites on a genome, and found that conjugates of the PI polyamides with alkylating agents can be used to down-regulate the expressions of target genes. Surprisingly, it was found that the conjugates have in vivo inhibition effects not only on AML cells but also on tumors from diverse organs.

The present invention provides the following aspects, which it is not limited to:

[1] A RUNX inhibitor, which binds to a RUNX binding sequence on a DNA to inhibit binding of a RUNX family member to the binding sequence,

[2] The RUNX inhibitor according to [1], which comprises a PI polyamide that binds to the RUNX binding sequence,
[3] The RUNX inhibitor according to [2], which comprises a conjugate of an acting agent and a PI polyamide, and wherein the pyrrole-imidazole polyamide binds to the RUNX binding sequence,
[4] The RUNX inhibitor according to [3], wherein the conjugate of an acting agent and a PI polyamide is selected form the group consisting of compounds represented by formula I:

[Chemical formula 1]

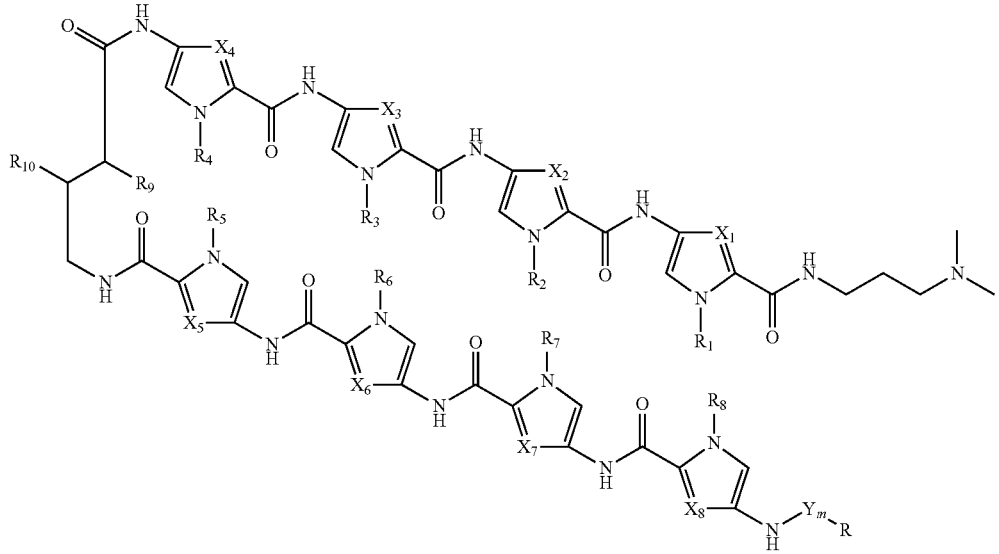

or formula II:

[Chemical formula 2]

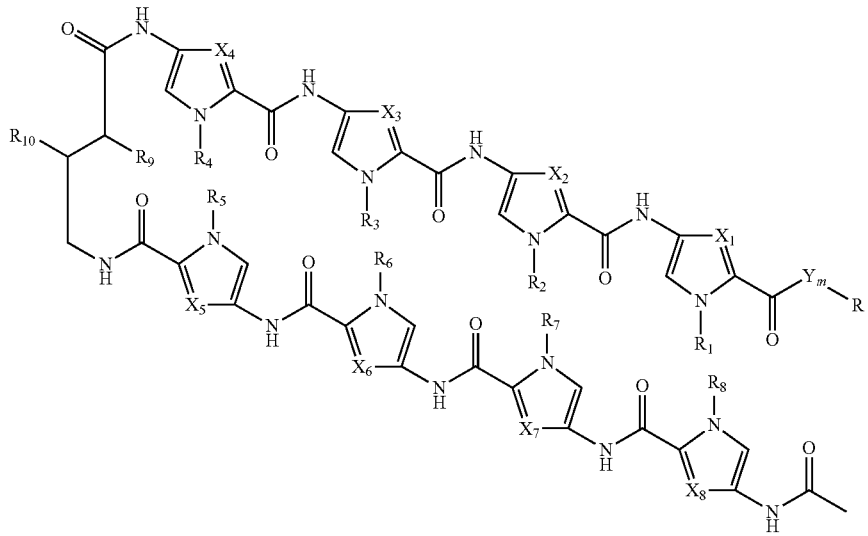

wherein, in formula I or formula II,
$X_1$ represents CH or N, $X_2$ represents CH or N, $X_3$ represents CH or N, $X_4$ represents CH or N, $X_5$ represents CH or N, $X_6$ represents CH or N, $X_7$ represents CH or N, $X_8$ represents CH or N, $R_1$ represents H or alkyl, $R_2$ represents H or alkyl, $R_3$ represents H or alkyl, $R_4$ represents H or alkyl, $R_5$ represents H or alkyl, $R_6$ represents H or alkyl, $R_7$ represents H or alkyl, $R_8$ represents H or alkyl, $R_9$ represents H or $NHR_{11}$, $R_{10}$ represents H or $NHR_{11}$, $R_{11}$ represents H, biotin, or a fluorescent group, R represents an acting agent, Y represents an amide bond, a phosphodisulfide bond, an ester bond, a coordinate bond, or an ether bond, or a moiety containing a functional group that forms at least one selected from the bonds, and m represents an integer of 0 to 5,

[5] The RUNX inhibitor according to [3] or [4], wherein the acting agent is an alkylating agent,

[6] The RUNX inhibitor according to [5], wherein the alkylating agent is selected from the group consisting of chlorambucil, duocarmycin, seco-CBI (1-chloromethyl-5-hydroxy-1,2-dihydro-3H-benzo[e]indole), pyrrolobenzodiazepine, and Nitrogen mustard,
[7] The RUNX inhibitor according to [6], wherein the alkylating agent is chlorambucil,
[8] The RUNX inhibitor according to [7], wherein the conjugate of chlorambucil and a PI polyamide is selected form the group consisting of compounds represented by formulae:

[Chemical formula 3]

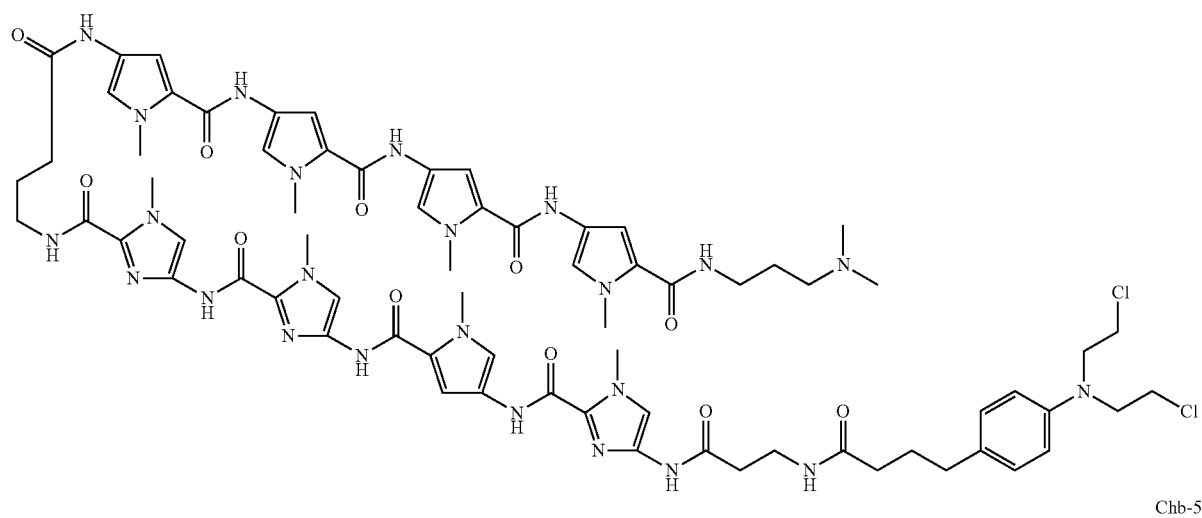

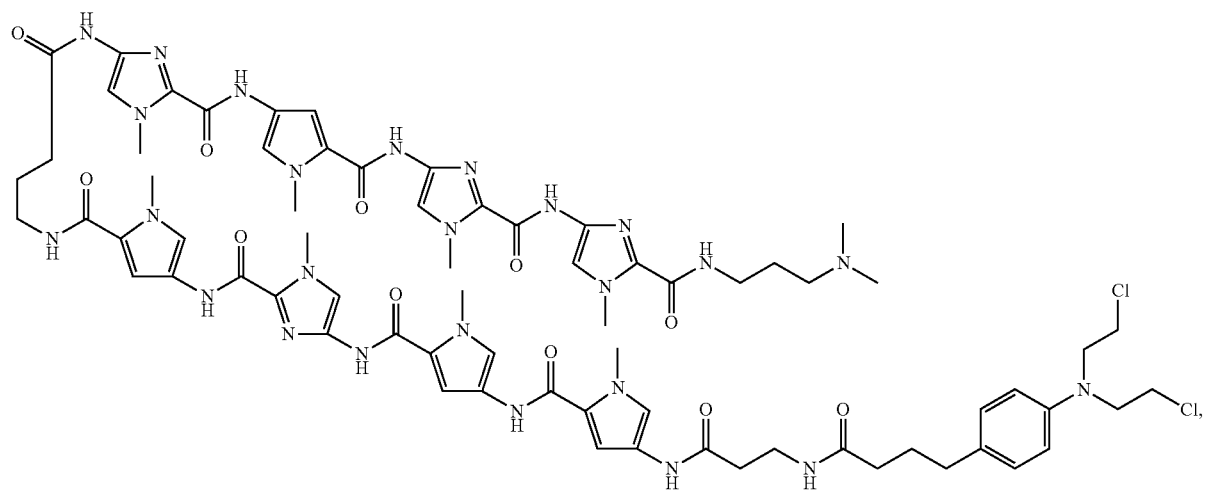

[9] The RUNX inhibitor according to any one of [1]-[8], which inhibits binding of all members of RUNX family to the RUNX binding sequence,
[10] A pharmaceutical composition comprising the RUNX inhibitor according to any one of [1]-[9],
[11] The pharmaceutical composition according to [10], which is an antitumor agent,
[12] The pharmaceutical composition according to [10], which is antiallergic agent,
[13] The pharmaceutical composition according to [11], which is used in combination with another antitumor agent,
[14] The pharmaceutical composition according to [11] or [13], for prevention or treatment of at least one selected from the group consisting of leukemia, lymphoma, multiple myeloma, lung cancer, esophageal cancer, gastric cancer, colon cancer, renal cell cancer, neuroblastoma, skin cancer, breast cancer, prostate cancer, and brain tumor,
[15] A preventive or therapeutic method of cancer, comprising administering the pharmaceutical composition according to [10] to a subject,
[16] A preventive or therapeutic method of cancer, comprising administering the pharmaceutical composition according to [10] in combination with another antitumor agent,
[17] The preventive or therapeutic method according to [15] or [16], wherein the cancer is selected from the group consisting of leukemia, lymphoma, multiple myeloma, lung cancer, esophageal cancer, gastric cancer, colon cancer, renal cell cancer, neuroblastoma, skin cancer, breast cancer, prostate cancer, and brain tumor,
[18] Use of the RUNX inhibitor according to any one of [1]-[9] for manufacture of an antitumor agent,

[19] Use of the RUNX inhibitor according to any one of [1]-[9] for manufacture of an antiallergic agent,

[20] The RUNX inhibitor according to any one of [1]-[9] for use in prevention or treatment of cancer,

[21] The RUNX inhibitor according to [20], wherein the cancer is selected from the group consisting of leukemia, lymphoma, multiple myeloma, lung cancer, esophageal cancer, gastric cancer, colon cancer, renal cell cancer, neuroblastoma, skin cancer, breast cancer, prostate cancer, and brain tumor,

[22] A preventive or therapeutic method of cancer, comprising inhibiting binding of a RUNX family member to a RUNX binding sequence on a DNA,

[23] The preventive or therapeutic method according to [22], wherein the cancer is selected from the group consisting of leukemia, lymphoma, multiple myeloma, lung cancer, esophageal cancer, gastric cancer, colon cancer, renal cell cancer, neuroblastoma, skin cancer, breast cancer, prostate cancer, and brain tumor.

Effects of the Invention

The RUNX inhibitor of the present invention can inhibit the binding of all members of RUNX family to RUNX binding sequences to inhibit the activity of the RUNX family. Thus, the RUNX inhibitor of the present invention can exert its effect on any disease and symptom which the RUNX family members are involved in. An anti-tumor agent comprising the RUNX inhibitor of the present invention has an antitumor effect on various types of cancers including leukemia. The anti-tumor agent of the present invention exerts its effects even on tumors that are resistant to other molecular target drugs. In addition, the RUNX inhibitor of the present invention can be also used as an antiallergic agent.

BRIEF DESCRIPTION OF DRAWINGS

FIG. 1 shows chemical formulae representing Chlorambucil/PI polyamide conjugates used in Examples.

FIG. 2 shows the expression levels of IL3, CSF2, and CSF2RB genes in Human Myeloid Leukemic MV4-11 cells treated with the chlorambucil/PI polyamide conjugates. Each value of chlorambucil/PI polyamide conjugate-treated cells for the gene expressions is normalized to that of the DMSO-treated cell. In the figure, data are the mean±SEM values. *P<0.05.

FIG. 3 shows the expression levels of BCL11A, TRIM24, p21, BAX, PUMA, and MDM2 genes in Human Myeloid Leukemic MV4-11 cells treated with the chlorambucil/PI polyamide conjugates. Each value of chlorambucil/PI polyamide conjugate-treated cells for the gene expressions is normalized to that of the DMSO-treated cell. In the figure, N.S. indicates Not Significant; Data are the mean±SEM values; *P<0.05.

FIG. 4 shows results of immunoblotting of BCL11A, TRIM24, p21, BAX, PUMA, MDM2, PARP, PARP cleaved form, and cleaved caspase-3 protein in Human Myeloid Leukemic MV4-11 cells treated with the chlorambucil/PI polyamide conjugates.

FIG. 5 shows dose-response curves of Chb-M' in AML cells (MV4-11, OCI-AML2, OCI-AML3, and MOLM-13 cells).

FIG. 6 shows $IC_{50}$ values of Chb-M' against human cancer cell lines established from various origins. In the figure, "p53WT" indicates wild-type p53 cell lines; and "p53 mutation (+)" indicates p53-mutated or p53-deficient cell lines.

FIG. 7 shows $IC_{50}$ values of Chb-50 against human cancer cell lines established from various origins. In the figure, "p53WT" indicates wild-type p53 cell lines; and "p53 mutation (+)" indicates p53-mutated or p53-deficient cell lines.

FIG. 8 shows combination index plots of Chb-M' and PRIMA-1 in p53 function disrupted AML cells.

FIG. 9 shows results of acute toxicological testing using different concentrations of Chb-M' in NOG mice. The results of complete blood cell counts (a), blood biochemistry (b), and body weight (c) are shown (n=5). Data are the mean±SEM values.

FIG. 10 shows overall survival rates of NOG mice transplanted with MV4-11 cells followed by treatment with DMSO, Ara-C, Chb-S, Chb-M', or Chb-50 (n=7).

FIG. 11-1 shows microscopic images of bone marrow from AML mice transplanted with MV4-11 cells. Hematoxylin and eosin staining (HE) and immunohistochemical staining with anti-human CD45 antibody (hCD45) were carried out for each slide. "DMSO", "AraC" and "Chb-M'" indicate histological staining from DMSO-treated, cytarabine-treated and Chb-M'-treated mice, respectively.

FIG. 11-2 shows microscopic images of bone marrow from AML mice transplanted with MV4-11 cells. Hematoxylin and eosin staining (upper 2 rows) and immunohistochemical staining with anti-human CD45 antibody (lower 2 rows) were carried out for each slide. "WT" indicates histological staining from mice not transplanted with cancer cells and "Chb-S" indicates histological staining from Chb-S-treated mice.

FIG. 12 shows overall survival rates of NOG mice which underwent SU/SR-cell transplantation followed by treatment with DMSO, imatinib, or Chb-M' (n=5).

FIG. 13 shows microscopic images of bone marrow from ALL mice transplanted with SU/SR cells. Hematoxylin and eosin staining (HE) and immunohistochemical staining with anti-human CD45 antibody (hCD45) were carried out for each slide. "DMSO", "imatinib" and "Chb-M'" indicate histological staining from DMSO-treated, imatinib-treated and Chb-M'-treated mice, respectively.

FIG. 14 shows microscopic images of livers from ALL mice transplanted with SU/SR cells. Hematoxylin and eosin staining (upper 2 rows) and immunohistochemical staining with anti-human CD45 antibody (lower 2 rows) were carried out for each slide. "WT" indicates histological staining from mice not transplanted with cancer cells. Further, "DMSO", "imatinib" and "Chb-M'" indicate histological staining from DMSO-treated, imatinib-treated, and Chb-M'-treated mice, respectively.

FIG. 15 shows microscopic images of spleens from ALL mice transplanted with SU/SR cells. Hematoxylin and eosin staining (upper 2 rows) and immunohistochemical staining with anti-human CD45 antibody (lower 2 rows) were carried out for each slide. "WT" indicates histological staining from mice not transplanted with cancer cells. Further, "DMSO", "Imatinib" and "Chb-M'" indicate histological staining from DMSO-treated, imatinib-treated and Chb-M'-treated mice, respectively.

FIG. 16 shows overall survival rates of human lung cancer xenotransplant mice which underwent A549-cell transplantation followed by treatment with DMSO, gefitinib, or Chb-M' (n=5).

FIG. 17 shows live bioluminescent images at 7, 14, and 21 days after transplantation of A549 cells in the mice, in which the human lung cancer-xenotransplant mice underwent the treatment with DMSO, gefitinib, or Chb-M' semiweekly, i.e. the second and the forth administrations at 14 days and at 21 days after the transplantation, respectively; while the mice at 7 days received no drug administration. Rainbow scale represents relative light units.

FIG. 18 shows quantification of the bioluminescent signal intensity at 21 days after A549-cell transplantation in the mice, in which the human lung cancer-xenotransplant mice underwent the treatment with DMSO, gefitinib, or Chb-M' (n=5).

FIG. 19 shows microscopic images of lungs from a lung cancer xenograft mice with A549 cells. Hematoxylin and eosin staining (upper 2 rows) and immunohistochemical staining with anti-human Ki-67 antibody (lower 2 rows) were carried out for each slide. "WT" indicates histological staining from mice not transplanted with cancer cells. Further, "DMSO", "Gefitinib" and "Chb-M'" indicate histological staining from DMSO-treated, gefitinib-treated and Chb-M'-treated mice, respectively.

FIG. 20 shows tumor volume curves of human gastric cancer-xenografted mice which underwent MKN45-cell transplantation followed by treatment with DMSO or Chb-M' (n=8). In the figure, *p<0.05, p<0.01, and *p<$10^{-4}$.

FIG. 21 shows live bioluminescent images at 7, 21 and 35 days after MKN45 cell-transplantation in the mice, in which the human gastric cancer-xenografted mice underwent treatment with DMSO or Chb-M' semiweekly, i.e. the second and the eighth administrations at 21 days and at 35 days after the transplantation, respectively; while the mice at 7 days received no drug administration. The rainbow scale indicates relative light units.

FIG. 22 shows microscopic images of tumors at 35 days after MKN45-cell transplantation in the mice, in which the human gastric cancer-xenografted mice underwent treatment with DMSO or Chb-M' at 35 days after the transplantation.

FIG. 23 shows correlation between the expression levels of CBFβ gene and RUNX1+RUNX2+RUNX3 (Pan-_RUNX) genes (n=9).

FIG. 24 shows correlation between the expression levels of CBFβ protein and RUNX1+RUNX2+RUNX3 proteins in AML cell lines (n=9).

FIG. 25-1 shows expression levels of BCR-ABL gene in MYL cells treated with Chb-M'. The value of the Chb-M' treated cells is normalized to that of DMSO (control)-treated cells.

FIG. 25-2 shows expression levels of BCR-ABL gene in SU-Ph2 cells and SU/SR cells treated with Chb-M'. Each value of the Chb-M' treated cells is normalized to that of DMSO (control)-treated cells.

FIG. 26-1 shows immunoblots of BCR-ABL fusion proteins in MYL cells treated with Chb-M'.

FIG. 26-2 shows immunoblots of BCR-ABL fusion proteins in SU-Ph2 cells and SU/SR cells treated with Chb-M'.

FIG. 26-3 shows immunoblots of Bcl2 and C-Myc in MYL cells treated with Chb-M'.

FIG. 26-4 shows results of apoptosis induction in MYL cells treated with Chb-M' at 48 hours after treatment.

FIG. 27-1 shows a dose-response curve of Chb-M' in MYL cells.

FIG. 27-2 shows dose-response curves and $IC_{50}$ values of Chb-50, Chb-M', and imatinib in SU-Ph2 cells and SU/SR cells.

FIG. 28 shows expression levels of different genes in HUVEC (human umbilical vein endothelial cell line) treated with different concentrations of Chb-M'. The expression levels are shown as expression levels relative to the expression level of each gene in the cell treated with 0 µM Chb-M' (i.e. DMSO). In the figure, results of E-selectin-1, E-selectin-2, P-selectin, Tie2, ICAM-1, VCAM-1, and Jagged-1 are shown in the order from left to right at different concentrations.

FIG. 29 shows results from FACS (fluorescence-activated cell sorter) analysis of the expression levels of E-selectin in HUVEC treated with Chb-M' (upper) and HUVEC in which the expression of RUNX1 gene was knockdown (lower).

FIG. 30 is a schematic illustration of an in vivo experiment scheme for the analysis of changes in E-selectin expression levels in bone marrow endothelial cells by Chb-M' administration.

FIG. 31 shows results from FACS analysis of the expression levels of E-selectin in endothelial cells of mice treated with Chb-M' administration.

FIG. 32 is a schematic illustration of a homing assay performed in Examples.

FIG. 33 shows leukemia cell numbers in bone marrow and spleen of Chb-M'-treated mice transplanted with leukemia cells (MLL-ENL) via tail vein at 24 hours after transplantation.

FIG. 34 shows results of immunoblotting of Her2, p-ERK, ERK, p-AKT, and AKT in MKN45 gastric cancer cells (Her2 inhibitor-resistant cells) treated with Chb-M'.

FIG. 35 shows results of immunoblotting of SOS1, p-Her2 (phospho-Her2), and Her2 in MKN45 gastric cancer cells treated with Chb-M'.

FIG. 36 shows the expression level of SOS1 gene in MKN45 gastric cancer cells treated with Chb-M'. The expression level is shown as a value relative to that in the cell treated with DMSO (control).

FIG. 37 shows dose-response curves and IC50 values of Chb-M', gefitinib, and chlorambucil in EGFR wild-type p53 wild-type lung adenocarcinoma cells (A549 and LU99A).

FIG. 38 shows dose-response curves and IC50 values of Chb-M', gefitinib, chlorambucil, and Chb-S in EGFR wild-type p53-mutated lung adenocarcinoma cell lines (ABC-1 and RERF-LC-MS).

FIG. 39 shows results of immunoblotting of Mig6 in LU99A cells and A549 cells treated with Chb-M'.

FIG. 40 shows results of immunoblotting of various apoptosis-related factors (p53, p21, PUMA, and BAX) in LU99A cells and A549 cells treated with Chb-M'. In the figure, "C-M" indicates the Chb-M'-administered group.

FIG. 41 shows results from FACS (fluorescence-activated cell sorter) analysis of surface expression levels of KIT in LAD2 cells and HMC-1.2 cells treated with Chb-M'.

FIG. 42 shows results of immunoblotting of KIT, pKIT, AKT, pAKT, Mitf, and GAPDH in LAD2 cells and HMC-1.2 cells treated with Chb-M'.

FIG. 43 shows dose-response curves of Chb-M' and chlorambucil (Chb) in p53-mutated colon cancer cell HT29.

FIG. 44 shows dose-response curves and 1050 values of Chb-M', Ch-S, chlorambucil, and Enzalutamide in prostate cancer cells (PC-3, DU-145, and LNCaP).

FIG. 45 shows the expression levels of GATA2, E2F5, and AR genes in prostate cancer cell PC-3 treated with Chb-M'. The value of the Chb-M' treated cells is normalized to that of DNSO (control)-treated cell.

FIG. 46 shows results of apoptosis induction in prostate cancer cells treated with Chb-M' after 48 and 72 hours.

FIG. 47 shows dose-response curves and 1050 values of Chb-M', Ch-S, and chlorambucil in medulloblastoma cells.

FIG. 48 shows the expression levels of ROR1 and ROR2 genes in medulloblastoma cell DAOY treated with Chb-M'.

The value of the Chb-M' treated cells is normalized to that of DMSO (control)-treated cell.

FIG. 49 shows results of immunoblotting of ROR1 and ROR2 proteins in DAOY cells treated with Chb-M'.

FIG. 50-1 shows dose-response curves and 1050 values of Chb-M' in APL cell lines (NB4 and UF1).

FIG. 50-2 shows dose-response curves and 1050 values of ATRA in APL cell lines (NB4 and UF1).

MODE FOR CARRYING OUT THE INVENTION

1. RUNX Inhibitors

The binding of the RUNX inhibitors for the present invention to RUNX-binding sequences on DNA leads to inhibition of the binding of RUNX family members to the binding sequences, thereby repressing the RUNX family members' activity.

Examples of the RUNX inhibitors include, but not limited to, synthetic inhibitors containing DNA binding compounds designed to bind to a RUNX binding sequence; and the DNA binding compounds includes PI polyamides, peptide nucleic acids (PNAs), triple-stranded DNAs, TAL effector proteins, bridged nucleic acids (BNAs), locked nucleic acids (LNAs), and zinc finger and the like.

The RUNX inhibitor of the present invention preferably contains a PI polyamide that binds to a RUNX binding sequence. The PI polyamide is a polyamide containing N-methylpyrrole units (P), N-methylimidazole units (I), and a γ-aminobutyric acid moiety, in which P, I, and the γ-aminobutyric acid moiety are linked to one another via amide bonds (—C(=O)—NH—) (Trauger et al, Nature, 382, 559-61(1996); White et al, Chem. Biol., 4,569-78(1997); and Dervan, Bioorg. Med. Chem., 9, 2215-35 (2001)). The PI polyamide is wholly folded in a U-shaped conformation (hairpin form) by the γ-aminobutyric acid moiety serving as a linker (γ-linker). In the U-shaped conformation, two chains containing P and I are arranged in parallel, flanking the linker. When pairs containing P and I formed between the two chains are specific combinations of P and I (P/I pair, I/P pair, or P/P pair), they can bind to specific base pairs in DNA with high affinity. For example, a P/I pair can bind to a C.G pair and an I/P pair can bind to a G•C pair. A P/P pair can bind to both an A•T pair and a T•A pair (White et al, Chem. Biol., 4, 569-78(1997); Dervan: Bioorg. Med. Chem., 9, 2215-35 (2001)). The PI polyamide may contain 3-hydroxy-pyrrole (Hp) or β-alanine in addition to P and I. An Hp/P pair can bind to a T•A pair (White et al., Nature, 391, 468-71 (1998)). A β-alanine/β-alanine pair can bind to a T•A pair and an A•T pair. The PI polyamide that recognizes a regulatory region of a target gene can be designed by changing the paring combinations of P and I according to the DNA sequence of the target.

In the PI polyamide, a methyl group on a nitrogen atom at position 1 of P or I may be substituted by hydrogen or an alkyl group other than a methyl group. The γ-linker may be a linker having a side chain, for example, N-α-N-γ-diaminobutyric acid and N-β-N-γ-diaminobutyric acid which have an amino group, and the side chain may be modified with a molecule such as a fluorescent group or biotin. The PI polyamide may be modified at its N terminus with not only an acetyl group but also a molecule such as a fluorescent group or biotin. As used herein, examples of the fluorescent group include, but not limited to, fluorescein, rhodamine dyes, cyanine dyes, ATTO dyes, Alexa Fluor dyes, and BODIPY. The fluorescein includes fluorescein derivatives (for example, fluorescein isothiocyanate).

Methods for designing and producing the PI polyamides are known (see, for example, JP-B 3045706, JP-A 2001-136974, WO03/000683, JP-A 2013-234135, and JP-A 2014-173032). For example, the PI polyamides can be produced conveniently by an automated synthesis method comprising solid-phase synthesis using Fmoc (9-fluorenylmethoxycarbony) (Fmoc solid-phase synthesis method).

The PI polyamide may be a modified form of PI polyamide that is modified to maintain or improve the ability to bind to DNA. Examples of the modified form of PI polyamide include a modified form containing an amine added to position α or β of the γ-aminobutyric acid of the PI polyamide, a modified form having a substituted side chain that is N-α-N-γ-diaminobutyric acid or N-β-N-γ-diaminobutyric acid and the modified form further modified with a molecule such as a fluorescent group or biotin, a modified form containing modification with a molecule such as a fluorescent group or biotin at the N terminus of the PI polyamide, and a modified form containing modification with a molecule such as isophthalic acid at the C terminus of the PI polyamide.

As used in the present invention, a PI polyamide recognizes and binds to RUNX consensus binding sequences in genome. A RUNX consensus binding sequence is known to be 5'-TGTGGT-3' or 5'-TGCGGT-3'. Thus, the pairing combinations of P, I, and/or Hp and β-alanine in the PI polyamide as described above may be determined according to the RUNX consensus binding sequence. The PI polyamide can strongly inhibit biding of RUNX family to a RUNX binding sequence on a genome.

The RUNX inhibitor of the present invention may preferably comprise a conjugate of the above-described DNA binding compound that binds to a RUNX binding sequence with an acting agent. More preferred examples of the RUNX inhibitor of the present invention comprise a conjugate of a PI polyamide that binds to a RUNX binding sequence with an acting agent. The acting agent is a substance that influences DNA and a state of chromatin surrounding the DNA. Examples of the acting agent include, but not limited to, an alkylating agent and a chromatin modifying enzyme-regulating agent. Examples of the chromatin modifying enzyme-regulating agent include, but not limited to, histone acetylase (HAT) regulating agents such as HAT inhibitors (e.g., C646) and HAT activators (e.g., N-(4-chloro-3-(trifluoromethyl) phenyl)-2-ethoxybenzamide (CTB)); histone deacetylase (HDAC) regulating agents such as HDAC inhibitors (e.g., suberoylanilide hydroxamic acid) and HDAC activators; histone methylase regulating agents; and histone demethylase regulating agents. More preferred examples of the RUNX inhibitor of the present invention comprise a conjugate of a PI polyamide that binds to a RUNX binding sequence with an alkylating agent.

An alkylating agent is a compound having a functional group that forms a covalent bond with DNA. The alkylating agent used in the present invention is not particularly limited, but it is preferably an alkylating agent having low or no cytotoxicity in view of application to a pharmaceutical composition as described below. Examples of the alkylating agent include, but not limited to, chlorambucil, duocarmycin, seco-CBI (1-chloromethyl-5-hydroxy-1,2-dihydro-3H-benzo[e]indole), pyrrolobenzodiazepine, and Nitrogen mustard.

A complex is synthesized by binding (hereinafter, also referred to as "conjugation") etc. between the above-described acting agent and the above-described DNA binding compound. As used herein, the complex is also referred to as a "conjugate". The synthesis method can be performed by a known method (see, for example, J. Am. Chem. SOC. 1995, 117, 2479-2490). When the DNA binding compound is a PI polyamide, the acting agent is bound to the N terminus, C terminus, or γlinker moiety of the PI polyamide. For example, the acting agent is bound to the N terminus or C terminus of the PI polyamide. In this context, the "binding" manner may be direct binding or binding via a linker. The linker is not particularly limited as long as the linker interferes with neither the action of the acting agent nor the recognition of a RUNX binding site. Examples of the linker include bonds themselves such as an amide bond, a phosphodisulfide bond, an ester bond, a coordinate bond, an ether bond and the like, and a molecule containing a functional group that forms at least one type of the bonds. The "molecule containing a functional group that forms at least one type of the bonds" is a molecule containing a functional group that forms at least one type of bonds selected from the group consisting of an amide bond, a phosphodisulfide bond, an ester bond, a coordinate bond, an ether bond and the like, along with the terminal portion of the PI polyamide and/or the acting agent. The "molecule containing a functional group that forms at least one type of the bonds" may be a molecule containing one or more bonds being at least one type of bonds selected from the group consisting of an amide bond, a phosphodisulfide bond, an ester bond, a coordinate bond, an ether bond and the like. Preferred examples of the linker include an amide bond, and a molecule containing a functional group that forms an amide bond.

Examples of the conjugate of an acting agent and a PI polyamide in the present invention include compounds represented by formula I:

[Chemical formula 4]

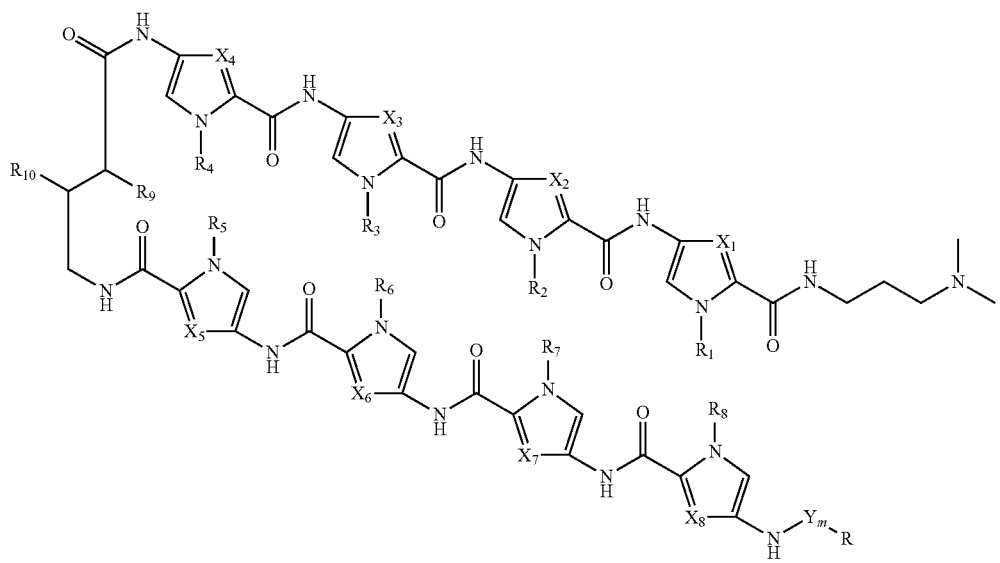

or formula II:

[Chemical Formula 5]

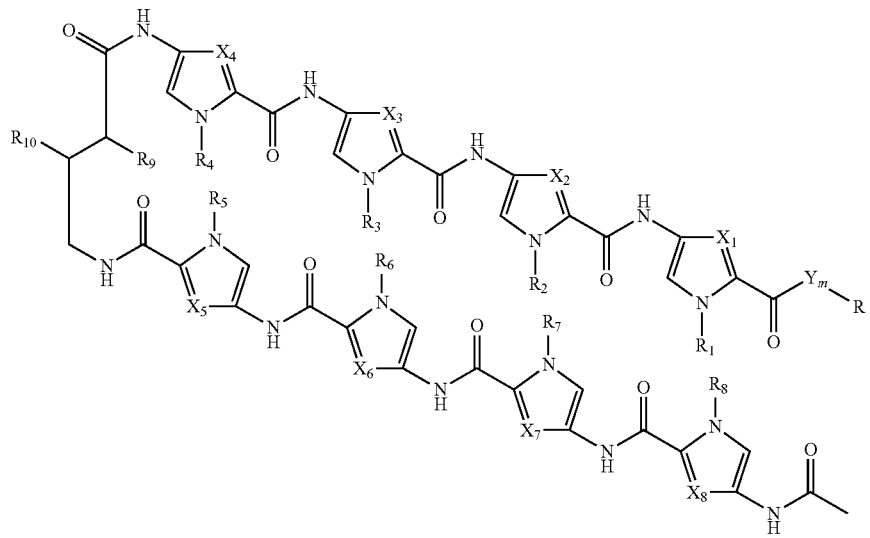

wherein, $X_1$ represents CH or N, $X_2$ represents CH or N, $X_3$ represents CH or N, $X_4$ represents CH or N, $X_5$ represents CH or N, $X_6$ represents CH or N, $X_7$ represents CH or N, $X_8$ represents CH or N, wherein $X_1$ to $X_8$ are selected in a combination that enables the PI polyamide to recognize a RUNX consensus sequence, $R_1$ represents H or alkyl, $R_2$ represents H or alkyl, $R_3$ represents H or alkyl, $R_4$ represents H or alkyl, $R_5$ represents H or alkyl, $R_6$ represents H or alkyl, $R_7$ represents H or alkyl, $R_8$ represents H or alkyl, $R_9$ represents H or $NHR_{11}$, $R_{10}$ represents H or $NHR_{11}$, $R_{11}$ represents H, or a molecule such as biotin or a fluorescent group, R represents an acting agent, preferably an alkylating agent, and more preferably an alkylating agent selected from the group consisting of chlorambucil, duocarmycin, seco-CBI, pyrrolobenzodiazepine, and Nitrogen mustard, Y represents a linker moiety, and m represents an integer of 0 to 5, preferably an integer of 0 to 3, more preferably 0 or 1; and modified forms of the compounds.

In the above formulae I and II, Y represents, for example, a bond such as an amide bond, phosphodisulfide bond, an ester bond, a coordinate bond, an ether bond or the like, or a moiety containing a functional group that forms at least one type of the bonds. In this context, the "moiety containing a functional group that forms at least one type of the bonds" is a moiety containing a functional group that forms at least one type of bonds selected from the group consisting of an amide bond, a phosphodisulfide bond, an ester bond, a coordinate bond, an ether bond and the like, along with the terminal portion of the PI polyamide and/or the acting agent. The "moiety containing a functional group that forms at least one type of the bonds" may contain one or more bonds being at least one type of bonds selected from the group consisting of an amide bond, a phosphodisulfide bond, an ester bond, a coordinate bond, an ether bond and the like.

In one embodiment, in the above formulae I and II, Y is the "moiety containing a functional group that forms at least one type of the bonds", and an example thereof includes a structure represented by formula III:

[Chemical formula 6]

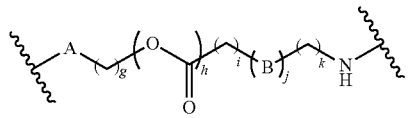

wherein,

A is carbonyl [—C(=O)—] or imino (—NH—),

B is an ether bond (—O—), imino (—NH—) or methylimino [—N(—CH₃)—], g and k represent independently an integer of 1 to 3, h and j represent independently an integer of 0 to 5, and i represents an integer of 0 to 2. For example, it is preferable that h and j represent independently an integer of 0 to 3. In the above formula III, the position of the ester bond and the position of the ether bond or imino bond represented by B may be replaced by, each other. For example, the linker moiety represented by the above formula III is linked at the rightmost position to the acting agent and at the leftmost position to the PI polyamide. However, whereas the linking positions may be reversed. For example, when the linker moiety represented by the above formula III is linked at the leftmost position to the C terminus of the PI polyamide, A is preferably imino.

An Example of Y represented by formula III includes a structure represented by formula IV:

[Chemical formula 7]

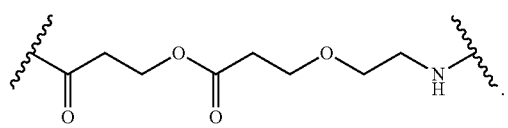

Another example of Y represented by formula III includes a structure represented by formula V:

[Chemical formula 8]

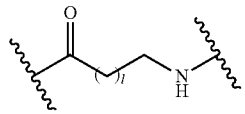

wherein, l represents an integer of 1 to 5. For example, l is an integer of 1 to 3, and preferably l is 1.

Another example of Y represented by formula III includes a structure represented by formula VI:

[Chemical formula 9]

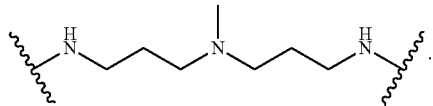

Preferably the linker moiety represented by formula VI is used when the acting agent is linked to the C-terminal side of the PI polyamide.

For example, the linker moieties represented by the above formula IV to formula VI are linked at the rightmost position to the acting agent and at the leftmost position to the PI polyamide. However, the linking positions may be reversed.

As used herein, examples of the alkyl group include a $C_1$-$C_{10}$ linear, branched, or cyclic saturated or unsaturated alkyl group, preferably a $C_1$-$C_5$ linear, branched, or cyclic saturated or unsaturated alkyl group, and for example, methyl, ethyl, n-propyl, isopropyl, n-butyl, sec-butyl, isobutyl, tert-butyl and the like are included. The alkyl group may be substituted. For example, methylene in the alkyl group may be substituted with oxygen or the like.

Preferred examples of the conjugate of an acting agent and a PI polyamide in the present invention include compounds represented by the following formula:

[Chemical formula 10]
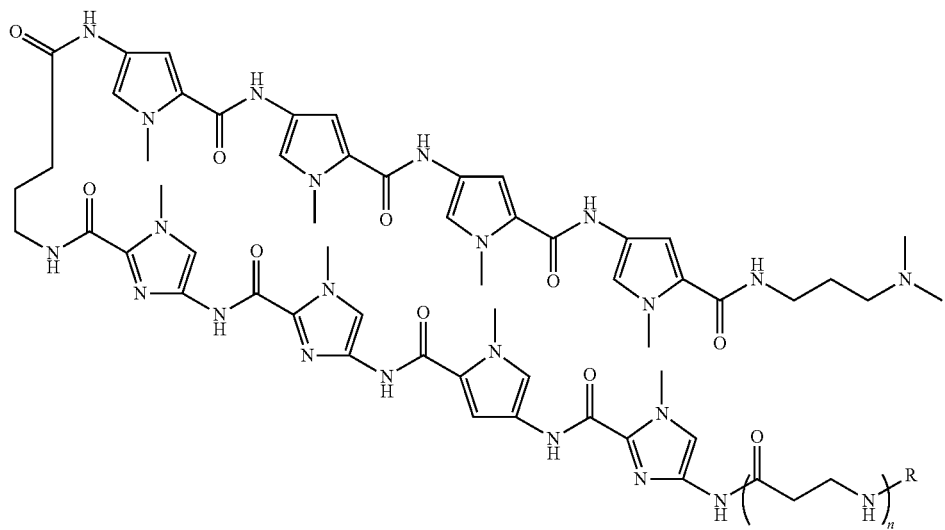
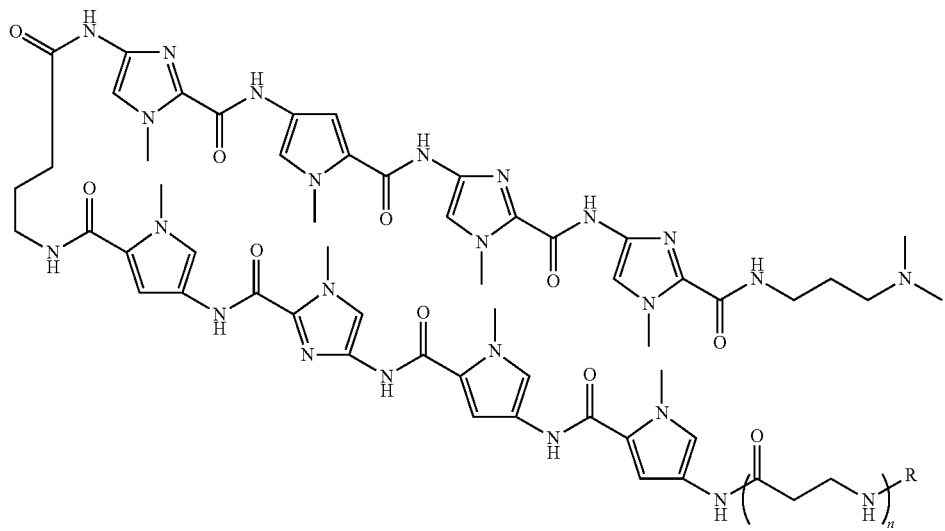
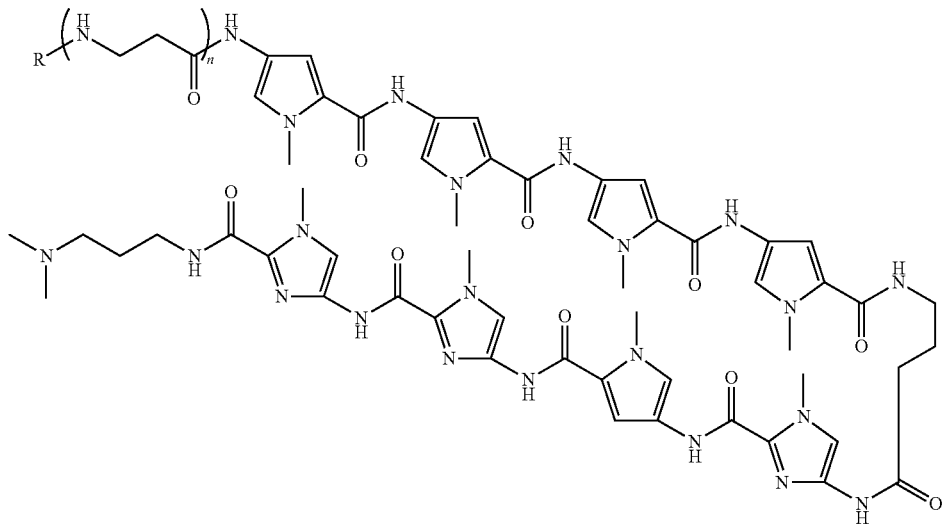

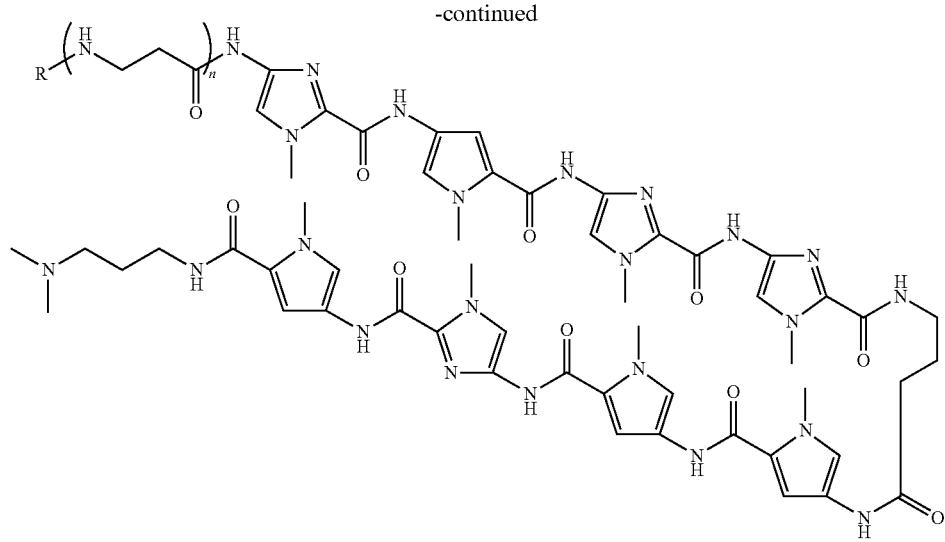

wherein,

R represents an acting agent, preferably an alkylating agent, and more preferably an alkylating agent selected from the group consisting of chlorambucil, duocarmycin, seco-CBI, pyrrolobenzodiazepine, and Nitrogen mustard, and n represents 0, 1, 2, 3, 4 or 5, preferably 1, 2 or 3, and more preferably n represents 1; and modified forms of the compounds.

Other preferred examples of the conjugate of an alkylating agent and a PI polyamide in the present invention include conjugates of chlorambucil and a PI polyamide represented by the following formula:

[Chemical formula 11]

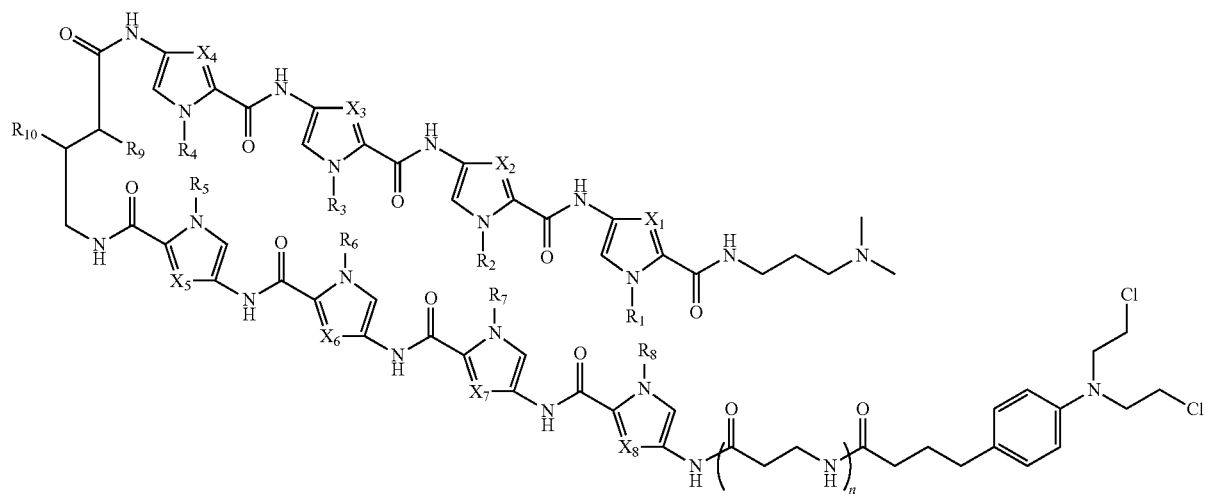

wherein, $X_1$ represents CH or N, $X_2$ represents CH or N, $X_3$ represents CH or N, $X_4$ represents CH or N, $X_5$ represents CH or N, $X_6$ represents CH or N, $X_7$ represents CH or N, $X_8$ represents CH or N, wherein $X_1$ to $X_8$ are selected in a combination that enables the PI polyamide to recognize a RUNX consensus sequence, $R_1$ represents H or alkyl, $R_2$ represents H or alkyl, $R_3$ represents H or alkyl, $R_4$ represents H or alkyl, $R_5$ represents H or alkyl, $R_6$ represents H or alkyl, $R_7$ represents H or alkyl, $R_8$ represents H or alkyl, $R_9$ represents H or $NHR_{11}$, $R_{10}$ represents H or $NHR_{11}$, $R_{11}$ represents H, or a molecule such as biotin or a fluorescent group, and n represents 0, 1, 2, 3, 4 or 5, preferably 1, 2 or 3, and more preferably n represents 1; and modified forms of the conjugates.

Further, other preferred examples of the above-described conjugate in the present invention include conjugates of chlorambucil and a PI polyamide represented by the following formulae:

[Chemical formula 12]
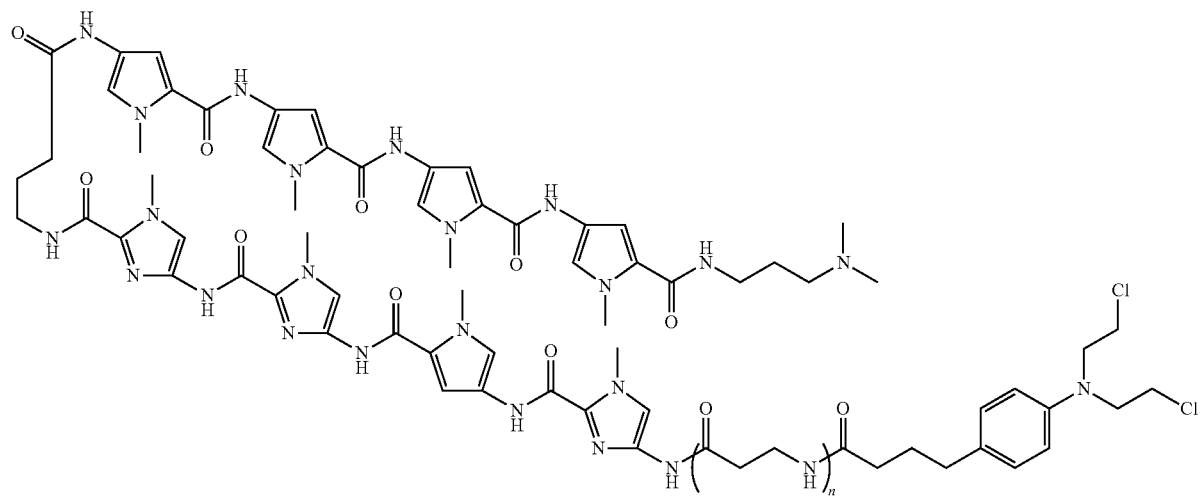
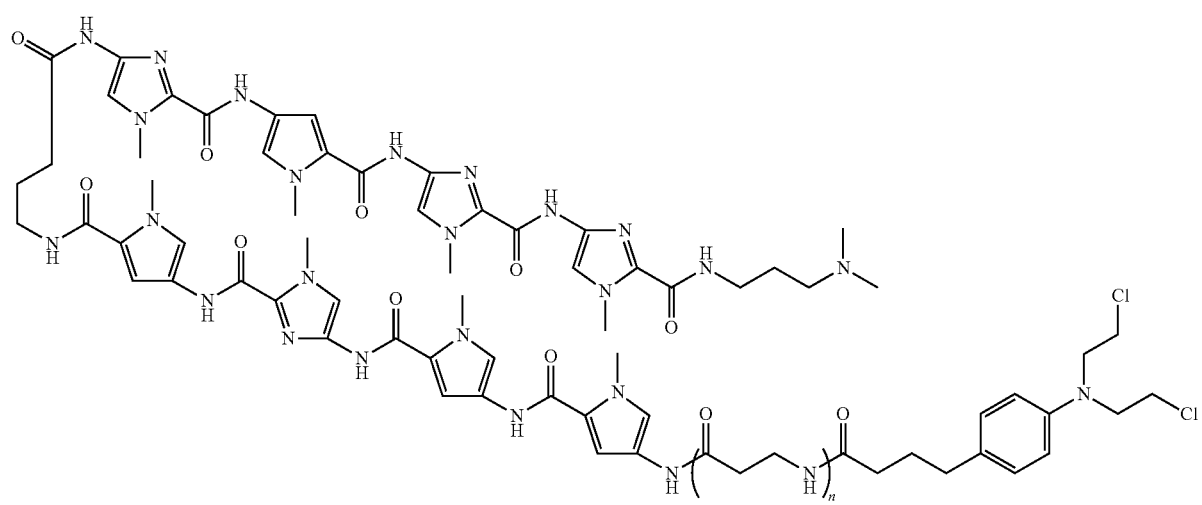
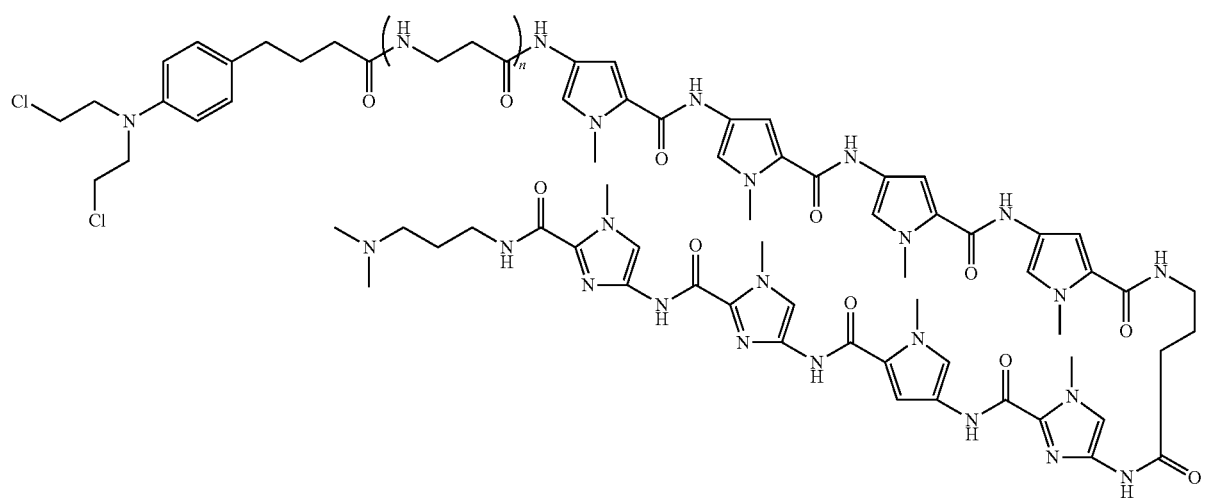

-continued

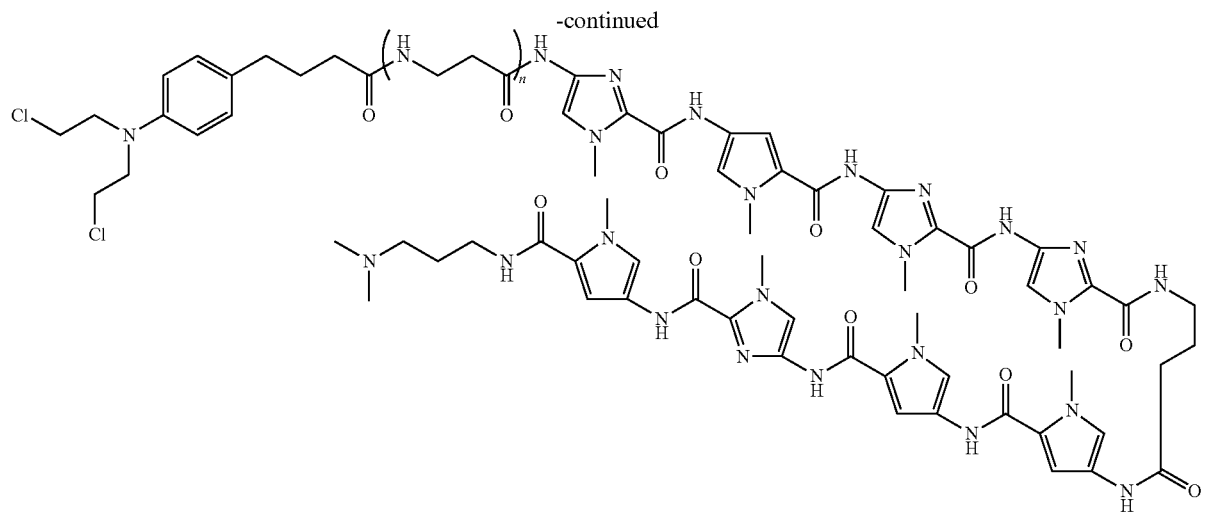

wherein, n represents 0, 1, 2, 3, 4 or 5, preferably 1, 2, or 3, and more preferably n represents 1; and modified forms of the conjugates.

The conjugate of an acting agent and a DNA binding compound, e.g. a PI polyamide, may be in the form of a pharmacologically acceptable salt. Examples of the pharmacologically acceptable salt include inorganic acid salts such as hydrochloride, sulfate, phosphate and hydrobromide, and organic acid salts such as acetate, fumarate, maleate, oxalate, citrate, methanesulfonate, benzenesulfonate and toluenesulfonate.

In the above-described conjugate, at least one moiety or molecule of the acting agent, the DNA binding compound, and/or the linker moiety linking the acting agent and the DNA binding compound may be present in the form of an enantiomer or diastereomer or a mixture thereof. The conjugate includes a mixture of stereoisomers, or a pure or substantially pure isomer thereof. When the conjugate is obtained in the forms of diastereomers or enantiomers, these diastereomers or enantiomers can be separated by a conventional method well known in the art, for example, chromatography or fractional crystallization.

The conjugate may be labeled with a radioisotope (e.g., $^{3}H$, $^{13}C$, $^{14}C$, $^{15}N$, $^{18}F$, $^{32}P$, $^{35}S$, $^{125}I$, or the like) or the like on at least one moiety or molecule of the acting agent, the DNA binding compound, and/or the linker moiety linking the acting agent and the DNA binding compound, or may be deuterated.

The RUNX inhibitor of the present invention may be the above-described DNA binding compound itself or the above-described conjugate itself of the DNA binding compound and the acting agent, or may contain a carrier or an additive in addition to the DNA binding compound or the conjugate, depending on an intended purpose. Examples of the carrier and the additive include, but not limited to, water, acetic acid, organic solvents, collagen, polyvinyl alcohol, polyvinylpyrrolidone, carboxyvinyl polymers, sodium carboxymethylcellulose, sodium polyacrylate, sodium alginate, water-soluble dextran, sodium carboxymethyl starch, pectin, methylcellulose, ethylcellulose, xanthan gum, gum arabic, casein, agar, polyethylene glycol, diglycerol, glycerol, propylene glycol, Vaseline, paraffin, stearyl alcohol, stearic acid, human serum albumin, mannitol, sorbitol, lactose, and surfactants. The amount of the DNA binding compound or the conjugate contained in the RUNX inhibitor of the present invention can be optionally adjusted depending on an intended purpose.

The RUNX inhibitor of the present invention recognizes and binds to a RUNX consensus binding sequence on a genome. The RUNX consensus binding sequence is a common binding sequence among the members of RUNX family. Thus, the RUNX inhibitor of the present invention inhibits all members of RUNX family. That is, when the RUNX inhibitor of the present invention binds to a RUNX consensus binding sequence on a genome, binding of the all members of the RUNX family to the RUNX binding sequence on the genome is inhibited, which results in inhibition of all activities caused by binding of the members of RUNX family to DNA. Examples of the activity that the RUNX family is involved in include various types such as, but not limited to, activation by transcriptional regulation of p53 suppressors (e.g., BCL11 and TRIM24) (that is, in cancer, tumor suppressor p53 is constantly suppressed by RUNX family), enhancement by transcriptional regulation of BCR-ABL, which is a causative protein of Philadelphia chromosome-positive acute lymphocytic leukemia (PhALL), enhancement of transcription of MLL-AF4 in MLL-AF4+FLT3-ITD acute myeloid leukemia, and enhancement by transcriptional regulation of oncogene c-Myc.

The present invention also provides a method for inhibiting activities of RUNX family which comprises using the RUNX inhibitor of the present invention. The method for inhibiting RUNX family of the present invention can inhibit not only a target gene regulated by RUNX1, RUNX2 or RUNX3 but also a gene cluster (a group of target genes) regulated by all members of the RUNX family collectively.

The amount of the RUNX inhibitor of the present invention used can be appropriately determined according to the intended purpose.

2. Pharmaceutical Composition

The pharmaceutical composition of the present invention is a composition comprising the RUNX inhibitor of the present invention. The pharmaceutical composition of the present invention preferably comprises a RUNX inhibitor comprising a PI polyamide or a conjugate of a PI polyamide with an acting agent. As described above, the RUNX inhibitor of the present invention recognizes and binds to a RUNX consensus binding sequence on a genome. The RUNX consensus sequence (RUNX family protein-binding sequence) is present in regulatory regions of various genes. The RUNX family members regulate the expression of various target genes by binding to the consensus sequence in the regulatory regions. The pharmaceutical composition of the present invention down-regulates the expression of various genes which are targeted by each RUNX family member, by binding to the RUNX consensus sequence. Examples of the target gene include, but not limited to, genes which are highly expressed in CBF leukemia (e.g., IL3, CSF2, CSF2RB, etc.), RUNX family itself (RUNX1, RUNX2, and RUNX3), p53 suppressors (e.g., BCL11, TRIM24, etc.), and c-kit genes.

Various diseases can be treated and prevented by administering the pharmaceutical composition of the present invention in vivo. The pharmaceutical composition of the present invention can be used for every organism, which utilizes double-stranded DNA in biocontrol, particularly mammals (e.g., human, rat, rabbit, sheep, pig, cattle, cat, dog, monkey, etc.).

Target diseases of the pharmaceutical composition of the present invention include all diseases which RUNX family members are involved in. An example of the target diseases of the pharmaceutical composition of the present invention includes cancer, and examples thereof include, but not limited to, leukemia (e.g., acute myeloid leukemia, acute lymphoblastic leukemia, and chronic myeloid leukemia), myelodysplastic syndrome-derived leukemia, lymphoma, myeloma, multiple myeloma, lung cancer, esophageal cancer, gastric cancer, colon cancer, renal cell cancer, neuroblastoma, breast cancer, skin cancer (e.g., melanoma), ovarian cancer, hepatoblastoma, osteosarcoma, Ewing's sarcoma, prostate cancer, pancreatic cancer, liver cancer, hepatoblastoma, osteosarcoma, rhabdomyosarcoma, ovarian cancer, uterine cancer, and brain tumor. As shown in Examples described later, since the RUNX inhibitor of the present invention activates a p53 pathway by regulating transcription of a p53 suppressor, the pharmaceutical composition of the present invention can theoretically suppress, treat, or prevent all cancers. Although the pharmaceutical composition of the present invention may not exert a sufficient antitumor effect on cancer having a p53 mutation when it is used alone, a synergistic anti-tumor effect on cancer having a p53 mutation is exerted when the pharmaceutical composition of the present invention is used in combination with a p53 inducer. Examples of the p53 inducer include 2,2-bis(hydroxymethyl)-1-azabicyclo[2.2.2]octan-3-one (PRIMA-1), 1-[(1-oxopropoxy)methyl]-1H-pyrrole-2,5-dione (MIRA-1), and Nutlin3.

The pharmaceutical composition of the present invention can be used as, for example, an anti-tumor agent or a differentiation inducer.

Further examples of the target diseases of the pharmaceutical composition of the present invention include mast cell diseases such as mast cell tumor and mastocytosis (e.g., mast cell proliferation disease, severe allergic disease, atopic dermatitis, anaphylactic shock, severe bronchia asthmatic attack, and severe dermatitis medicamentosa), various types of allergy, and immunological diseases. Mast cells are defined as cells expressing both FceRI, which is a receptor specific to an IgE antibody that is deeply involved in allergy, and c-kit, which is a receptor of a cytokine called a stem cell factor (SCF), on the cell surface. It is known that when mast cells are stimulated mechanically or chemically or come into contact with an allergen such as a heterologous protein, the mast cells degranulate and thereby release contents stored in the granules (e.g., histamine, heparin, etc.) into the extracellular environment, which causes an allergic reaction. As shown in Examples described later, since the RUNX inhibitor of the present invention inhibits the expression of c-kit (stem cell factor receptor tyrosine kinase) in mast cells, the pharmaceutical composition of the present invention can suppress, treat, or prevent all symptoms or diseases caused by activation of mast cells.

The pharmaceutical composition of the present invention may be in any of dosage forms for oral administration and parenteral administration. These dosage forms can be formulated according to a routine method and may contain a pharmaceutically acceptable carrier or additive. Examples of such a carrier and an additive include water, acetic acid, pharmaceutically acceptable organic solvents, collagen, polyvinyl alcohol, polyvinylpyrrolidone, carboxyvinyl polymers, sodium carboxymethylcellulose, sodium polyacrylate, sodium alginate, water-soluble dextran, sodium carboxymethyl starch, pectin, methylcellulose, ethylcellulose, xanthan gum, gum arabic, casein, agar, polyethylene glycol, diglycerol, glycerol, propylene glycol, Vaseline, paraffin, stearyl alcohol, stearic acid, human serum albumin, mannitol, sorbitol, lactose, and surfactants acceptable as pharmaceutical additives.

The additive is selected alone or in appropriate combination from those described above depending on the dosage form of the pharmaceutical composition of the present invention. Examples of the dosage form for oral administration include tablets, capsules, fine granules, powders, granules, solutions, syrups, sprays, liniments, eye drops, and preparations for external use. Alternatively, the oral administration may be performed in an appropriate dosage form. Examples of the dosage form for parenteral administration include injections. The injections can be administered systemically or locally by, for example, intravenous injection (e.g., drip infusion), subcutaneous injection, intraperitoneal injection, or intratumoral injection.

For example, for use as a preparation for injection, the pharmaceutical composition of the present invention is dissolved in a solvent (e.g., saline, a buffer solution, a glucose solution, 0.1% acetic acid, etc.), and this solution can be supplemented with an appropriate additive (human serum albumin, PEG, a mannose-modified dendrimer, a cyclodextrin conjugate, etc.) and used. Alternatively, the pharmaceutical composition of the present invention may be freeze-dried for a dosage form that is dissolved before use. For example, a sugar alcohol or a saccharide, such as mannitol or glucose, can be used as an excipient for freeze drying.

A dose of the pharmaceutical composition of the present invention differs depending on age, sex, symptoms, administration route, the number of administrations, and the dosage form. The dose, for example, for an adult human (60 kg) is 0.01 to 1,000 mg, preferably 0.1 to 100 mg, more preferably 1 to 30 mg, per day. The administration method is appropriately selected depending on the age and symptoms of a patient. The pharmaceutical composition of the present invention may be administered, for example, once every few days, once a day, or two to four times per day.

The pharmaceutical composition of the present invention may be used in combination with other anti-tumor agents. Examples of the other anti-tumor agents include any anti-tumor agent used for the treatment of a specific cancer, and a p53 inducer. Any known anti-tumor agent can be used as the other anti-tumor agents. Examples of known anti-tumor agent include cytarabine, imatinib, gefitinib, PRIMA-1, MIRA-1, and Nutlin3. An administration ratio of the pharmaceutical composition of the present invention to the other anti-tumor agents is not particularly limited, and may be appropriately determined by a person skilled in the art so that a desired antitumor effect can be achieved.

The present inventors have made RUNX1 knockdown mice using shRNA to investigate the roles of other RUNX family members when only RUNX1 is inhibited. As a result, it has been found that when RUNX1 is inhibited, the activity is compensated by those of other RUNX family members. Thus, the RUNX inhibitor and pharmaceutical composition of the present invention which can inhibit all RUNX family members can exert a stronger antitumor effect than when the expression of each RUNX member is individually reduced.

The present invention also provides a kit comprising the RUNX inhibitor of the present invention. The kit may contain, in addition to the RUNX inhibitor of the present invention, a pharmaceutically acceptable carrier or additive, reagents, auxiliary agents, a dedicated container, other necessary accessories, an instruction manual, etc. The kit of the present invention may be used, for example, as a kit for cancer therapy or a research reagent kit.

The present invention also provides use of CBFβ as a cancer marker. The present inventors have found that CBF is expressed in various cancers and the expression level correlates with the expression of RUNX family (Example 3). Thus, CBFβ can be used as a pan-cancer marker which can be used for detecting various cancers, and the presence of a cancer can be determined by detecting CBFβ in a sample from a subject.

Hereinafter, the present invention is further specifically explained by way of Examples which the present invention is not limited to.

EXAMPLES

Materials and methods used in Examples are described below.
Materials and Methods
Cell Lines AML cell lines of THP-1 and KG-1a, a CML cell line of K562, a lung cancer cell line of A549, and esophageal cancer cell lines of TE-1, TE-5 and TE-11 were purchased from RIKEN biological resource center (BRC), Japan. AML cell lines of Kasumi-1 and HL60, lung cancer cell lines of LU99A, ABC-1 and RERF-LC-MS, gastric cancer cell lines of MKN7 and MKN45, melanoma cell lines of C32TG and Mewo, a kidney cancer cell line of Caki-1, colon cancer cell lines of HCT116 and LOVO, and an embryonic kidney cell line of HEK293T cell were obtained from Japanese Collection of Research Bioresources (JCRB), Japan. AML cell lines of OCI-AML2, OCI-AML3 and MOLM13 were purchased from Deutsche Sammlung von Mikroorganismen and Zellkulturen GmbH (DSMZ), Germany. AML cell lines of MV4-11 and KG-1a, an ALL cell line of RS4; 11, lymphoma cell lines of SU-DHL-5, Raji and Dauji, a myeloma cell line of KMS-12-BM, a lung cancer cell line of NCI-H2228, and breast cancer cell lines of DU4475, MCF7, HCC1937, MDA-MB-231 and HTB-27 were obtained from American Type Culture Collection (ATCC), USA. ALL cell lines of SU-Ph2 and SU/SR cells were provided by Dr. A Kanamaru (Department of Internal Medicine, Kinki University School of Medicine, Osaka, Japan). An ALL cell line of KOCL-45 was provided by Dr. K. Sugita (Department of Pediatrics, Yamanashi University, Yamanashi, Japan). An AML cell line of MV4-11NR cells harboring a TP53 R248W mutation was provided by Dr T. Ikezoe (Department of Hematology and Respiratory Medicine, Kochi University, Kochi, Japan). Caki-1 and HEK293T cells were maintained in Dulbecco's modified eagle medium (DMEM) supplemented with 10% heat-inactivated fetal bovine serum (FBS) and 1% Penicillin-Streptomycin (PS) at 37° C., 5% $CO_2$. The other cell lines were cultured in a Roswell Park Memorial Institute (RPMI) 1640 medium containing 10% FBS and 1% PS at 37° C., 5% $CO_2$.

Cell Growth Curve

To assess cell proliferation, $1 \times 10^5$ cells of AML cell lines were transferred to a 6-well plate with 5 mL medium. For the expression of a tetracycline inducible gene or shRNA, doxycycline was added at 3 μM. The trypan blue exclusion assay was performed every other day to count cell number.
Real-time quantitative PCR (qRT-PCR)

A total RNA was isolated with RNeasy mini kit (Qiagen) and reverse transcribed with Reverse script kit (TOYOBO) to generate cDNA. Real-time quantitative polymerase chain reaction (PCR) was carried out with 7500 Real-Time PCR System (Applied Biosystems) according to the manufacturer's instructions. Results were normalized to GAPDH levels. Relative expression levels were calculated using the 2-ΔΔCt method. Primers used for qRT-PCR are shown in Table 1.

TABLE 1

| PCR primers used for qRT-PCR | | |
|---|---|---|
| Gene to be amplified | Forward (5' → 3') | Reverse (5' → 3') |
| GAPDH | CATGTTCGTCATGGGGTGAACCA (SEQ ID NO: 1) | AGTGATGGCATGGACTGTGGTCA T (SEQ ID NO: 2) |
| BCL11A | AACCCAGCACTTAAGCAAA (SEQ ID NO: 3) | GGAGGTCATGATCCCCTTCT (SEQ ID NO: 4) |
| TRIM24 | GCGCCTACTTTTATTTCTTTACT G (SEQ ID NO: 5) | AATGCTTTTGAGGCGTTTCTT (SEQ ID NO: 6) |
| IL3 | AATCTCCTGCCATGTCTGCC (SEQ ID NO: 7) | AGATCGCGAGGCTCAAAGTC (SEQ ID NO: 8) |
| CSF2RB | AGCCCAGATGCAGGGGA (SEQ ID NO: 9) | CCCAGGATGTCAGGTAGGGA (SEQ ID NO: 10) |
| p53 | CCCCTCCTGGCCCCTGTCATCTT C (SEQ ID NO: 11) | GCAGCGCCTCACAACCTCCGTCA T (SEQ ID NO: 12) |

TABLE 1-continued

PCR primers used for qRT-PCR

| Gene to be amplified | Forward (5' → 3') | Reverse (5' → 3') |
|---|---|---|
| CSF2 | GGCCAGCCACTACAAGCAGCACT (SEQ ID NO: 13) | CAAAGGGGATGACAAGCAGAAAG (SEQ ID NO: 14) |
| p21 | TGTGGACCTGTCACTGTCTTG (SEQ ID NO: 15) | AATCTGTCATGCTGGTCTGC (SEQ ID NO: 16) |
| BAX | CATGTTTTCTGACGGCAACTTC (SEQ ID NO: 17) | AGGGCCTTGAGCACCAGTTT (SEQ ID NO: 18) |
| PUMA | GCAGGCACCTAATTGGGCT (SEQ ID NO: 19) | ATCATGGGACTCCTGCCCTTA (SEQ ID NO: 20) |
| MDM2 | ACCTCACAGATTCCAGCTTCG (SEQ ID NO: 21) | TTTCATAGTATAAGTGTCTTTTT (SEQ ID NO: 22) |
| RUNX1 | CTGCTCCGTGCTGCCTAC (SEQ ID NO: 23) | AGCCATCACAGTGACCAGAGT (SEQ ID NO: 24) |
| RUNX2 | GGTTAATCTCCGCAGGTCACT (SEQ ID NO: 25) | CACTGTGCTGAAGAGGCTGTT (SEQ ID NO: 26) |
| RUNX3 | CAGAAGCTGGAGGACCAGAC (SEQ ID NO: 27) | GTCGGAGAATGGGTTCAGTT (SEQ ID NO: 28) |
| Pan_RUNX (RUNX1 + RUNX2 + RUNX3) | GCACCGACAGCCCCAACTT (SEQ ID NO: 29) | GTCTTGTTGCAGCGCCAGTG (SEQ ID NO: 30) |
| CBFB | TGTGAGATTAAGTACACGG (SEQ ID NO: 31) | TAATGCATCCTCCTGCTGGGCT (SEQ ID NO: 32) |

Immunoblotting

Cells were washed twice with ice cold phosphate-buffered saline (PBS) and harvested in protein lysis buffer [50 mM Tris (pH 7.4), 100 mM NaCl, 0.1 mM EDTA, 1 mM phenylmethylsulfonyl fluoride, 1 mM β-glycerophosphate, 2.5 mM sodium pyrophosphate, 1 mM $Na_3VO_4$, 1x protease inhibitor (Roche) and PhosSTOP (Roche)]. Whole cell extracts were separated by SDS-polyacrylamide gel electrophoresis (SDS-PAGE) and electrotransferred onto polyvinylidene difluoride membranes. Membranes were probed with the following antibodies: anti-Ctip1 antibody (Abcam, ab19487), anti-TRIM24 antibody (Bethyl Laboratories, Inc), anti-RUNX1 antibody (A-2), anti-GAPDH (FL-335), anti-p21 (C-19), anti-Bax (N-20) antibodies (Santa Cruz Biotechnology, Inc.), anti-RUNX2, anti-RUNX3, anti-p53 antibodies (Cell Signaling Technology), anti-CBFβ antibody (FL-182, Santa Cruz Biotechnology, Inc.), anti-cleaved caspase-3 antibody (5A1E, Cell Signaling Technology), anti-PARP antibody (46D11, Cell Signaling Technology). For secondary antibodies, anti-rabbit IgG, or anti-mosue IgG HRP-linked antibodies (Cell Signaling Technology) were used. Blots were detected using Chemi-Lumi One Super (nacalai tesque, Inc.) and ChemiDoc™ XRS+ Imager (Bio-Rad Laboratories, Inc.), as recommended by the manufacturers. Protein levels were quantified with Image Lab Software (Bio-Rad Laboratories, Inc.).

Analysis of Gene Expression Microarray

MV4-11 cells were treated with 1 μM of Chb-M', Chb-50 or DMSO for 6 hours before total RNA isolation. MV4-11 cells transduced with control shRNA (sh_Luc.) or shRNAs targeting RUNX1 (sh_Rx1 #1 and #2), RUNX2 (sh_Rx2) and RUNX3 (sh_Rx3) (see "siRNA interference" described later) were incubated with 3 μM doxycycline for 24 hours. Then total RNA was isolated from the cells. RNA extraction was conducted using RNeasy MINI Kit (Qiagen, Calif., USA) according to the manufacturer's instructions. The quality of the RNA samples was examined using the Agilent 2100 Bioanalyzer (Agilent Technologies, USA). The mRNA from total RNA samples was amplified into dsDNA. Cyanine 3-labeled cRNA was generated in the presence of T7 polymerase, purified using RNeasy Mini kits and its concentration was measured using Nanodrop ND1000 v3.5.2 (Thermo Scientific). The resultant cRNA (825 ng) was fragmented and subsequently hybridized to Human Gene 2.1 ST Array Strip (Affymetrix, USA). The raw data together with the associated sample information were processed by GeneSpring GX v12.1.0 (Agilent Technologies, USA). The microarray data have been deposited in NCBI's Gene Expression Omnibus and are accessible through GEO Series accession numbers. Gene Set Enrichment Analysis (GSEA) was utilized to analyze the microarray data obtained in the present study (Subramanian, A. et al. Gene set enrichment analysis: a knowledge-based approach for interpreting genome-wide expression profiles. Proc Natl Acad Sci USA 102, 15545-15550, doi:10.1073/pnas.0506580102 (2005)). Gene ontology enrichment analysis was conducted by Database for Annotation, Visualization and Integrated Discovery (DAVID) Bioinformatics Resources 6.7 software according to the provider's instructions (see Huang da, W., Sherman, B. T. & Lempicki, R. A. Systematic and integrative analysis of large gene lists using DAVID bioinformatics resources. Nat Protoc 4, 44-57, doi:10.1038/nprot.2008.211 (2009), and Huang da, W., Sherman, B. T. & Lempicki, R. A. Bioinformatics enrichment tools: paths toward the comprehensive functional analysis of large gene lists. Nucleic Acids Res 37, 1-13, doi:10.1093/nar/gkn923 (2009)).

siRNA Interference

Specific shRNAs (tetracycline-inducible short hairpin RNAs) targeting human RUNX1, RUNX2 and RUNX3 were designed and cloned into pENTR4-HltetOxl, CS-RfA-ETBsd, CS-RfA-ETV, CS-RfA-ETR vectors (RIKEN BioResource Ceneter). Nontargeting control shRNA was designed against luciferase (sh_Luc.). The target sequences are provided in Table 2.

TABLE 2

Target sequences for shRNA knockdown experiments

5' → 3'

| | |
|---|---|
| sh_RUNX1 #1 | AGCTTCACTCTGACCATCA (SEQ ID NO: 33) |
| sh_RUNX1 #2 | AACCTCGAAGACATCGGCA (SEQ ID NO: 34) |
| sh_RUNX2 | AAGGTTCAACGATCTGAGATTT (SEQ ID NO: 35) |
| sh_RUNX3 | AAGCAGCTATGAATCCATTGT (SEQ ID NO: 36) |
| sh_Luc. | CGTACGCGGAATACTTCGA (SEQ ID NO: 37) |

Statistics

Statistical significance of differences between groups was assessed with a 2-tailed unpaired Student's t test. Equality of variances in two populations was calculated with an F-test. Differences were considered statistically significant at a P value of less than 0.05. The results were represented as the average±SEM values obtained from three independent experiments. In transplantation experiments, animals were randomly allocated to each experimental group, and the treatments were given with blinding. The overall survival of mice is shown in a Kaplan-Meier curve. Survival between the indicated groups was compared using the log-rank test. To analyze the overall survival of cancer patients, PrognoScan software was utilized for data extraction and calculation of minimal P value (see Mizuno, H., Kitada, K., Nakai, K. & Sarai, A., BMC Med Genomics 2, 18, doi: 10.1186/1755-8794-2-18 (2009)). For the measurement of correlation between mRNA or protein expressions, the Spearman's rank correlation coefficient was used.

Mice

NOD/Shi-scid,IL-2RγKO (NOG) mice were purchased from the Central Institute for Experimental Animals, Japan. Littermates were used as controls in all experiments.

Example 1: Synthesis of PI Polyamides and Conjugates

PI polyamides that specifically recognize the RUNX consensus binding sequences 5'-TGTGGT-3' and 5'-TGCGGT-3' were designed and synthesized by successively linking four kinds of pyrrole-imidazole pairs (FIG. 1). Chb-M' targets 5'-TGTGGT-3', and Chb-50 targets 5'-TGCGGT-3'. As a control, a PI polyamide targeting sequence 5'-WGGCCW-3' (Chb-S) was synthesized (FIG. 1). Herein, W means A or T.

General

Reagents and solvents were purchased from standard suppliers and used without further purification. Flash column purifications were performed by a CombiFlash Rf (Teledyne Isco, Inc.) with C18 RediSep Rf Flash Column. Electrospray ionization time-of-flight mass spectrometry (ESI-TOF MS) was performed on a Bio-TOF II (Bruker Daltonics) mass spectrometer using positive ionization mode. Machine-assisted polyamide syntheses were performed on a PSSM-8 (Shimadzu) system with computer-assisted operation. Proton nuclear magnetic resonance ($^1$H NMR) spectra were recorded with a JEOL JNM ECA-600 spectrometer operating at 600 MHz and in parts per million (ppm) downfield relative to tetramethylsilane used as an internal standard. The following abbreviations apply to spin multiplicity: s (singlet), d (doublet), t (triplet), q (quartet), quint (quintet), m (multiplet).

Synthesis of Chb-M'

A PI polyamide supported by oxime resin was prepared in a stepwise reaction by Fmoc solid-phase protocol. The product with oxime resin was cleaved with N,N-dimethyl-1,3-propane diamine (1.0 mL) at 45° C. for 3 hours. The resin was removed by filtration. The residue was dissolved in the minimum amount of dichloromethane and washed with diethyl ether to yield a 59.6 mg. To the crude compound (59.6 mg, 48.1 µmol), a solution of chlorambucil (32.6 mg, 107 µmol), PyBOP (benzotriazole-1-yl-oxy-tris-pyrrolidino-phosphonium hexafluorophosphate) (101 mg, 195 µmol), and N,N-diisopropylethylamine (100 µL, 581 µmol) in N,N-dimethylformamide (DMF) (300 µL) was added. The reaction mixture was incubated for 1.5 hours at room temperature, washed with diethyl ether and DMF for three times, and dried in vacuo. The crude product was purified by reversed-phase flash column chromatography (water with 0.1% trifluoroacetic acid/MeCN). After lyophilization, a product was obtained (30.2 mg, 19.8 µmol). The alkylating agent chlorambucil conferred stronger and irreversible DNA binding ability to the PI polyamide.

The other conjugates were prepared by the same procedure.

Chb-M'

$^1$H NMR (600 MHz, DMSO (dimethyl sulfoxide)-d6): δ=10.43 (s, 1H), 10.30 (s, 1H), 9.92 (s, 1H), 9.90 (s, 1H), 9.894 (s, 1H), 9.890 (s, 1H), 9.83 (s, 1H), 9.44 (s, 1H), 8.30 (t, J=6.2 Hz, 1H), 8.15 (t, J=6.2 Hz, 1H), 7.86 (t, J=5.9 Hz, 1H), 7.63 (s, 1H), 7.52 (s, 1H), 7.44 (s, 1H), 7.39 (d, J=2.0 Hz, 1H), 7.22 (d, J=1.4 Hz, 2H), 7.18 (d, J=1.3 Hz, 1H), 7.17 (d, J=1.3 Hz, 1H), 7.15 (d, J=1.3 Hz, 1H), 7.073 (d, J=2.1 Hz, 1H), 7.066 (d, J=2.0 Hz, 1H), 6.98 (d, J=8.9 Hz, 2H), 6.95 (d, J=2.0 Hz, 1H), 6.88 (d, J=1.4 Hz, 1H), 6.62 (d, J=8.9 Hz, 2H), 4.01 (s, 3H), 3.96 (s, 3H), 3.94 (s, 3H), 3.87 (s, 3H), 3.84 (s, 6H), 3.83 (s, 3H), 3.81 (s, 3H), 3.67 (m, 8H), 3.32-3.23 (m, 6H), 3.07 (m, 2H), 2.79 (d, J=4.8 Hz, 6H), 2.52 (m, 2H), 2.40 (apparent t, J=7.6 Hz, 2H), 2.28 (apparent t, J=7.2 Hz, 2H), 2.04 (apparent t, J=7.4 Hz, 2H), 1.82 (m, 4H), 1.70 (m, 2H). ESI-TOF-MS m/z calcd for $C_{71}H_{90}Cl_2N_{24}O_{11}^{2+}$ [M+2H]$^{2+}$ 762.3293, 763.3279, found 762.3277, 763.3244.

Chb-50

$^1$H NMR (600 MHz, DMSO-d6): δ=10.38 (s, 1H), 10.29 (s, 1H), 10.22 (s, 1H), 9.99 (s, 1H), 9.920 (s, 1H), 9.916 (s, 1H), 9.86 (s, 1H), 9.42 (s, 1H), 8.48 (t, J=6.2 Hz, 1H), 8.06 (t, J=5.5 Hz, 1H), 7.87 (t, J=5.8 Hz, 1H), 7.63 (s, 1H), 7.545 (s, 1H), 7.538 (s, 1H), 7.46 (s, 1H), 7.37 (s, 1H), 7.32 (s, 1H), 7.21 (s, 1H), 7.19 (s, 1H), 7.17 (s, 1H), 7.08 (s, 1H), 6.99 (d, J=7.6 Hz, 2H), 6.98 (s, 1H), 6.89 (s, 1H), 6.63 (d, J=8.2 Hz, 2H), 4.01 (s, 3H), 3.98 (s, 3H), 3.97 (s, 3H), 3.96 (s, 3H), 3.87 (s, 3H), 3.86 (s, 3H), 3.82 (s, 3H), 3.81 (s, 3H), 3.68 (m, 8H), 3.30 (apparent quint, J=6.2 Hz, 4H), 3.21 (apparent q, J=6.2 Hz, 2H), 3.07 (m, 2H), 2.78 (d, J=4.8 Hz, 6H), 2.43-2.34 (m, 6H), 2.05 (t, J=7.6 Hz, 2H), 1.86 (quint, J=7.6 Hz, 2H), 1.80 (quint, J=7.6 Hz, 2H), 1.71 (quint, J=7.6 Hz, 2H). ESI-TOF-MS m/z calcd for $C_{70}H_{89}Cl_2N_{25}O_{11}^{2+}$ [M+2H]$^{2+}$ 762.8270, 763.8255, found 762.8247, 763.8251.

Chb-S $^1$H NMR (600 MHz, DMSO-d6): δ=10.34 (s, 2H), 10.33 (s, 1H), 10.32 (s, 1H), 9.93 (s, 2H), 9.33 (s, 1H), 9.31 (s, 1H), 8.15 (t, J=5.5 Hz, 1H), 8.04 (t, J=5.2 Hz, 1H), 7.89 (t, J=5.5 Hz, 1H), 7.58 (s, 2H), 7.55 (s, 1H), 7.52 (s, 1H), 7.26 (s, 2H), 7.17 (s, 4H), 6.97 (d, J=7.6 Hz, 2H), 6.95 (s, 1H), 6.91 (s, 1H), 6.61 (d, J=7.6 Hz, 2H), 4.01 (s, 6H), 3.99 (s, 3H), 3.98 (s, 3H), 3.85 (s, 6H), 3.813 (s, 3H), 3.807 (s, 3H), 3.66 (m, 8H), 3.32 (q, J=6.2 Hz, 2H), 3.23 (m, 4H), 3.06 (m, 2H), 2.79 (d, J=3.4 Hz, 6H), 2.52 (m, 2H), 2.38 (m, 4H), 2.04 (t, J=7.5 Hz, 2H), 1.82 (m, 4H), 1.70 (m, 2H).

ESI-TOF-MS m/z calcd for $C_{70}H_{89}Cl_2N_{25}O_{11}^{2+}$ [M+2H]$^{2+}$ 762.8270, 763.8255, found 762.8247, 763.8230.

Example 2: Cluster Regulation of RUNX Family with PI Polyamide Conjugate (1) Inhibition of Expression of RUNX1 Target Gene Inhibition of expressions of RUNX1 target genes were confirmed at mRNA levels using PI polyamides conjugated with an alkylating agent chlorambucil (Chb-M' and Chb-50) by the Real-time quantitative PCR (qRT-PCR) method. Briefly, MV4-11 cells were treated with 5 μM Chb-M' or Chb-50 for 6 hours. A total RNA was extracted from the treated cells, and then subjected to qRT-PCR (see the above-described "Real-time quantitative PCR (qRT-PCR)") to quantify the expression levels of IL3, CSF2 and CSF2RB which were target genes of RUNX1. As a control, the cells treated with DMSO were used. Values obtained from the cells treated with each PI polyamide conjugate were normalized to that of the DMSO treated cells (n=3).

Results are shown in FIG. 2. Chb-M' and Chb-50 effectively inhibited the expressions of RUNX1 target genes (IL3, CSF2, and CSF2RB) (FIG. 2).

(2) Inhibition of Expression of BCL11A and TRIM24

Inhibition of expression of the following genes were demonstrated at mRNA levels in the same manner as described in above (1) except that 1 μM Chb-M' and Chb-50 were used: BCL11A and TRIM24 known as suppressors of p53, both of which were reported to degrade p53 protein either directly or indirectly; and p21, BAX, PUMA and MDM2 which are downstream target genes of p53. Results are shown in FIG. 3.

Further, inhibition of expressions of BCL11A, TRIM24, p21, BAX, PUMA and MDM2, and PARP and a cleaved form of PARP, and cleaved caspase-3 were demonstrated at protein levels by the Western blotting method (see the above-described "Immunoblotting"). Briefly, MV4-11 cells were treated with 1 μM Chb-M' or Chb-50 for 24 hours. The treated cells were dissolved in the protein lysis buffer. Whole cell extracts were resolved by SDS-polyacrylamide gel electrophoresis (SDS-PAGE) and transferred onto polyvinylidene difluoride membranes. The membranes were probed with each antibody. Blots were detected and quantified. As a control, the cells treated with DMSO were used. Results are shown in FIG. 4.

The results show that the gene expressions of p53 suppressors BCL11A and TRIM24 were down-regulated by treatment with Chb-M' and Chb-50 (FIG. 3). While the mRNA expression level of p53 was unchanged, the mRNA expression levels of p21 (cell cycle checkpoint gene) and PUMA (apoptotic factor) were increased (FIG. 3). At protein levels, the expression levels of protein p53 and downstream proteins of p53 (p21, BAX) were increased by treatment with Chb-M' and Chb-50, and the expression levels of suppressors of p53 (BCL11A and TRIM24) were reduced (FIG. 4). These results reveal that the increased expression level of p53 proteins by Chb-M' and Chb-50 results from enhanced stability of p53 protein rather than enhanced transcription of the gene. Further, the emergence of cleaved form of PARP and cleaved caspase-3 (FIG. 4) shows that the enhancement of p53 expression level induced apoptosis.

(3) Analysis of Gene Expression Pattern by Regulation of RUNX Family

Gene expression patterns were demonstrated at genome levels using PI polyamides conjugated with an alkylating agent chlorambucil (Chb-M' and Chb-50) by microarray analysis (see the above-described "Analysis of gene expression microarray"). Briefly, MV4-11 cells were treated with 1 μM Chb-M' or Chb-50 for 6 hours. Top 500 up-regulated genes and top 500 down-regulated genes in the cells were compared with transcripts in MV4-11 cells in which RUNX family was knockdown. As a result, the gene expression patterns in the cells treated with Chb-M' and Chb-50 significantly correlated to those in cells in which all members of RUNX family (RUNX1, RUNX2 and RUNX3) were knockdown.

(4) Growth Inhibition Assay of Cancer Cells

Growth inhibition of some AML cell lines expressing functional p53 (MV4-11, OCI-AML2, OCI-AML3 and MOLM-13) by PI polyamide conjugates at different concentrations was tested. Briefly, the cells were placed at a density of 1×10$^5$ cells/mL. Different concentrations of a PI polyamide conjugate (Chb-M' or Chb-50) were added to media, and the cells were incubated for 48 hours (n=3). The number of viable cells when the PI polyamide conjugate was not added was used as a control (DMSO control). Cell viability was assessed by counting the viable cells with Cell Count Reagent SF (Nacalai tesque, Inc.) and Infinite (registered trademark) 200 PRO multimode reader (TECAN) according to the manufacturer's instructions. Dose-response curves thus obtained are shown in FIG. 5. As a result, Chb-M' and Chb-50 were highly effective against the above-mentioned AML cells at between nanomolar to low micromolar levels.

(5) Inhibition Effects on Various Cancer Cells

The effects of Chb-M' and Chb-50 on cancer cells of diverse origins were investigated. Specifically, 50% inhibition concentrations (IC$_{50}$) of Chb-M' and Chb-50 were calculated in the following cancer cells expressing functional p53: AML cells (MV4-11, OCI-AML2, OCI-AML3, MOLM13), ALL cells (SU-Ph2, SU/SR, RS4-11), lymphoma cells (SU-DHL-5), myeloma cells (KMS-12-BM), lung cancer cells (A549, LU99A, NCI-H2228), gastric cancer cells (MKN45), esophageal cancer cells (TE1), breast cancer cells (HTB-27, DU4475, MCF7), melanoma (C32TG), kidney cancer cells (Caki-1), and colon cancer cells (HCT116, LOVO). Briefly, the cells were cultured to a density of 1×10$^5$ cells/mL. Different concentrations of Chb-M' or Chb-50 were added to media and the cells were incubated for 48 hours (n=3). Cell viability was assessed by counting the viable cells with Cell Count Reagent SF (nacalai tesque, Inc.) and Infinite (registered trademark) 200 PRO multimode reader (TECAN) according to the manufacturer's instructions. Doses that inhibited 50% proliferation (IC$_{50}$ were analyzed by the median-effect method (Chou, T. C. & Talalay, P. Quantitative analysis of dose-effect relationships: the combined effects of multiple drugs or enzyme inhibitors. Adv Enzyme Regul 22, 27-55 (1984)). Further, the same test was performed using various cancer cells harboring mutated p53 or no p53 (hereinafter, collectively referred to as "p53-mutated cancer cells"). As the p53-mutated cancer cells, AML cells (MV4-11NR, HL60, ME1, KG1a, THP1, Kasumi-1, NB4, K562), ALL cells (KOCL-45), lymphoma cells (Raji, Dauji), lung cancer cells (ABC-1), gastric cancer cells (MKN7), melanoma cells (Mewo), breast cancer cells (HCC1937, MDA-MB-231), and esophageal cancer cells (TE5, TE11) were used.

Results are shown in FIG. 6 (Chb-M') and FIG. 7 (Chb-50). As clearly shown from FIGS. 6 and 7, these PI polyamide conjugates were marvelously effective against cancer cells of diverse origins, including acute myeloid leukemia (AML), acute lymphoblastic leukemia (ALL), lymphoma, myeloma, lung cancer, gastric cancer, esophageal cancer, breast cancer, melanoma, kidney cancer and colon cancer. Particularly, in many of the cancer cells expressing wild type p53 and a part of the p53-mutated cancer cells, Chb-M' or Chb-50 administration inhibited cell growth with $IC_{50}$ values of 5 µM or less. Chb-M' was generally more potent than Chb-50, probably because Chb-M' targets the major binding sequences of RUNX while Chb-50 targets the minor ones.

(5) Effect of Concomitant Use with p53 Inducer

These PI polyamide conjugates were found to have their reduced potency in many of the tested p53-mutated cancer cells as compared with the cancer cells expressing functional p53 (FIGS. 6 and 7). We examined the effect of concomitant use of the conjugates and a p53 inducer. Specifically, MV4-11NR, HL60, KG1a, THP-1 and Kasumi-1 cells were cultured in the presence of different concentrations of Chb-M' alone or p53 inducer PRIMA-1 alone, or combination of different concentrations of Chb-M' and 5 µM PRIMA-1 for 48 hours (n=3); and $IC_{50}$ values were calculated. KG1a and HL60 cells are null for p53 (p53null cell lines). MV4-11NR, Kasumi-1 and THP-1 cells harbor mutated p53 (p53mut(+) cell lines). $IC_{50}$ values obtained in each cell are shown in Table 3.

TABLE 3

| Cell | Status of p53 | IC50 (µM) of PRIMA-1 single agent administration | IC50 (µM) of Chb-M' single agent administration | IC50 (µM) of Chb-M' in concomitant use with PRIMA-1 (5 µM) |
|---|---|---|---|---|
| KG1a | p53null | >100 | >100 | >100 |
| HL60 | p53null | 5.74 | 11.4 | 11.7 |
| Kasumi-1 | p53mut(+) | 7.03 | >100 | 0.359 |
| THP-1 | p53mut(+) | 6.00 | >100 | 0.5 |
| MV4-11NR | p53mut(+) | 5.50 | >100 | 0.00103 |

In KG1a and HL60, the $IC_{50}$ values of Chb-M' were unchanged by concomitant use of PRIMA-1, and no effect of the concomitant use was found. In Kasumi-1, THP-1 and MV4-11NR, the necessary amount of Chb-M' was dramatically reduced by concomitant use of PRIMA-1.

Next, to quantify the effect of concomitant use of Chb-M' and PRIMA-1, combination index (CI) theorem of Chou-Talalay was calculated using COMPUSYN software (Chou, T. C. Theoretical basis, experimental design, and computerized simulation of synergism and antagonism in drug combination studies. Pharmacol Rev 58, 621-681, doi: 10.1124/pr.58.3.10 (2006)). CI value<1 is considered statistically significant, which means synergism effect. Plots of CI values against a rate of suppressed cells (Fa: fraction affected) are shown in FIG. 8. The CI value of each cell when Fa was 0.5 is shown in Table 4.

TABLE 4

| Cell | Status of p53 | CI (Fa = 0.5) |
|---|---|---|
| KG1a | p53null | 2.01 |
| HL60 | p53null | 1.10 |
| Kasumi-1 | p53mut(+) | 0.156 |
| THP-1 | p53mut(+) | 0.249 |
| MV4-11NR | p53mut(+) | 0.380 |

As clearly shown from the above-described results, the concomitant used of Chb-M' with a p53 inducer PRIMA-1 showed stronger inhibition effect on cell proliferation than that of single-agent administration of the p53 inducer or Chb-M', and showed synergistic inhibition effect on cell proliferation. Further, the same experiments were performed using a p53 inducer MIRA-1 and the same results were obtained. Although the PI polyamide conjugates of the present invention may greatly reduce their potency in p53 mutated cells (cancer cells harboring mutated p53 or no p53), concomitant use with a p53 inducer enables suppression of such p53 mutated cells. These results suggest that the mechanism for exerting the antitumor effect of Chb-M' is different from that for a p53 inducer.

(6) In Vivo Antitumor Effect

1. Safety Test of PI Polyamide Conjugate

To check the pharmacological safety of the PI polyamide conjugates in vivo, acute toxicological testing of Chb-M' in mice was first performed. NOD/Shi-scid,IL-2RγKO (NOG) mice were injected with Chb-M' at various concentrations. Complete blood cell counts, blood biochemistry and body weight were measured (n=5). Results are shown in FIG. 9. A 10 mg/kg body weight injection of Chb-M' resulted in slight decrease of platelets counts (FIG. 9 (*a*)). This dose is more than thirty times higher than the necessary amount to gain medicinal effect of the PI polyamide conjugate, assuring that this molecule is highly tolerable in vivo.

2. Creation of Xenograft Mouse Model

To investigate in vivo anti-tumor effects of Chb-M' and Chb-50, xenograft mouse models of human cancer cell lines were created using NOG mice. For leukemia mouse models, $2.5 \times 10^6$ cells/body of MV4-11 or SU/SR cells were intravenously injected. Peripheral blood (PB) was collected every week and chimerism was checked by using an anti-human CD45 antibody (BD Biosciences). At day 7, each treatment was started. For creating a lung cancer mouse model, $1 \times 10^6$ cells/body of A549 cells were injected via a retro-orbital vein. The lung cancer cells were transduced with luciferase-expressing lentivirus produced by pLenti-luciferase vector (addgene) for cell trafficking. D-Luciferin (Wako Pure Chemical Industries, Ltd.) was injected peritoneally at 150 mg/kg body weight, and the amount of tumor volume was assessed by IVIS Spectrum In Vivo Imaging System (PerkinElmer) every week. For the creation of gastric cancer xenograft mouse model, $1 \times 10^6$ cells/body of MKN45 cells were injected subcutaneously at the right dorsal flank. The gastric cancer cells were marked with luciferase, and tumor growth was monitored by IVIS.

3. Antitumor Effect in AML Mouse Model

The xenogfaft AML mouse model created in above 2 was, 7 days after transplantation, intravenously injected with 320 µg/kg body weight of Chb-M' or Chb-50 twice a week to examine their efficacy (n=7). As controls, the mice were treated with a solvent (dimethyl sulfoxide; DMSO) (320 µg/kg body weight, twice a week IV injections), chlorambucil (320 µg/kg body weight, twice a week IV injections), Chb-S (320 µg/kg body weight, twice a week IV injections), and cytarabine (Ara-C) (Wako Pure Chemical Industries, Ltd.) (i.p. injections of 100 mg/kg body weight, 5 consecutive days (from day 7 through day 11)). At 14 days, bone marrow, liver and spleen tissues were removed from the AML mice, and subjected to hematoxylin and eosin staining (hereinafter, also referred to as "H&E staining") and immunohistochemical staining with an anti-human CD45 antibody (hereinafter, also referred to as "hCD45 staining"), and microscopic images were taken. The H&E staining stains hematopoietic tissues. The hCD45 staining stains human hematopoietic dells with brown and does not stain mouse tissues.

Results of survival tests of mice by each treatment are shown in FIG. 10. As evident from FIG. 10, the treatment with Chb-M' or Chb-50 potently (about 2 times or more) lengthened the overall survival periods in the fms-related tyrosine kinase 3 (FLT3) mutation positive poor-prognostic AML model.

Regarding the H&E staining of the bone marrow from the mice transplanted with MV4-11 cells, administration of DMSO, cytarabine, or Chb-S resulted in little change, and the tissue was filled with homogeneous leukemia cells (magnification 4× and 20×). When Chb-M' was administered, the homogeneity was lost, and the image moved toward a normal bone marrow image (WT) (FIG. 11-1 and FIG. 11-2). Regarding the hCD45 staining, the bone marrow tissue from the mouse treated with DMSO, cytarabine, or Chb-S administration was filled with leukemia cells (because the cells are human cells, they are stained with brown in hCD45 staining) (FIG. 11-1 and FIG. 11-2). In contrast, when Chb-M' was administered, most of the brown parts lost and unstained cells (mouse bone marrow cells) occupied most all of the tissue (FIG. 11-1 and FIG. 11-2). Thus it was found that AML cells from human are lost by Chb-M' administration.

Regarding the hCD45 staining of the liver tissue from the mice transplanted with MV4-11 cells, when DMSO, cytarabine, Chb-S or Chb-M' was administered, the tissue was not stained with brown like the tissue from a non-transplanted mouse (WT). Thus, it was found that AML cells hardly invaded liver. In spleen tissue, the same result was observed.

MV4-11 cells show a resistance to a currently available anticancer agent cytarabine. The PI polyamide conjugates of the present invention were effective in vivo even against such cancer that was resistant to the conventional anticancer agent.

4. Antitumor Effect in ALL Mouse Model

The xenograft ALL mouse model created in above 2 was intravenously injected with 320 μg/kg body weight of Chb-M' twice a week to examine its efficiency (n=5). As controls, the mice were treated with DMSO (320 μg/kg body weight, twice a week IV injections), and imatinib. The treatment with imatinib was performed by oral administration of 100 mg/kg body weight of imatinib mesylate (Focus Biomolecules) twice a day from day 7 until the recipient mice died from the disease. In the same manner as described in above 3, bone marrow, liver and spleen tissues were removed from the ALL mice, and subjected to H&E staining and hCD45 staining, and microscopic images were taken. Results of survival tests of mice by each treatment are shown in FIG. 12. Microscopic images of each tissue from ALL mice receiving each treatment are shown in FIG. 13 (bone marrow), FIG. 14 (liver), and FIG. 15 (spleen).

As evident from FIG. 12, the treatment with Chb-M' potently (about 1.8 times) lengthened the overall survival periods even in the xenograft ALL mice created with Philadelphia chromosome-positive (Ph+) cells (SU/SR cells).

Regarding the H&E staining of the bone marrow tissue from the xenograft ALL mice, administration of DMSO or imatinib resulted in little change, and the tissue was filled with homogeneous leukemia cells (magnification 4× and 20×). When Chb-M' was administered, the homogeneity was lost, and the image moved toward a normal bone marrow image (FIG. 13). Regarding the hCD45 staining, the tissue from the mouse treated with DMSO or imatinib administration was filled with leukemia cells (because the cells are human cells, they are stained with brown in hCD45 staining). However, when Chb-M' was administered, most of the brown parts lost and unstained cells (mouse bone marrow cells) occupied most all of the tissue (FIG. 13). That is, it was found that PhALL cells from human were rather diminished by Chb-M' administration.

Regarding the hCD45 staining of the liver tissue from the xenograft ALL mice, the tissue was stained with brown in the DMSO-administered group (FIG. 14). This indicates that transplanted human leukemia cells invaded liver. Since the tissue from the mice treated with imatinib administration was also stained with brown by hCD45 staining, it was found that invasion of liver by the transplanted human phALL cells was not inhibited by imatinib administration. On the other hand, regarding hCD45 staining of the tissue from the mice treated with Chb-M' administration, brown PhALL cells were reduced. Thus, it was found that invasion of liver by cancer cells was reduced by Chb-M' administration (FIG. 14). Of course, regarding tissue from mice (WT) not transplanted with human cancer cells, tissue stained with brown was not observed. In spleen tissue, the same results were observed (FIG. 15).

SU/SR cells have a T315I mutation which delivers a resistance to currently available tyrosine kinase inhibitors (e.g., imatinib). The PI polyamide conjugate of the present invention was effective in vivo even against such cancer that was resistant to the conventional anticancer agents.

5. Antitumor Effect in Lung Cancer Mouse Model

Treatment of the xenograft lung cancer mouse model created in above 2 with Chb-M' (320 μg/kg body weight, twice a week IV injections), DMSO (320 μg/kg body weight, twice a week IV injections), or gefitinib (100 mg/kg body weight, fifth a week oral administrations) was started 7 days after transplantation (n=5). From day 7 after transplantation, luciferin was intraperitoneally injected every week, and engraftment of the transplanted lung cancer cells was checked by IVIS imaging. In addition, lung tissue was removed from the lung cancer mice at day 14 after transplantation, and subjected to H&E staining and immunohistochemical staining with an anti-human Ki-67 antibody, and microscopic images were taken. Results are shown in FIGS. 16 to 19.

As evident from FIG. 16, the treatment with Chb-M' potently (about 2 times) lengthened the overall survival periods even in the xenograft lung cancer mice created with a gefitinib-resistant lung adenocarcinoma cell line (A549 cells).

Further, as evident from IVIS images of the lung cancer mice receiving each treatment, at day 7 after transplantation of the human lung cancer cells (before administration of each drug), engraftment of the transplanted cancer cells in lung was confirmed (FIG. 17, upper images). Regarding mice at day 14 after transplantation of the human lung cancer cells (after 2 administrations of each drug), in the DMSO-administered group and the gefitinib-administered group, the lung cancer cells densely proliferated in lung and the brightness of luciferase increased (FIG. 17, middle images). On the other hand, regarding the Chb-M'-administered mice at day after transplantation, the brightness of luciferase rather weakened as compared with that at day 7 after transplantation (FIG. 17, middle images). Regarding the mice at day 21 after transplantation (after total 4 drug-administrations), in the DMSO-administered group and the gefitinib-administered group, the lung cancer cells further proliferated and the brightness of luciferase increased (i.e., the total volume of the tumor in lung increased) (FIG. 17, lower images). On the other hand, regarding the Chb-M'-administered mice, the brightness of luciferase further weakened (FIG. 17, lower images). In addition, quantification of bioluminescence signal intensity in IVIS images at day 21 after transplantation showed that the intensity was far lower in the mice treated with Chb-M' than in the mice treated with DMSO or gefitinib administration (FIG. 18).

Regarding H&E staining of the lung tissue from human lung cancer-transplanted mice, in the DMSO-administered group and the gefitinib-administered group, pulmonary alveoli were densely filled with lung cancer cells and the pulmonary alveoli contained little air (lung cancer was densely packed), so that ventilation of air in the pulmonary alveoli was not possible (FIG. 19, upper 2 rows). In the Chb-M'-administered group, the densely packed lung cancer cells were rather diminished and pulmonary alveoli were pneumatized (similar to the image of normal pulmonary alveoli without transplantation (WT)) (FIG. 19, upper 2 rows).

A549 is a human lung cancer cell line that is resistant to currently clinically available standard tyrosine kinase inhibitors against epidermal growth factor receptors (EGFR), such as gefitinib and erlotinib. Actually, gefitinib did not show effect on the lung cancer model (FIGS. 16 to 19). In contrast, Chb-M' inhibited the growth of lung cancer cells in vivo, and finally lengthened the overall survival periods as compared with the DMSO- or gefitinib-administered group (FIG. 16). Thus, it was shown that Chb-M' had a strong antitumor effect and exerted the effect on gefitinib-resistant lung cancer.

6. Antitumor Effect in Gastric Cancer Mouse Model

Treatment of the xenograft gastric cancer mouse model created in above 2 with Chb-M' (320 µg/kg body weight, twice a week IV injection) or with the same amount of DMSO was started 7 days after transplantation (n=8). From day 7 to day 35 after transplantation, luciferin was intraperitoneally injected twice a week, and tumor growth was monitored by IVIS imaging. In addition, the tumor graft was removed from the gastric cancer mice at day 35 after transplantation, and the gastric cancer volume was determined based on the height, width, and depth dimensions. Results are shown in FIGS. 20 to 22.

As evident from FIG. 20, in the Chb-M'-administered group, the tumor growth was inhibited and there was almost no change in tumor size from just after transplantation. This was also confirmed from the size of the tumor graft removed from mice at day 35 after transplantation (FIG. 22). In addition, from IVIS images, engraftment of the transplanted cancer cells was confirmed at day 7 after transplantation (before drug administration) (FIG. 21, upper images). At day 21 after transplantation (after total 4 drug-administrations), gastric cancer grew in the DMSO-administered group, whereas the size of gastric cancer decreased in the Chb-M'-administered group (FIG. 21, middle images). At day 35 after transplantation (after total 8 drug-administrations), gastric cancer further grew in the DMSO-administered group, whereas, though gastric cancer slightly grew in the Chb-M'-administered group, the growth was far less than that in the DMSO-administered group (FIG. 21, lower images).

MKN45 is a human gastric cancer cell line resistant to Her2 inhibitors (drugs whose indications include Her2-positive gastric cancer). The PI polyamide conjugate of the present invention was effective in vivo even against such cancer that was resistant to the conventional anticancer agents.

Example 3: CBFβ as a Novel Pan-Cancer Marker which Reflects Total RUNX Amount

To target whole RUNX family members for treatment of cancer, the expression variance of RUNX1, RUNX2, RUNX3 and CBFβ in cancer tissues and their normal counterparts was checked. Based on previously reported array data sets (Reference database for gene Expression Analysis; RefExA) (Ge, X. et al. Interpreting expression profiles of cancers by genome-wide survey of breadth of expression in normal tissues. Genomics 86, 127-141, doi: 10.1016/j.ygeno.2005.04.008 (2005)), expressions of CBFβ were consistently higher among cancer tissues compared to their normal counterparts, while each RUNX expression was variable between cancers and their normal counterparts. Intriguingly, however, when total RUNX expressions (RUNX1+RUNX2+RUNX3) in AML cells (MV4-11, MOLM-13, OCI-AML2, OCI-AML3, MV4-11NR, HL60, THP-1, KG1a, Kasumi-1) were quantified using primers for detecting the common region of RUNX1-3 by the above-described "Real-time quantitative PCR (qRT-PCR)" method, they were positively correlated to the expressions of CBF (FIG. 23). This phenomenon was also observed at protein levels by the above-described "Immunoblotting" method (FIG. 24). Thus, it was shown that the CBFβ expression may be a surrogate marker for the expression of all RUNX family members which are targets of the PI polyamide conjugate of the present invention. CBFβ was actually one of the most up-regulated genes at mRNA level in various cancer tissues, underscoring the feature of CBFβ as a tumor marker of a wide variety of cancers.

Next, the protein expressions of CBFβ in cancer cell lines of various origins and in their normal counterparts were explored. AML cells (MV4-11, MOLM-13, OCI-AML2, OCI-AML3, MV4-11NR, HL60, THP-1, KG-1a, Kasumi-1), ALL cells (SU-Ph2, SU/SR, RS4; 11, KOCL-45), lung cancer cells (PC-3, Lu99a, A549), breast cancer cells (DU4475, MCF-7, HTB-27, MDA-MB-231, HCC1937), kidney cancer cells (A498, 7860, Caki-1), and melanoma cells (C32TG, Mewo) were used. Immunoblotting of CBFβ elucidated that expressions of CBFβ are consistently higher among cancer cells than their normal counterparts at protein levels as well. Furthermore, it was found that in patients with AML, multiple myeloma, breast cancer, lung cancer, colorectal cancer, bladder cancer, ovarian cancer, prostate cancer and melanoma, the overall survival of the patients having high-level expression of CBFβ was lower than that of the patients having low-level expression of CBFβ. Thus, it was shown that expressions of CBFβ may be a novel prognostic marker across various types of cancer, including AML, multiple myeloma, breast cancer, lung cancer, colorectal cancer, bladder cancer, ovarian cancer, prostate cancer and melanoma.

Example 4: Inhibition Effect on CML (Chronic Myeloid Leukemia) and PhALL (Philadelphia Chromosome-Positive Acute B-Cell Leukemia)

CML and PhALL are leukemia caused by BCR-ABL fusion protein. Effects of Chb-M' and Chb-50 on CML and PhALL cells were examined. As CML cells, BV173 cell line and MYL cell line (provided by Department of Hematology and Respiratory Medicine, Saga Medical School) were used. Both BV173 and MYL are cell lines harboring wild-type p53 and wild-type p210BCR-ABL. As PhALL cells, SU-Ph2 cell line and SU/SR cell line were used. SU-Ph2 is a cell line harboring wild-type p190BCR-ABL. SU/SR is a tyrosine kinase inhibitor-resistant cell line harboring mutated p190BCR-ABL having a T351I point mutation.

(1) Inhibition of Expression of BCR-ABL Fusion Protein

To BV173 cells, MYL cells, SU-Ph2 cells, and SU/SR cells, 3 µM or 1 µM of Chb-M' was administered. After 6 hours, a total RNA was extracted from the cells, and then subjected to qRT-PCR (see the above-described "Real-time quantitative PCR (qRT-PCR)") to quantify the expression levels of BCR-ABL gene. As a control, DMSO was administered. Results of MYL cells, and SU-Ph2 cells and SU/SR cells are shown in FIGS. 25-1 and 25-2. In the figures, the expression levels are shown as values relative to the mRNA level of p210BCR-ABL or the mRNA level of p190BCR-ABL in the DMSO (control)-administered group.

To BV173 cells, MYL cells, SU-Ph2 cells, and SU/SR cells, 3 µM or 1 µM of Chb-M' were administered. After 24 hours, proteins were extracted, and then subjected to the Western blotting method (see the above-described "Immunoblotting") using an ABL antibody to confirm expressions of BCR-ABL fusion protein at protein levels. As a control, DMSO was administered. Results of MYL cells, and SU-Ph2 cells and SU/SR cells are shown in FIGS. 26-1 and 26-2.

As evident from FIG. 25-2, in the Chb-M'-treated SU-Ph2 and SU/SR cells, the mRNA levels of p190BCR-ABL decreased. As evident from FIG. 25-1, in the Chb-M'-treated MYL cells, the mRNA level of p210BCR-ABL decreased. Similarly, in the Chb-M'-treated BV173 cells, the mRNA level of p210BCR-ABL decreased. Accordingly, Chb-M' suppressed BCR-ABL fusion protein at a transcriptional level. In addition, as evident from FIG. 26-2, p190BCR-ABL fusion protein was lost in the Chb-M'-administered cells as compared with the DMSO (control)-administered cells. As evident from FIG. 26-1, p210BCR-ABL fusion protein was lost in the Chb-M'-administered cells as compared with the DMSO (control)-administered cells. Similarly, in the Chb-M'-administered group of BV173 cells, p210BCR-ABL fusion protein was lost as compared with the DMSO (control)-administered cells. Accordingly, Chb-M' suppressed BCR-ABL fusion protein at a protein level.

Further, by ChIP (chromatin immunoprecipitation) assay, it was confirmed that RUNX1 bound to a promoter region of BCR. Accordingly, it was found that Chb-M' binds to a RUNX consensus sequence that is present in the promoter region of BCR, and suppresses BCR-ABL fusion protein at a transcriptional level.

In addition, in MYL cells treated with Chb-M', the expressions of Bcl2 and C-Myc at protein levels were confirmed by the Western blotting method (see the above-described "Immunoblotting"). Bcl2 is the most downstream apoptotic suppressor of BCR-ABL fusion protein. It is known that C-Myc is an expression product of oncogene c-Myc, and C-Myc is transcriptionally induced in CML. Results are shown in FIG. 26-3.

In addition, 1.5 µM or 3 µM of Chb-M' was administered to MYL cells. After 48 hours, the percentage of apoptosis was analyzed by PI-AnnexinV apoptosis staining. As a result, early apoptosis rates were increased dependent on the concentration of Chb-M' (FIG. 26-4).

(2) Cell Growth Inhibition Assay

Different concentrations of Chb-M' were added to media, and MYL cells were incubated for 48 hours. Different concentrations of various drugs (Chb-50, Chb-M', or imatinib) were added to media, and SU-Ph2 cells and SU/SR cells were incubated for 48 hours. Cell viability after 48 hours was determined using. Cell Count Reagent SF (nacalai tesque, Inc.) and Infinite (registered trademark) 200 PRO multimode reader (TECAN), and IC50 values (viability of 50%) were calculated (MTS assay using SF reagent). Results are shown in FIG. 27-1 and FIG. 27-2.

As evident from FIG. 27-1 and FIG. 27-2, the PI polyamide conjugate of the present invention showed inhibition effect on cell proliferation of CML cells and PhALL cells. Further, as evident from FIG. 27-2, Chb 50 and Chb-M' showed lower IC50 values than that of imatinib (tyrosine kinase inhibitor) in both SU/Ph2 and SU/SR. Particularly, since SU/SR cell line is an imatinib-resistant strain, imatinib showed a high 1050 value of 14.76 µM, whereas Chb-50 and Chb-M' showed low values of 1.42 µM and 0.044 µM, respectively. Thus, both Chb-50 and Chb-M' dramatically inhibited the tyrosine kinase-resistant strain.

As described above, the RUNX inhibitor of the present invention was effective against leukemia caused by BCR-ABL fusion protein.

Example 5: Effects on Bone Marrow Niche

Bone marrow niches are important spaces for homing of leukemia cells. A vascular endothelium niche and an osteoblastic niche are two important niches in the bone marrow niches. E-selectin is an important factor which is expressed only in the vascular endothelial niche of bone marrow.

(1) Inhibition of Expression of E-Selectin

HUVEC (human umbilical vein endothelial cell line) (ATCC catalogue Number: ATCC CRL-1730) was treated with different concentrations (0 µM, 0.5 µM, 1 µM, or 5 µM) of Chb-M' for 6 hours. HUVEC is a cell line whose proliferation is not inhibited by Chb-M' ($IC_{50}$ value: 50 µM or more). After 6 hours, a total RNA was extracted from the cells, and then subjected to qRT-PCR (see the above-described "Real-time quantitative PCR (qRT-PCR)" to quantify the expression levels of E-selectin gene. As controls, the expression levels of P-selectin, Tie2, ICAM-1, VCAM-1, and Jagged-1 genes were quantified. Results are shown in FIG. 28. In the figure, relative mRNA expression levels of the genes are graphed when the mRNA expression levels of the genes in the cells treated with Chb-M' 0 µM (i.e., control (DMSO)) are 1. E-selectin 1 and E-selectin 2 were quantified with two types of RT-PCR primers for RE-selectin.

As evident from FIG. 28, E-selectin, P-selectin, and VCAM-1 were markedly suppressed by Chb-M' at mRNA levels.

(2) In Vitro Change in Expression Level of E-Selectin

Using HUVEC, changes in expression levels of E-selectin by the RUNX inhibitor and RUNX knockdown were analyzed by FACS (fluorescence-activated cell sorter). To HUVEC, 1 µM of Chb-M' was administered. After 24 hours, different antibodies were used for immunostaining and changes in the cell surface expression of CD62E (E-selectin) were measured. As a control, DMSO was administered. In addition, HUVEC in which RUNX1 gene expression was knockdown by sh_RUNX1 #2 were immunostained using different antibodies to measure changes in the cell surface expression of CD62E (E-selectin). As a control, the cells were knockdown by a siRNA targeting luciferase (sh_Luc.). As the antibodies, an anti-human CD62E (E-selectin) antibody (manufactured by eBioscience) and an isotype antibody (mouse IgG1) of anti-human CD62E (E-selectin) antibody (manufactured by eBioscience) were used.

Results are shown in FIG. 29. The upper graph of FIG. 29 shows the results of Chb-M' administration and the lower graph shows the results of RUNX1 knockdown. In the upper graph, "DMSO" indicates the result of staining of the DMSO-treated cells with the anti-human CD62E (E-selectin) antibody, "Chb-M'" indicates the result of staining of the Chb-M'-treated cells with the anti-human CD62E (E-selectin) antibody, "Isotype DMSO" indicates a negative control of the DMSO-treated cells stained with the isotype antibody (mouse IgG1) of anti-human CD62E (E-selectin) antibody, and "Isotype Chb-M'" indicates a negative control of the Chb-M'-treated cells stained with the isotype antibody (mouse IgG1) of anti-human CD62E (E-selectin) antibody. In the lower graph, "sh.Luc E-Selectin" indicates a negative control of control Luc shRNAi cells stained with the anti-human CD62E (E-selectin) antibody, "sh.Rx1 #2E-Selectin" indicates results of the sh_RUNX1-treated cells stained with the anti-human CD62E (E-selectin) antibody, "sh.Luc Isotype" indicates a negative control in which the cells were stained with the isotype antibody (mouse IgG1) of anti-human CD62E (E-selectin) antibody, and "sh.Rx1 #2_Isotype" indicates a negative control in which the cells were stained with the isotype antibody (mouse IgG1) of anti-human CD62E (E-selectin) antibody.

As evident from FIG. 29, both treatment with Chb-M' and treatment with sh_RUNX1 resulted in decrease in the expression of E-selectin as compared with the controls. In addition, by ChIP assay, it was confirmed that the RUNX consensus sequence was present in the SELE promoter of E-selectin. Thus, it was found that Chb-M' inhibits binding of RUNX1 to the SELE promoter, which is an E-selectin gene, and this leads to decrease in the expression level of E-selectin, which is an adhesion molecule present in a vascular niche.

(3) In Vivo Change in Expression Level of E-Selectin

Changes in expression levels of E-selectin in bone marrow endothelial cells by Chb-M' administration were examined in vivo. To normal mice, DMSO (control) or Chb-M' was administered 6 times over 2 weeks (320 µg/kg per administration). Twenty-four hours after the last administration (in a state in which Chb-M' had been eliminated from the body of the mouse), the femur and tibia were harvested, from them bone marrow hematopoietic cells were removed, and endothelial cells were collected and subjected to FACS analysis. CD45 negative cells (bone marrow cells without bone marrow hematopoietic cells) were gated, and a ratio between CD31 positive cells (vascular endothelial marker-positive) and Lin-negative CD45-negative CD31-positive E-selectin-positive cells (E-selectin-positive bone marrow vascular endothelial cells) was analyzed by FACS. A schematic illustration of the experiment scheme is shown in FIG. 30. Results are shown in FIG. 31.

As evident from FIG. 31, the E-selectin expression levels in the endothelial cells were significantly decreased in the Chb-M'-administered group. That is, Chb-M' suppressed the expression of E-selectin in bone marrow vascular endothelial cells in vivo.

(4) Homing Assay

Migration of leukemia stem cells to a specific distant site is called "homing effect". In this experiment, leukemia stem cells were transplanted by intravenous injection, and then the number of the leukemia stem cells migrating to bone marrow and surviving in a microenvironment was measured.

Mouse bone marrow (B6) was transfected with an MLL-ENL leukemia fusion gene using a retroviral vector. The transfected cells were repeatedly subcultured to obtain immortalized mouse leukemia cells (MLL-ENL leukemia cells labelled with GFP). To normal B6 mice, DMSO (control) or Chb-M' was administered 6 times over 2 weeks (320 µg/kg per administration). Twenty-four hours after the last administration (in a state in which Chb-M' had been eliminated from the body of the mouse: the half-life of the polyamide is about 5 hours), the mice were subjected to irradiation, and injected with $1 \times 10^7$ MLL-ENL leukemia cells from tail vein. After 24 hours, bone marrow cells from the right femur and left femur and spleen were harvested, and the numbers of MLL-ENL cells present in the bone marrow and the spleen were analyzed by FACS. A schematic illustration of the experiment scheme is shown in FIG. 32. Results are shown in FIG. 33.

As evident from FIG. 33, in the Chb-M'-treated group, the number of MLL-ENL cells in bone marrow was smaller than that in the control group. That is, it was found that when E-selectin decreased, it became difficult for leukemia stem cells (MLL-ENL-GFP) to survive in bone marrow. On the other hand, in the Chb-M'-treated group, the number of leukemia cells increased in spleen. Accordingly, it was found that it became difficult for leukemia cells to exist in bone marrow.

From the above-described results, it was found that the RUNX inhibitor of the present invention is effective not only against leukemia cells but also against a microenvironment (niche) side to which the leukemia cells adhere. Thus, it is suggested that the RUNX inhibitor of the present invention enhances the effect of an anticancer drug and is effective for eliminating small residual lesions in bone marrow niches.

Example 6: Effects on Her2-Positive Gastric Cancer

In Her2-positive gastric cancer, PI3-AKT signal and MAPK-ERK signal are enhanced by Her2, which is an RTK (Receptor Tyrosine Kinase), to increase cell proliferation. Her2 is regulated by GRB2-SOS1 adaptor protein beneath cell membrane. When the adaptor protein is enhanced and activated, Her2 is phosphorylated and kept activated.

To an MKN45 gastric cancer cell line (Her2 inhibitor-resistant cell line), 1 µM of Chb-M' was administered. After 48 hours, the protein expressions of Her2, p-ERK, ERK, p-AKT, and AKT were evaluated by the Western blotting method (see the above-described "Immunoblotting"). As a control, DMSO was administered. Results are shown in FIG. 34.

To the MKN45 gastric cancer cell line, 0.1 µM, 1 µM, or 10 µM of Chb-M' was administered. After 48 hours, the protein expressions of SOS1, p-Her2 (phospho-Her2), and Her2 were evaluated by the Western blotting method (see the above-described "Immunoblotting"). As a control, DMSO was administered. Results are shown in FIG. 35.

To the MKN45 gastric cancer cell line, 1 µM of Chb-M' was administered. After 6 hours, the mRNA level of SOS1 was evaluated by RT-PCR method using qRT-PCR (see the above-described "Real-time quantitative PCR (qRT-PCR)"). As a control, DMSO was administered. Results are shown in FIG. 36. In the figure, the mRNA expression level of SOS1 is shown as a value relative to that in the DMSO-treated group.

As evident from FIG. 34, though the expression of Her2 protein was suppressed by Chb-M', the total amounts of ERK protein and AKT protein were not changed. On the other hand, the phosphorylated forms of ERK protein and AKT protein were suppressed by Chb-M', and signals of p-ERK (phosphorylated ERK) and p-AKT (phosphorylated AKT) were reduced. In addition, as evident from FIG. 35 and FIG. 36, Chb-M' suppressed the expression of SOS1 and the phosphorylation of Her2. Thus, it was found that Chb-M' suppresses RUNX1 to suppress the expression of Her2 protein, and also suppresses the expression of SOS1 adaptor protein to suppress the phosphorylation of Her2.

Example 7: Effects on EGFR Wild-Type Lung Adenocarcinoma [EGFR Inhibitor (Gefitinib)-Resistant Lung Cancer Cell Line]

(1) Effects on EGFR Wild-Type p53 Wild-Type Lung Adenocarcinoma Cell Line

Different concentrations of various drugs (Chb-M', gefitinib, or chlorambucil) were added to media, and EGFR wild-type p53 wild-type lung adenocarcinoma cell lines (A549 and LU99A) were incubated for 48 hours. Cell viability after 48 hours was determined using Cell Count Reagent SF (nacalai tesque, Inc.) and Infinite (registered trademark) 200 PRO multimode reader (TECAN), and IC50 values (viability of 50%) were calculated (MTS assay using SF reagent). Results are shown in FIG. 37.

As evident from FIG. 37, Chb-M' showed lower IC50 values than those of the EGFR inhibitor (gefitinib) in both the A549 cell line and LU99A cell line. Thus, the RUNX inhibitor of the present invention was effective against EGFR wild-type non-small-cell lung cancer.

(2) Effects on EGFR Wild-Type p53-Mutated Lung Adenocarcinoma Cell Line

Different concentrations of various drugs (Chb-M', gefitinib, chlorambucil, or Chb-S) were added to media, and EGFR wild-type p53-mutated lung adenocarcinoma cell lines (ABC-1 and RERF-LC-MS) were incubated for 48 hours. Cell viability after 48 hours was determined using Cell Count Reagent SF (nacalai tesque, Inc.) and Infinite (registered trademark) 200 PRO multimode reader (TECAN), and IC50 values (viability of 50%) were calculated (MTS assay using SF reagent). Results are shown in FIG. 38.

As evident from FIG. 38, Chb-M' showed lower IC50 values than those of the EGFR inhibitor (gefitinib) in both the ABC-1 cell line and RERF-LC-MS cell line. However, the anti-tumor activity was slightly decreased as compared with effects on p53 wild-type lung adenocarcinoma cell lines (A549 cells and LU99A cells) (FIG. 37).

(3) Effects on EGFR Signal

To LU99A cells and A549 cells, 1 µM Chb-M' was administered. After 24 hours, the expression of Mig6 protein was evaluated by the Western blotting method (see the above-described "Immunoblotting"). As a control, DMSO was administered. Results are shown in FIG. 39.

As evident from FIG. 39, in both LU99A cells and A549 cells, the expression levels of Mig6 were enhanced by Chb-M'. Mig6 is known as a factor negatively regulating the signal of EGFR. Thus, the RUNX inhibitor of the present invention suppresses EGFR wild-type lung adenocarcinoma, probably through enhancement of Mig6.

(4) Apoptosis Inducing Effect

To A549 cells and LU99A cells, 1 µM Chb-M' was administered. After 24 hours, the expression levels of apoptosis-related factors (p53, p21, PUMA, and BAX) were evaluated by the Western blotting method (see the above-described "Immunoblotting"). As a control, DMSO was administered. Results are shown in FIG. 40. In the figure, "C-M" means the Chb-M'-administered group.

As evident from FIG. 40, p53 and p21 and apoptotic factors such as PUMA and BAX were enhanced by Chb-M'. Thus, it was shown that the RUNX inhibitor of the present invention induced apoptosis in lung cancer cells.

Example 8: Effect on Human Mast Cell

Mast cells cause symptoms or diseases such as allergic reaction by receptor-mediated activation. In addition, c-kit signal transduction enhances release of chemical mediators from stimulated mast cells. The effect of the RUNX inhibitor on human mast cells was examined. As human mast cells, a LAD2 cell line (expressing wild-type c-kit) and an HMC-1.2 cell line (expressing mutated c-kit) were used. The HMC-1.2 cell line has KIT D816V mutation and V560G mutation. Wild-type c-kit is a SCF receptor and the cell proliferation is dependent on SCF. Accordingly, regarding the LAD2 cell line, 50 ng/ml of SCF was administered and experiments were performed as described below. The HMC-1.2 cell line has a mutation in c-kit and the cell proliferation is independent of SCF. Accordingly, regarding the HMC-1.2 cell line, SCF was not administered and experiments were performed as described below. As the RUNX inhibitor, Chb-M' was used. The LAD2 cell line was provided by Dr. Kirshenbaum A. S. and Dr. Metcalfe D. D. (Laboratory of Allergic Diseases, NIAID, NIH). The HMC-1.2 cell line, which was established by Dr. Nilsson G. (Department of Genetics and Pathology, Uppsala University), was provided by Dr. Metcalfe D. D. (Laboratory of Allergic Diseases, NIAID, NIH).

(1) Effect on Cell Surface Expression of KIT

To the LAD2 cell line, 10 µM Chb-M' was administered. After 3 hours and 18 hours, different antibodies were used for immunostaining of c-kit expressed on the cell surface, and the expression levels were analyzed by FACS (fluorescence-activated cell sorter). To the HMC-1.2 cell line, 10 µM Chb-M' was administered. After 18 hours, different antibodies were used for immunostaining of c-kit expressed on the cell surface, and the expression levels were analyzed by FACS. As a control, the same experiments were carried out using DMSO instead of Chb-M'. As the antibodies, an anti-human CD117 (c-kit) antibody (clone 104D2, manufactured by BioLegend) and a mouse IgG1, K isotype Ctrl (FC) antibody (clone MOPC-21, manufactured by BioLegend) were used.

Results are shown in FIG. 41. In the figure, "DMSO" indicates the results of DMSO-treated cells stained with the anti-human c-kit antibody. "Chb-M'" indicates the results of Chb-M'-treated cells stained with the anti-human c-kit antibody. "Isotype control, DMSO" indicates the results of negative controls in DMSO-treated cells stained with the isotype antibody of the anti-human c-kit antibody. "Isotype control, Chb-M'" indicates the results of negative controls in Chb-M'-treated cells stained with the isotype antibody of the anti-c-kit antibody. "MFI" indicates mean fluorescent intensity.

As evident from FIG. 41, treatment with Chb-M' led to decrease in the surface expression levels of c-kit in both the LAD2 cell line (wild-type c-kit) and HMC-1.2 cell line (mutated c-kit) after 18-hour treatment. That is, in the LAD2 cell line, MFI after 18-hour treatment with DMSO was 68.3, whereas MFI after 18-hour treatment with Chb-M' was 48.8. In the HMC-1.2 cell line, MFI after 18-hour treatment with DMSO was 113, whereas MFI after 18-hour treatment with Chb-M' was 100. Based on these experiments, it was found that Chb-M' suppresses the cell surface expression of c-kit (both wild-type c-kit and mutated c-kit) in mast cells.

(2) Effect on Total Amount of KIT

To the LAD2 cell line and the HMC-1.2 cell line, 10 μM Chb-M' was administered. After culturing the cells for 18 hours, extracts were obtained from the cells, and the protein expression levels of c-kit, phospho-c-Kit, AKT, phosphorylated AKT, Mitf, and GAPDH were analyzed by the Western blot analysis (see the above-described "Immunoblotting") using different antibodies. AKT is an important signaling protein downstream of c-kit. Mitf is a representative transcriptional driver for c-kit. As a control, DMSO was administered. Results are shown in FIG. 42. In the figure, "KIT" indicates c-kit, "pKIT" indicates phosphorylated c-kit, and "pAKT" indicates phosphorylated AKT. As primary antibodies, an anti-c-Kit antibody (Ab81, manufactured by Cell Signaling Technology), an anti-phospho-c-Kit (Tyr719) antibody (manufactured by Cell Signaling Technology), an anti-Akt antibody (manufactured by Cell Signaling Technology), an anti-phospho-Akt antibody (Ser473) (manufactured by Cell Signaling Technology), an anti-Mitf antibody (manufactured by Cosmo Bio), and an anti-GAPDH antibody (0411, manufactured by Santa Cruz Biotechnology, Inc.) were used. As secondary antibodies, an ECL™ anti-mouse IgG horseradish peroxidase-linked whole antibody (manufactured by GE Healthcare) and an ECL™ anti-rabbit IgG linked whole antibody (manufactured by GE Healthcare) were used.

As evident from FIG. 42, in the LAD2 cell line, the expression of c-kit protein was suppressed by Chb-M', and phospho-c-Kit protein, which is the active form of c-kit, was also suppressed by Chb-M'. Although the total amount of AKT was not considerably changed by Chb-M', the level of phosphorylated AKT protein was decreased by Chb-M'. The protein expression level of Mitf was not affected by Chb-M'.

In the HMC-1.2 cell line, the expression levels of c-kit and phospho-c-Kit were suppressed by Chb-M'. It has been reported that mutated c-kit is generally transported to endolysosomes rather than cell membrane, and activates Akt. Regarding the HMC-1.2 cell line, in view of the results of FACS as shown in the above-described (1), it was thought that c-kit in cytoplasm was predominantly reduced. Actually, as shown in FIG. 42, since the HMC-1.2 cell line treated with Chb-M' clearly decreased in the total amount of c-kit, it was found that intracellular c-kit was suppressed by Chb-M' in the HMC-1.2 cell line. In addition, regarding pAKT, a slight decrease in the amount of protein was observed.

On the basis of the above results, it was found that, regarding wild-type c-kit, Chb-M' leads to a marked decrease in the total amount of c-kit and suppresses the downstream signal of c-kit. On the other hand, it was confirmed that, regarding mutated c-kit, Chb-M' significantly suppresses cytoplasmic c-kit protein rather than that on the cell surface. Based on these experiments, it was found that Chb-M' leads to decrease in the total amount of c-kit (both wild-type c-kit and mutated c-kit) in mast cells.

Further, by ChIP assay, it was confirmed that RUNX1 bound to intron 1 of c-kit in mast cells (HMC-1.2 cell line). Thus, it was found that Chb-M' suppresses c-kit protein, which is indispensable to cell proliferation in mast cells, at a transcriptional level. Thus, Chb-M' can regulate an allergic reaction in mast cells. In addition, Chb-M' led to decrease in the expression of c-kit in mast cells having mutated c-kit (HMC-1.2 cell line), and led to suppression of cell proliferation.

From the above-described results, it is suggested that RUNX1 regulates the expression of c-kit and can be a novel therapeutic target in human mast cells diseases.

Example 9: Effect on Colon Cancer

Different concentrations of various drugs (Chb-M' or chlorambucil) were added to media, and p53-mutated colon cancer cell line HT29 (purchased from JCRB Cell Bank) was incubated for 72 hours. Cell viability after 72 hours was determined using Cell Count Reagent SF (nacalai tesque, Inc.) and Infinite (registered trademark) 200 PRO multimode reader (TECAN) (FIG. 43), and IC50 values (viability of 50%) were calculated (MTS assay using SF reagent) (Table 5). As evident from FIG. 43, Chb-M' inhibited the proliferation of HT29 cells.

TABLE 5

| Reagent | IC50 (μM) |
| --- | --- |
| Chlorambucil | Not measurable |
| Chb-M' | 2.92 |

Example 10: Effect on Prostatic Adenocarcinoma (1) Cell Growth Inhibition Assay

Different concentrations of various drugs (Chb-M', Chb-S, chlorambucil, or Enzalutamide) were added to media, and prostatic adenocarcinoma cell line PC-3 (p53null/PTEN del/androgen-independent) (purchased from ATCC), DU-145 (androgen-independent) (purchased from JCRB Cell Bank), and LNCaP (androgen-dependent) (purchased from ATCC) were incubated for 48 hours. Cell viability after 48 hours was determined using Cell Count Reagent SF (nacalai tesque, Inc.) and Infinite (registered trademark) 200 PRO multimode reader (TECAN), and IC50 values (viability of 50%) were calculated (MTS assay using SF reagent). Results are shown in FIG. 44 and Table 6.

TABLE 6

| Reagent | IC50 (μM) in PC-3 cells | IC50 (μM) in DU-145 cells | IC50 (μM) in LNCaP cells |
| --- | --- | --- | --- |
| Chb-M' | 0.62 | 1.82 | 0.68 |
| Chb-S | 25.11 | 107.87 | 107.87 |
| Chlorambucil | N/A | 38.08 | 37.57 |
| Enzalutamide | 88.144 | 47.17 | — |

As evident from FIG. 44, Chb-M' dramatically inhibited the proliferation of both the androgen-dependent and -independent prostate cancer cell lines. In addition, Chb-M' showed far smaller 1050 values (0.62 μM in PC-3, 1.82 μM in DU-145, and 0.68 μM in LNCaP) as compared with other reagents.

(2) Inhibition of Expression of Prostatic Adenocarcinoma-Related Factor

To prostatic adenocarcinoma cell line PC-3, 5 μM Chb-M' was administered. After 6 hours, the mRNA levels of GATA2, E2F5, and AR (androgen receptors), which are important genes for proliferation of prostate cancer cells, were evaluated by qRT-PCR (see the above-described "Real-time quantitative PCR (qRT-PCR)"). As a control, DMSO was administered. Results are shown in FIG. 45. In the figure, the mRNA expression levels of GATA2, E2F5, and AR are shown as values relative to those in the DMSO-treated group. As evident from FIG. 45, the expressions of GATA2, E2F5, and AR were suppressed by Chb-M' at transcriptional levels.

(3) Effect on Apoptosis Induction

To PC-3 cells, 3 μM Chb-M' was administered. After 48 hours and 72 hours, the percentage of apoptosis was analyzed by PI-AnnexinV apoptosis staining. As a control, DMSO was administered. As a result, the apoptosis rate was increased depending on the concentration of Chb-M' (FIG. 46).

Example 11: Effect on Brain Tumor (1) Cell Proliferation Test

Different concentrations of various drugs (Chb-M', Chb-S, or chlorambucil) were added to media, and medulloblastoma cell line DAOY (SHH, TP53-mutated) was incubated for 48 hours. Cell viability after 48 hours was determined using Cell Count Reagent SF (nacalai tesque, Inc.) and Infinite (registered trademark) 200 PRO multimode reader (TECAN), and IC50 values (viability of 50%) were calculated (MTS assay using SF reagent): Results are shown in FIG. 47 and Table 7. As evident from FIG. 47, Chb-M' dramatically inhibited the proliferation of the medulloblastoma cell line. In addition, Chb-M' showed far smaller IC50 values (0.812 μM) as compared with other regents.

TABLE 7

| Reagent | IC50 (μM) |
|---|---|
| Chb-M' | 0.812 |
| Chb-S | 39.33 |
| Chlorambucil | 18.17 |

(2) Inhibition of Expression of Medulloblastoma-Related Factor

To medulloblastoma cell line DAOY, 1 μM Chb-M' was administered. After 6 hours, the mRNA levels of cancer promoting factors ROR1 and ROR2, which are important for medulloblastoma, were evaluated by qRT-PCR (see the above-described "Real-time quantitative PCR (qRT-PCR)"). As a control, DMSO was administered. Results are shown in FIG. 48. In the figure, the mRNA expression levels of ROR1 and ROR2 are shown as values relative to those in the DMSO-treated group. As evident from FIG. 48, the expressions of ROR family were suppressed by Chb-M' at transcriptional levels.

To DAOY cells, 1 μM Chb-M' was administered. After 24 hours, proteins were extracted, and the expression of ROR1 and ROR2 at protein level were confirmed by the Western blotting method (see the above-described "Immunoblotting") using an anti-ROR1 antibody and an anti-ROR2 antibody. As a control, DMSO was administered. Results are shown in FIG. 49. As evident from FIG. 49, Chb-M' suppressed the expression of ROR2 at a protein level. The expression of ROR1 was too weak to be detected.

Example 12: Effect on APL (Acute Promyelocytic Leukemia)

Chb-M' or ATRA (all-trans-retinoic acid: vitamin A derivative) was added to media, and p53-mutated APL cell line NB4 (purchased from DSMZ (Deutsche Sammlung von Mikroorganismen and Zellkulturen)) or p53-null APL cell line UF1 (provided by Department of Hematology and Oncology, Keio University School of Medicine) was incubated for 48 hours or 72 hours. Cell viability was determined using Cell Count Reagent SF (nacalai tesque, Inc.) and Infinite (registered trademark) 200 PRO multimode reader (TECAN), and IC50 values (viability of 50%) were calculated (MTS assay using SF reagent). Results are shown in FIG. 50-1, FIG. 50-2 and Table 8. ATRA is a first line therapeutic drug for use in the general clinical treatment of APL.

TABLE 8

| Reagent | Cell | Culture time | IC50 (μM) |
|---|---|---|---|
| Chb-M' | NB4 (p53MT) | 48 hours | 0.3567 |
|  |  | 72 hours | 0.04460 |
|  | UF1 (p53Null) | 48 hours | 1.748 |
|  |  | 72 hours | 0.6742 |
| ATRA | NB4 (p53MT) | 48 hours | 75.72 |
|  |  | 72 hours | 60.08 |
|  | UF1 (p53Null) | 48 hours | 12.43 |
|  |  | 72 hours | 10.30 |

As evident from FIG. 50-1, FIG. 50-2 and Table 8, Chb-M' dramatically inhibited the proliferation of APL cell line. Chb-M' showed remarkable inhibition of cell proliferation also in NB4, which is a p53-mutated cell line (FIG. 50-1 and Table 8). Although ATRA was slightly effective against UF1 as compared with NB4, both NB4 and UF1 were ATRA-resistant (FIG. 50-2 and Table 8). Chb-M' showed inhibition effect on cell proliferation in ATRA-resistant APL cell lines (FIG. 50-1, Table 8).

INDUSTRIAL APPLICABILITY

The RUNX inhibitor of the present invention can inhibit the activities of all members of RUNX family. The anti-tumor agent comprising the RUNX inhibitor of the present invention can target various types of cancers including leukemia by cluster regulation of RUNX family. The anti-tumor agent of the present invention exerts its effect even on tumors resistant to other molecular target drugs. Particularly, the anti-tumor agent of the present invention exerts its effect even on cancers on which the current clinically available molecular target drugs have no effect. Thus the anti-tumor agent of the present invention is expected to be used as a universal anticancer drug which is effective even against so called intractable cancers. In addition, the RUNX inhibitor of the present invention can be used as an antiallergic agent.

Sequence Listing Free text

SEQ ID NO:1: Forward primer for amplification of GAPDH gene
SEQ ID NO:2: Reverse primer for amplification of GAPDH gene
SEQ ID NO:3: Forward primer for amplification of BCL11A gene
SEQ ID NO:4: Reverse primer for amplification of BCL11A gene
SEQ ID NO:5: Forward primer for amplification of TRIM24 gene
SEQ ID NO:6: Reverse primer for amplification of TRIM24 gene
SEQ ID NO:7: Forward primer for amplification of IL3 gene
SEQ ID NO:8: Reverse primer for amplification of IL3 gene
SEQ ID NO:9: Forward primer for amplification of CSF2RB gene
SEQ ID NO:10: Reverse primer for amplification of CSF2RB gene
SEQ ID NO:11: Forward primer for amplification of p53 gene SEQ ID NO:12: Reverse primer for amplification of p53 gene
SEQ ID NO:13: Forward primer for amplification of CSF2 gene
SEQ ID NO:14: Reverse primer for amplification of CSF2 gene
SEQ ID NO:15: Forward primer for amplification of p21 gene
SEQ ID NO:16: Reverse primer for amplification of p21 gene
SEQ ID NO:17: Forward primer for amplification of BAX gene
SEQ ID NO:18: Reverse primer for amplification of BAX gene
SEQ ID NO:19: Forward primer for amplification of PUMA gene
SEQ ID NO:20: Reverse primer for amplification of PUMA gene
SEQ ID NO:21: Forward primer for amplification of MDM2 gene
SEQ ID NO:22: Reverse primer for amplification of MDM2 gene
SEQ ID NO:23: Forward primer for amplification of RUNX1 gene
SEQ ID NO:24: Reverse primer for amplification of RUNX1 gene
SEQ ID NO:25: Forward primer for amplification of RUNX2 gene
SEQ ID NO:26: Reverse primer for amplification of RUNX2 gene
SEQ ID NO:27: Forward primer for amplification of RUNX3 gene
SEQ ID NO:28: Reverse primer for amplification of RUNX3 gene
SEQ ID NO:29: Forward primer for amplification of Pan RUNX gene
SEQ ID NO:30: Reverse primer for amplification of Pan RUNX gene
SEQ ID NO:31: Forward primer for amplification of CBFB gene
SEQ ID NO:32: Reverse primer for amplification of CBFB gene

---

The invention claimed is:

1. A RUNX inhibitor, wherein the inhibitor binds to a RUNX binding sequence on a DNA to inhibit binding of a RUNX family member to the binding sequence and the inhibitor comprises a conjugate of an acting agent and a pyrrole-imidazole polyamide that binds to the RUNX binding sequence, wherein the pyrrole-imidazole polyamide recognizes and binds to the RUNX binding sequence of 5'-TGTGGT-3' or 5'-TGCGGT-3', and wherein the pyrrole-imidazole polyamide comprises polyamides containing N-methylpyrrole units (P), N-methylimidazole units (I) and a γ-aminobutyric acid moiety, wherein the P, I and the γ-aminobutyric acid moiety are linked to one another via amide bonds, wherein P is optionally replaced by 3-hydroxypyrrole (Hp) or β-alanine, and wherein a methyl group on a nitrogen atom at position 1 of P or I is optionally substituted by hydrogen or an alkyl group other than a methyl group, and wherein the conjugate of an acting agent and a pyrrole-imidazole polyamide is selected from the group consisting of compounds represented by formula I:

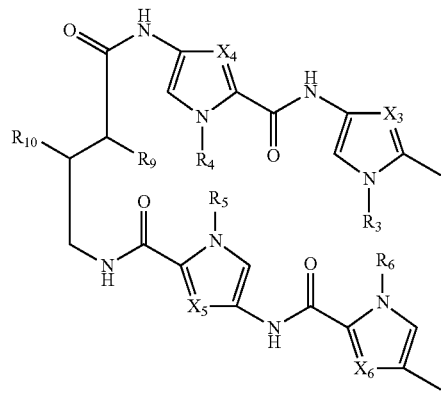

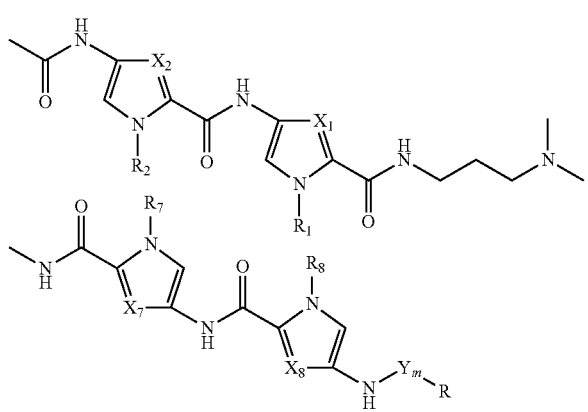

or formula II:

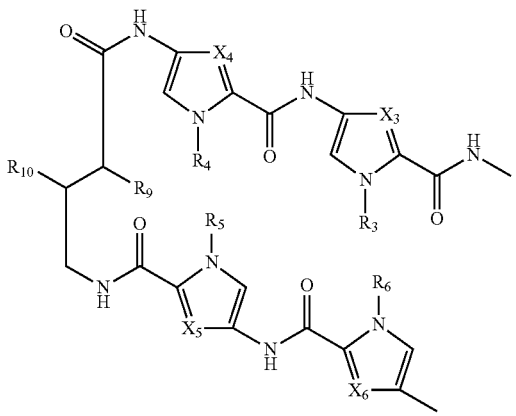

wherein, in formula I or formula II, $X_1$ represents CH or N, $X_2$ represents CH or N, $X_3$ represents CH or N, $X_4$ represents CH or N, $X_5$ represents CH or N, $X_6$ represents CH or N, $X_7$ represents CH or N, $X_8$ represents CH or N, Y represents an amide bond, a phosphodisulfide bond, an ester bond, a coordinate bond, or an ether bond, or a moiety containing a functional group that forms at least one selected from the bonds, m represents an integer of 0 to 5, $R_1$ represents H or alkyl, $R_2$ represents H or alkyl, $R_3$ represents H or alkyl, $R_4$ represents H or alkyl, $R_5$ represents H or alkyl, $R_6$ represents H or alkyl, $R_7$ represents H or alkyl, $R_8$ represents H or alkyl, wherein each alkyl is a C1-C10 linear, branched, or cyclic saturated or unsaturated alkyl group, $R_9$ represents H or $NHR_{11}$, $R_{10}$ represents H or $NHR_{11}$, $R_{11}$ represents H, biotin, or a fluorescent group, and R represents an acting agent, and wherein in the pyrrole-imidazole polyamide, a P/I pair binds to a C•G base pair, a P/P pair binds to an A•T or T•A base pair, a I/P pair binds to a G•C base pair, a Hp/P pair binds to a T•A base pair, a β-alanine/β-alanine pair binds to an A•T or T•A base pair.

2. The RUNX inhibitor according to claim 1, wherein the acting agent is an alkylating agent.

3. The RUNX inhibitor according to claim 2, wherein the alkylating agent is selected from the group consisting of chlorambucil, duocarmycin, seco-CBI (1-chloromethyl-5-hydroxy-1,2-dihydro-3H-benzo[e]indole), pyrrolobenzodiazepine, and Nitrogen mustard.

4. The RUNX inhibitor according to claim 3, wherein the alkylating agent is chlorambucil.

5. The RUNX inhibitor according to claim 4, wherein the conjugate of an acting agent and a pyrrole-imidazole polyamide is selected form the group consisting of compounds represented by formulae:

[Chemical formula 3]

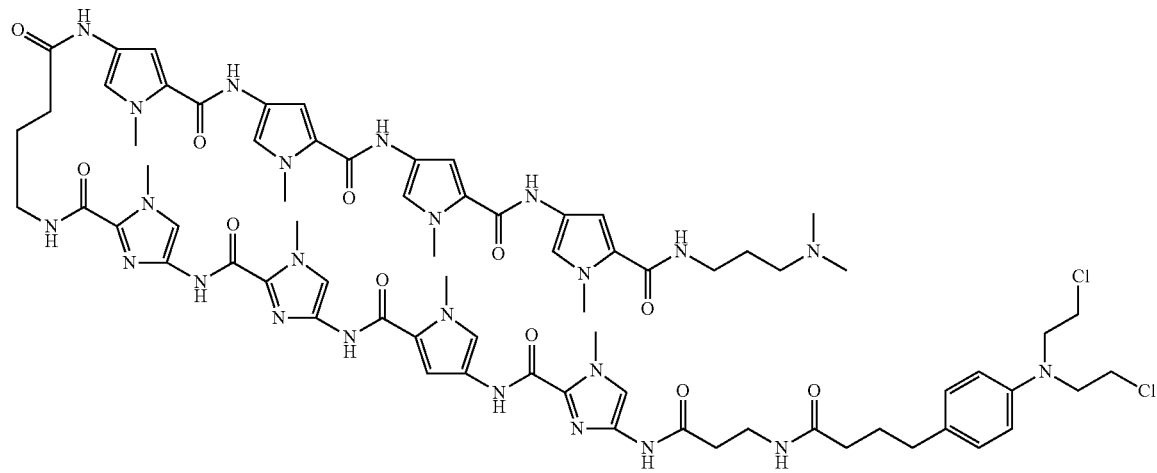

Chb-M'

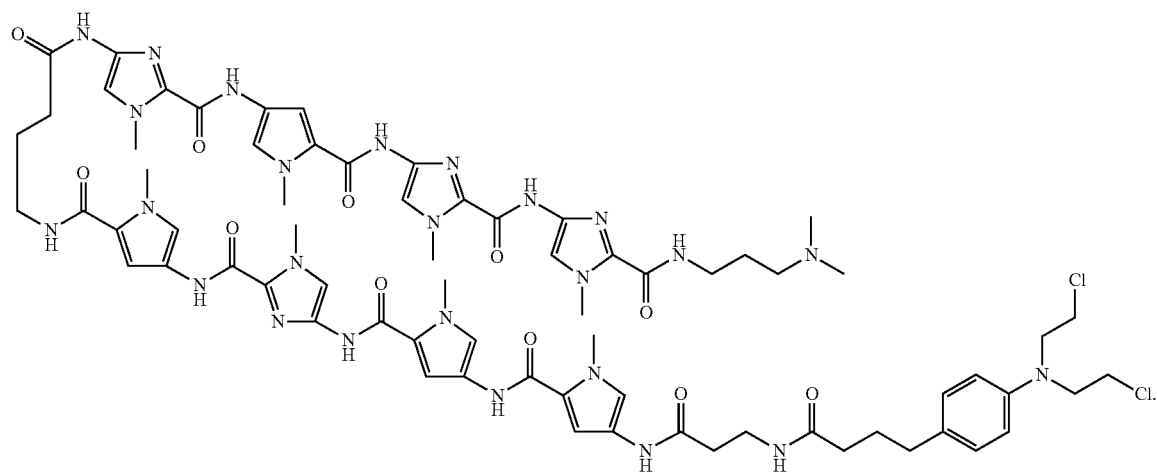

Chb-50

6. The RUNX inhibitor according to claim 1, which inhibits binding of all members of RUNX family to the RUNX binding sequence.

7. A pharmaceutical composition comprising the RUNX inhibitor according to claim 1.

8. The pharmaceutical composition according to claim 7, which is an antitumor agent.

9. The pharmaceutical composition according to claim 7, which is antiallergic agent.

10. The pharmaceutical composition according to claim 8, which is used in combination with another antitumor agent.

11. The pharmaceutical composition according to claim 8, for treatment of at least one selected from the group consisting of leukemia, lymphoma, multiple myeloma, lung cancer, esophageal cancer, gastric cancer, colon cancer, renal cell cancer, neuroblastoma, skin cancer, breast cancer, prostate cancer, and brain tumor.

12. A therapeutic method of cancer, mast cell diseases, allergy, or immunological diseases, the method comprising inhibiting binding of a RUNX family member to a RUNX binding sequence on a DNA by administering the RUNX inhibitor of claim 1 to a subject in need thereof,
   wherein the cancer is selected from the group consisting of leukemia, lymphoma, multiple myeloma, lung cancer, esophageal cancer, gastric cancer, colon cancer, renal cell cancer, neuroblastoma, skin cancer, breast cancer, prostate cancer, and brain tumor.

13. The therapeutic method according to claim 12, wherein the RUNX inhibitor is administered in combination with another antitumor agent.

* * * * *

```
                         SEQUENCE LISTING

<160> NUMBER OF SEQ ID NOS: 37

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
catgttcgtc atggggtgaa cca                                              23

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
agtgatggca tggactgtgg tcat                                             24

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
aaccccagca cttaagcaaa                                                  20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ggaggtcatg atcccttct                                                   20

<210> SEQ ID NO 5
```

```
<211> LENGTH: 24
<212> TYPE: DNA
<213> ORGANISM: Artificial Sequence
<220> FEATURE:
<223> OTHER INFORMATION: Primer

<400> SEQUENCE: 5
gcgcctactt ttatttcttt actg                                          24

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
aatgcttttg aggcgtttct t                                             21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aatctcctgc catgtctgcc                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
agatcgcgag gctcaaagtc                                               20

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
agcccagatg cagggga                                                  17

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cccaggatgt caggtaggga                                               20

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
```

```
ccccteetgg cccctgtcat cttc                                          24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
gcagcgcctc acaacctccg tcat                                          24

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
ggccagccac tacaagcagc act                                           23

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
caaaggggat gacaagcaga aag                                           23

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
tgtggacctg tcactgtctt g                                             21

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aatctgtcat gctggtctgc                                               20

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
catgttttct gacggcaact tc                                            22

<210> SEQ ID NO 18
<211> LENGTH: 20
<212> TYPE: DNA
```

```
<213> ORGANISM: Artificial Sequence
<220> FEATURE:
<223> OTHER INFORMATION: Primer

<400> SEQUENCE: 18
agggccttga gcaccagttt                                                   20

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
gcaggcacct aattgggct                                                    19

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
atcatgggac tcctgccctt a                                                 21

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
acctcacaga ttccagcttc g                                                 21

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
tttcatagta taagtgtctt ttt                                               23

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23
ctgctccgtg ctgcctac                                                     18

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
agccatcaca gtgaccagag t                                                 21
```

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
ggttaatctc cgcaggtcac t                                                    21

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
cactgtgctg aagaggctgt t                                                    21

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
cagaagctgg aggaccagac                                                      20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
gtcggagaat gggttcagtt                                                      20

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
gcaccgacag ccccaactt                                                       19

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gtcttgttgc agcgccagtg                                                      20

<210> SEQ ID NO 31
<211> LENGTH: 19
<212> TYPE: DNA
<213> ORGANISM: Artificial Sequence
<220> FEATURE:

```
<223> OTHER INFORMATION: Primer

<400> SEQUENCE: 31
tgtgagatta agtacacgg                                                      19

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
taatgcatcc tcctgctggg ct                                                  22

<210> SEQ ID NO 33
<211> LENGTH: 19
<212> TYPE: DNA
<213> ORGANISM: Homo sapiens

<400> SEQUENCE: 33
agcttcactc tgaccatca                                                      19

<210> SEQ ID NO 34
<211> LENGTH: 19
<212> TYPE: DNA
<213> ORGANISM: Homo sapiens

<400> SEQUENCE: 34
aacctcgaag acatcggca                                                      19

<210> SEQ ID NO 35
<211> LENGTH: 22
<212> TYPE: DNA
<213> ORGANISM: Homo sapiens

<400> SEQUENCE: 35
aaggttcaac gatctgagat tt                                                  22

<210> SEQ ID NO 36
<211> LENGTH: 21
<212> TYPE: DNA
<213> ORGANISM: Homo sapiens

<400> SEQUENCE: 36
aagcagctat gaatccattg t                                                   21

<210> SEQ ID NO 37
<211> LENGTH: 19
<212> TYPE: DNA
<213> ORGANISM: Photinus pyralisd

<400> SEQUENCE: 37
cgtacgcgga atacttcga                                                      19
```